(12) United States Patent
Arkin et al.

(10) Patent No.: US 6,806,279 B2
(45) Date of Patent: Oct. 19, 2004

(54) SMALL-MOLECULE INHIBITORS OF INTERLEUKIN-2

(75) Inventors: Michelle R. Arkin, San Francisco, CA (US); Robert S. McDowell, San Francisco, CA (US); Johan D. Oslob, Sunnyvale, CA (US); Brian C. Raimundo, San Francisco, CA (US); Nathan D. Waal, San Francisco, CA (US); Chul Hyun Yu, San Francisco, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 10/024,665

(22) Filed: Dec. 17, 2001

(65) Prior Publication Data

US 2003/0149049 A1 Aug. 7, 2003

(51) Int. Cl.$^7$ .................... C07D 401/04; C07D 401/14; C07D 403/04; A61K 31/4155
(52) U.S. Cl. .................. 514/326; 514/218; 514/254.05; 514/314; 514/318; 540/575; 544/371; 546/167; 546/194; 546/211
(58) Field of Search ................................. 546/211, 194; 514/326, 318

(56) References Cited

FOREIGN PATENT DOCUMENTS

WO WO 96/32938 * 10/1996

OTHER PUBLICATIONS

Poulain et al., From Hit to Lead. Combining Two Complementary Methods for Focused Library Design. Application to mu Opiate Ligands. J. Med. Chem., vol. 44, No. 21, pp. 3378–3390, Sep. 2001.*

Collins et al., Chem. Abstract 129:216582, 1998.*
Xu et al., Chem. Abstract 129:81705, 1998.*
Rowley et al., 4–Heterocyclypiperidines as Selective High Affinity Ligands at the Human Dopamine D4 receptor, J. Med. Chem., vol. 40, No. 15, pp. 2374–2385, 1997.*
Berndt, William G et al., "Mutagenic Analysis of a Receptor Contact Site on Interleukin–2: Preparation of an IL–2: Preparation of an Il–2 Analog with Increased Potency", *Biochemistry 1994*, vol. 33, pp. 6571–6577.
Landgraf, Bryan E. et al., "Conformational Pertubation of Interleukin–2 A strategy for the Design of Cytokin Analogs", *Proteins: Structure, Function, and Genetics*, vol. 9, pp. 207–216, (1991).
Mastsuoka, et al., "Unraveling the Structure of IL–2", *Science*, vol. 257, Jul. 17, 1992, pp. 410–413.
Suave, K. et al., "Localization in human interleukin 2 of the binding site to the ☐ chain (p55) of the interleukin 2 receptor", *Proc. Natl. Acad. Sci. USA Immunology*, vol. 88, pp. 4636–4640, Jun. 1991.
Tilley et al., "Identification of a Small Molecule Inhibitor of the IL–2/IL–2R☐ Receptor Interaction Which Binds to IL–2", *J. Amer. Chem. Soc.*, 1997, vol. 119, pp. 7589–7590.
Tilley et al., "Preparation of Carboalkoxyalkylphenylalanine Derivatives from Tyrosine", *J. Org. Chem.*, 1990, vol. 55, pp. 906–910.

* cited by examiner

*Primary Examiner*—Deepak Rao
(74) *Attorney, Agent, or Firm*—Morrison & Foerster LLP

(57) ABSTRACT

Compounds of formulae I and I', methods of making them, pharmaceutical compositions containing them, and methods for their use. The compounds are antagonists of IL-2/IL-2R binding; and are useful for the treatment of interleukin-2 mediated diseases, such as autoimmune diseases (such as rheumatoid arthritis, multiple sclerosis, uveitis, and psoriasis), allograft rejection, and graft-versus-host disease.

19 Claims, No Drawings

SMALL-MOLECULE INHIBITORS OF INTERLEUKIN-2

BACKGROUND OF THE INVENTION

1. Field of the Invention

This invention relates to small-molecule inhibitors of interleukin-2.

2. Description of Related Art

The cytokine interleukin-2 is a principal regulator of the Th1, or cell-mediated, immune response [Waldmann et al., "Contrasting Roles of IL-2 and IL-15 in the Life and Death of Lymphocytes: Implications for Immunotherapy", *Immunity*, 2001, 14, 105–110]. When the body launches a Th1 response against its own cells, autoimmune diseases (such as rheumatoid arthritis, multiple sclerosis, uveitis, and psoriasis) occur. Similarly, cell-mediated immunity causes rejection of transplanted organs (allograft rejection) and graft-versus-host disease (GVHD), a serious complication that can occur after bone-marrow transplantation.

The IL-2 receptor system (IL-2R) contains three subunits. The dimeric receptor, containing the beta and gamma subunits, is found on most immune cells; IL-2-mediated signaling through this receptor stimulates basal cell growth of T-cells, natural killer cells, and macrophages. During a Th1 immune response, the alpha chain of the IL-2 receptor (IL-2Rα) is expressed on the surface of activated T-cells. Binding of IL-2 to this trimeric receptor causes the activated T-cells to proliferate, and this T-cell proliferation is in turn responsible for stimulating the cell-mediated immune response.

Currently used immunosuppressive protocols designed to inhibit allograft rejection and GVHD involve the use of general immunosuppressants such as azathioprine, cyclosporin, rapamycin, tacrolimus, mycophenolate mofetil, and corticosteroids, generally in combinations of two or more of these drugs. All of these can cause toxic side effects to non-lymphoid tissues. It would be desirable to develop inhibitors of the Th1 immune response that selectively block the proliferative activity of IL-2/IL-2Rα binding without affecting the role of IL-2 role in basal cell growth, as these selective IL-2Rα antagonists should be safer than general inmunosuppressants.

Recently, two antibodies directed against IL-2Rα (basiliximab and daclizumab) have been approved for allograft rejection. Studies have shown that these antibodies provide benefits over the standard three-drug (azathioprione, cyclosporin and mycophenolate mofetil or steroids) regime without some of the side effects of that therapy (Berard et al., "A review of interleukin-2 receptor antagonists in solid organ transplantation", *Pharmacotherapy* 1999, 19, 1127–1137; Nashan, "The interleukin-2 inhibitors and their role in low-toxicity regimens", *Transplantation Proc.* 1999, 31 (*Suppl.* 8A), 23S–26S). However, these antibodies are not orally bioavailable.

Application of new immunosuppressants to autoimmune disease has lagged behind treatments for graft rejection. While autoimmune diseases have diverse manifestations, the up-regulation of the immune response appears to be a common underlying pathology. Important unmet medical needs exist for autoimmune diseases such as rheumatoid arthritis, multiple sclerosis (MS), uveitis, and psoriasis. Several of the therapeutics currently used to treat autoimmune diseases require intravenous, intramuscular or subcutaneous injection, and are thus suboptimal for chronic use. Nevertheless, several ongoing clinical trials are investigating the use of anti-IL-2Rα antibodies for multiple sclerosis and other autoimmune diseases. See, for example, Brok et al., "Prophylactic and therapeutic effects of a humanized monoclonal antibody against the IL-2 receptor (daclizumab) on collagen-induced arthritis (CIA) in rhesus monkeys", *Clin. Exp. Immunol.* 2001, 124, 134–141.

Thus, despite improved therapies for immunosuppression, autoimmune diseases continue to be important pathologies in need of safe and efficacious treatments. To date, no small-molecule IL-2 antagonists have been reported. It would be desirable to develop a small-molecule orally available inhibitor of the IL-2/IL-2Rα interaction.

The disclosures of all documents referred to throughout this application are incorporated herein by reference.

SUMMARY OF THE INVENTION

In a first aspect, this invention is compounds of formula I or formula I'

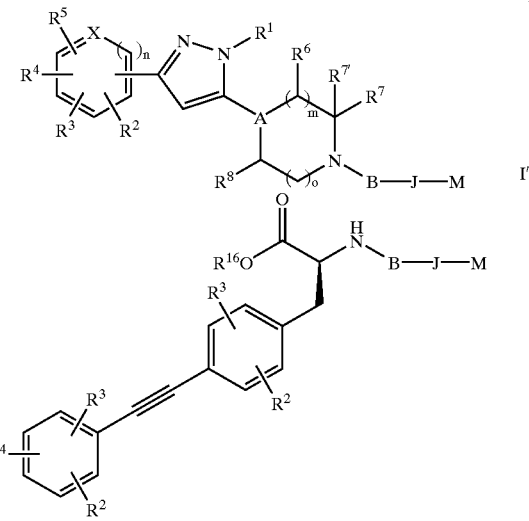

where,
m is an integer selected from 0, 1, and 2;
n and o are integers independently selected from 0 and 1;
A is selected from the group consisting of N and CH;
B is selected from the group consisting of —CH$_2$—CH$_2$—, —CH$_2$—CH$_2$—CH$_2$—, —CH$_2$—CH$_2$—NH—, —CH$_2$—O—CH$_2$—, —CH$_2$—S—CH$_2$—, —C(=O)—NH—, —C(=O)—CH$_2$—, —CH$_2$—C(=O)—NH—, —C(=O)—CH$_2$—C(=O)—, —C(=O)—NH—CH$_2$—, —C(=O)—, —S(=O)—, —S(=O)$_2$—, —S(=O)—NH—, —S(=O)$_2$—NH—, —S(=O)—CH$_2$—, —S(=O)$_2$CH$_2$—, —S(=O)—CH$_2$—NH—, —S(=O)$_2$—CH$_2$—NH—, —S(=O)$_2$—NH—CH$_2$—, —CH$_2$—S(=O)$_2$—NH—, —C(=O)—NH—S(=O)$_2$—, —S(=O)$_2$—NH—C(=O)—, —C(=O)—CH$_2$—S(=O)$_2$—, and —S(=O)$_2$—CH$_2$—C(=O)—;

J is absent or selected from the group consisting of —O—, —S—, —CHR$^{15}$—O—, —CH$_2$—CHR$^{15}$—O—, —NH—, —NH—CHR$^{15}$—, —NH—CHR$^{15}$—C(=O)—, —C(=O)—, —CH$_2$—, —CHR$^{15}$—CH$_2$—NH—, —C(=O)—CHR$^{15}$—, —NH—C(=O)—CH(C$_1$-C$_6$alkyl)-, —NH—C(=O)—CH(C$_3$-C$_{12}$cycloalkyl)-, —CH$_2$—CH$_2$—, —CH$_2$—NH$_2$—, —CH$_2$—NH$_2$—C(=O)—, —CH$_2$—NH$_2$—C(=O)—C$_1$-C$_6$alkyl-, —CH$_2$—NH$_2$—C(=O)—CH(C$_3$-C$_{12}$cycloalkyl)-, and —C(=O)—CHR$^{15}$—NH—; or B—J is selected from the group consisting of —C(=O)—CH$_2$—NH—C(=O)—CH(C$_1$–C$_6$alkyl, —C(=O)—CH$_2$—CH$_2$—NH—C(=O)—CH(C$_3$–C$_{12}$cycloalkyl)-, —C(=O)—NH—(C$_2$–C$_6$alkyl), —S(=O)$_2$—NH—(C$_2$–C$_6$alkyl)-, —C(=O)—NH—, —S(=O)$_2$—NH—, —C(=O)—CH— and —S(=O)—CH$_2$—, L is selected from the group consisting of —O—, —CH$_2$—O—, —O—CH$_2$—, —CH$_2$—CH$_2$—O—, —O—CH$_2$—CH$_2$—, —CH$_2$—O—CH$_2$—, —CH$_2$—S—CH$_2$—, —C(=O)—NH—, —O—C(=O)—NH—, —CH$_2$—C(=O)—NH—, —C(=O)—CH$_2$—NH—, —C(=O)—NH—CH$_2$—, —NH—C(=O)—, NH—C(=O)—O—, —NH—CH$_2$—C(=O)—, —NH—C(=O)—CH$_2$—, —CH$_2$—NH—C(=O)—, —NH—C(=O)—NH—, —NH—S(=O)$_2$—NH—, —NH—S(=O)$_2$—, —NH—S(=O)$_2$—CH$_2$—, —CH$_2$—NH—S(=O)$_2$—, —S(=O)$_2$—NH—, —S(=O)$_2$—NH—CH$_2$—, —CH$_2$—S(=O)$_2$—NH—, —C(=O)—NH—S(=O)$_2$—, —S(=O)$_2$—NH—C(=O)—, —CH$_2$—NH—, —CH$_2$—CH$_2$—NH—, —NH—CH$_2$—, —NH—CH$_2$—CH$_2$—, —CH$_2$—NH—CH$_2$—, —C≡C—, —CH$_2$—C≡C—, —CH$_2$—CH$_2$—, —CH$_2$—CH$_2$—CH$_2$—, —CH$_2$—CH=CH—, CH=CH—CH$_2$—, and —CH=CH—;

M is selected from the group consisting of R$^9$ and an optionally substituted group selected from phenyl, naphthyl, C$_3$–C$_7$-cycloalkyl, and heterocyclyl, the heterocyclyl group being aliphatic, partially unsaturated, or aromatic, and containing 1 or 2 rings each containing 5–7 ring atoms of which 0–3 are hetero atoms selected from N, O and S, provided that at least one ring contains a heteroatom and where any ring carbon or sulfur may optionally be oxidized, the optional substituents being up to three groups selected from R$^1$, R$^2$ and R$^9$; or M is selected from the group consisting of

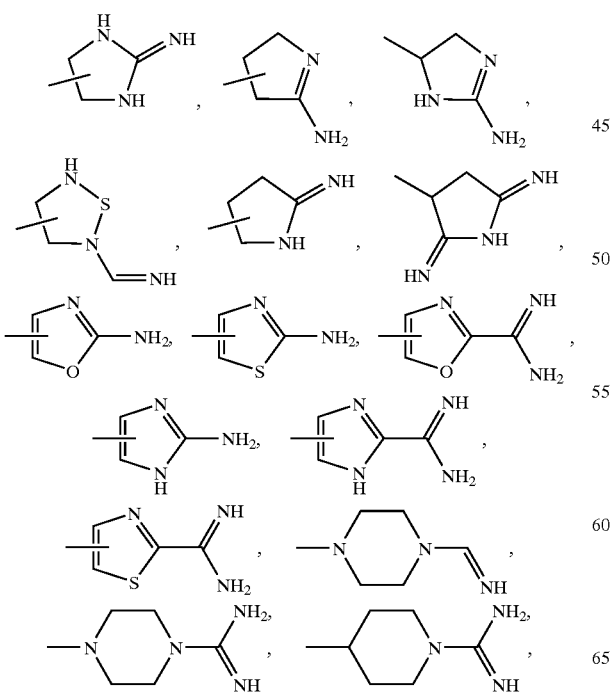

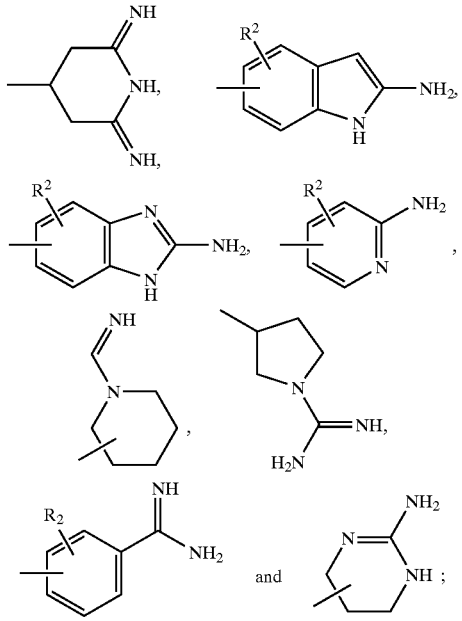

Q is selected from the group consisting of —C(=O)OR$^{16}$, —C(=O)—NH—C(=O)—CF$_3$, —C(=O)—NH—S(=O)$_2$—R$^2$, —C(=O)—NR$^1$—OH, 5-oxo-4,5-dihydro[1,2,4]oxadiazol-3-yl, and tetrazolyl;

X is A when n is 1, and is CH, N, O or S when n is 0;

R$^1$ is selected from the group consisting of hydrogen, (C$_1$–C$_6$)alkyl, halo-(C$_1$–C$_6$)alkyl, and (C$_3$–C$_6$)cycloalkyl;

R$^2$, R$^3$ and R$^5$ are individually selected from the group consisting of hydrogen, cyano, nitro, phenyl, phenoxy, benzyl, C$_1$–C$_6$alkyl, halo, halo-C$_1$–C$_6$alkyl, C$_3$–C$_6$cycloalkyl, C$_1$–C$_6$alkoxy, hydroxy, C$_1$–C$_2$alkoxy-methoxy, hydroxy-C$_1$–C$_6$alkyl, formyl, C$_1$–C$_6$alkylcarbonyl, amino, C$_1$–C$_6$alkylamino, aminocarbonyl, C$_1$–C$_6$alkylaminocarbonyl, formylamino, and C$_1$–C$_6$alkylcarbonylamino, where any alkyl or phenyl may optionally be substituted with halo or Q;

R$^4$ selected from the group consisting of R$^2$ and

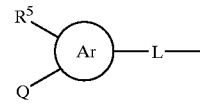

where Ar is a homo- or hetero-aryl group having 1 or 2 rings, each ring containing 5, 6 or 7 ring atoms of which 1–3 may be heteroatoms selected from N, O and S;

R$^6$ is selected from the group consisting of hydrogen, C$_1$–C$_6$alkyl, halo, halo-C$_1$–C$_6$alkyl, C$_3$–C$_6$cycloalkyl, C$_1$–C$_6$alkoxy, C$_1$–C$_6$alkoxy-C$_1$–C$_6$alkyl, hydroxy, hydroxy-C$_1$–C$_6$alkyl, HC(=O)—C$_1$–C$_6$alkyl, carboxy, carboxy-C$_1$–C$_6$alkyl, carbonylamino-C$_1$–C$_6$alkyl, aminocarbonyl, (C$_1$–C$_6$alkyl)aminocarbonyl, di(C$_1$–C$_6$alkyl)aminocarbonyl, and aminocarbonyl-C$_1$–C$_6$alkyl;

R$^7$ is selected from the group consisting of hydrogen, C$_1$–C$_6$ alkyl, halo, halo-C$_1$–C$_6$alkyl, C$_3$–C$_6$cycloalkyl, C$_1$–C$_6$alkoxy, C$_1$–C$_6$alkoxy-C$_1$–C$_6$alkyl, hydroxy, hydroxy-$C_1$-$C_6$alkyl, HC(=O)-$C_1$-$C_6$alkyl, carboxy, carboxy-$C_1$-$C_6$alkyl, carbonylamino-$C_1$-$C_6$alkyl, aminocarbonyl, ($C_1$-$C_6$alkyl)aminocarbonyl, di($C_1$-$C_6$alkyl)aminocarbonyl, and aminocarbonyl-$C_1$-$C_6$alkyl;

$R^{7'}$ is hydrogen; or $R^7$ $R^{7'}$ together with the carbon to which they are bonded form —C(=O)—;

$R^8$ is selected from the group consisting of hydrogen, hydroxy, $C_1$-$C_6$alkoxy, $C_1$-$C_6$alkyl, halo, halo-$C_1$-$C_6$alkyl, and $C_3$-$C_6$cycloalkyl;

$R^9$ is selected from the group consisting of —$NR^{10}R^{11}$, —C(=$NR^{12}$)—$NHR^{13}$, —N=$CR^{14}$—$NR^{10}R^{11}$, —$NR^{13}$—$CR^{14}$=$NR^{12}$, and —$NR^{13}$—C($NR^{12}$)—$NHR^{13}$;

$R^{10}$, $R^{11}$, $R^{12}$, $R^{13}$ and $R^{14}$ are independently selected from the group consisting of hydrogen, hydroxy, hydroxy-$C_1$-$C_6$alkyl, $C_1$-$C_6$alkyl, halo-$C_1$-$C_6$alkyl, $C_1$-$C_6$alkoxy, $C_1$-$C_6$alkoxy-$C_1$-$C_6$alkyl, and $C_3$-$C_7$cycloalkyl; or any member of the group $R^{10}$, $R^{11}$, $R^{12}$, and $R^{13}$ together with the nitrogen to which it is attached forms a 5, 6 or 7 member heterocycle with any other member of the group, the heterocycle optionally containing one additional heteroatom selected from N, O and S;

$R^{15}$ is selected from the group consisting of hydrogen, $C_1$-$C_{12}$alkyl, $C_3$-$C_7$cycloalkyl, aminocarbonyl, $C_1$-$C_6$alkylaminocarbonyl, and di($C_1$-$C_6$alkyl)aminocarbonyl; and $R^{16}$ is selected from the group consisting of hydrogen, $C_1$-$C_6$alkyl, $C_3$-$C_{13}$cycloalkyl, $C_6$-$C_{10}$aryl, acetylamino-$C_1$-$C_{12}$alkyl, $C_1$-$C_6$alkylcarbonyloxy-$C_1$-$C_6$alkyl, and $C_6$-$C_6$aryl-$C_6$-$C_{10}$aryl-$C_0$-$C_6$alkylcarbonyloxy-$C_1$-$C_6$alkyl, and the pharmaceutically acceptable salts thereof;

provided that the compound is not N-[2-[1-(aminoiminomethyl)-3-piperidinyl]-1-oxoethyl]-4-phenylethynyl-phenylalanine methyl ester or a pharmaceutically acceptable salt thereof.

In a second aspect, this invention is pharmaceutical compositions comprising a pharmaceutically acceptable excipient and a therapeutically effective amount of at least one compound of the first aspect of this invention. These compositions find use for the treatment of autoimmune diseases (e.g. rheumatoid arthritis, multiple sclerosis, uveitis, and psoriasis), allograft rejection, and GVHD.

In a third aspect, this invention is a method of treating an animal having disease for which antagonism of IL-2/IL-2R binding is indicated (an interleukin-2 mediated disease), such as autoimmune diseases, allograft rejection, and GVHD, comprising administration to that animal of a therapeutically effective amount of at least one compound of the first aspect of this invention, optionally in conjunction with at least one other conventional therapeutic agent for the disease being treated.

In a fourth aspect, this invention is the use of compounds of the first aspect of this invention in the preparation of medicaments for the treatment of diseases capable of treatment by an antagonist of IL-2/IL-2R binding, such as autoimmune diseases, allograft rejection, and GVHD.

In a fifth aspect, this invention is methods of preparing the compounds of the first aspect of this invention.

DETAILED DESCRIPTION OF THE PREFERRED EMBODIMENTS

Definitions

"Alkyl" means a linear hydrocarbyl group having the range of carbon atoms specified, or a branched or cyclic hydrocarbyl group having at least 3 carbon atoms within the range of carbon atoms specified. Exemplary alkyl groups include methyl, ethyl, isopropyl, cyclopropyl, tert-butyl, cyclopropylmethyl, and hexyl.

"Animal" includes humans and non-human mammals, such as companion animals (cats, dogs, and the like) and farm animals (cattle, horses, sheep, goats, swine, and the like).

"Disease" includes any unhealthy condition of an animal, including injury, particularly interleukin-2 mediated diseases, such as autoimmune diseases (e.g. rheumatoid arthritis, multiple sclerosis, uveitis, and psoriasis), allograft rejection, and graft-versus-host disease.

"Halo" means fluoro, chloro, or bromo.

"Haloalkyl" means alkyl substituted with from 1 to 3 halogen atoms selected from fluorine, chlorine, or bromine.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salts" means salts that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arenesulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

The compounds of formula I' possess a chiral center in the alanine portion of the molecule, where they have the normal (S) configuration. The compounds of this invention may also possess one or more (additional) chiral centers. Methods for the determination of stereochemistry and the separation of stereoisomers are well known to a person of ordinary skill in the art [see the discussion in Chapter 4 of March, "Advanced Organic Chemistry", 4th ed., 1992, John Wiley and Sons, New York, N.Y.].

Implicit hydrogen atoms on carbon and sometimes on nitrogen atoms are generally omitted from the formulae for clarity, but should be understood to be present.

Presently Preferred Compounds

While the broadest definition of the invention is set out in the Summary of the Invention, certain compounds of this invention are presently preferred.

Presently preferred compounds of this invention are compounds of formula I that are compounds of formula II

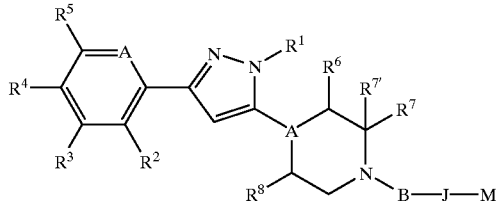

II where the substituents are as defined for formula I; and the pharmaceutically acceptable salts thereof.

More preferred compounds are compounds of formula II that are compounds of formula III or formula III'

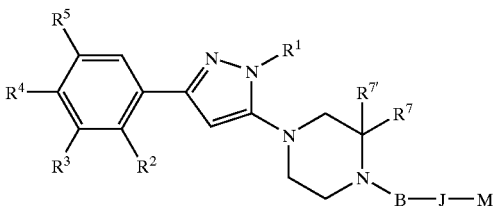

III

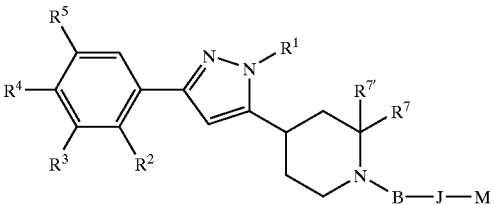

III' where the substituents are as defined for formula I; and the pharmaceutically acceptable salts thereof.

Other preferred compounds are compounds of formula I that are compounds of formula IV

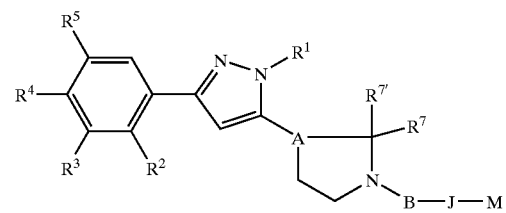

IV a where the substituents are as defined for formula I;

and the pharmaceutically acceptable salts thereof.

Presently preferred classes of compounds of this invention include those where:

(1) $R^1$ is hydrogen or ($C_1$–$C_6$alkyl), especially methyl;
(2) $R^2$ and $R^3$ are hydrogen, $C_1$–$C_6$alkyl, cyano, or halo (especially chloro), and more preferably one or both are chloro;
(3) $R^4$ is

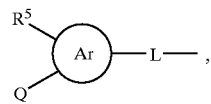

especially where one or more of the following preferences applies: Ar is selected form the group consisting of phenyl, furyl, thienyl, oxazolyl, thiazolyl, and pyrrolyl; $R^5$ is hydroxy, $C_1$–$C_2$alkoxy-methoxy or $C_1$–$C_3$-alkoxy; Q is a negatively charged species such as carboxy (or a prodrug thereof) or tetrazolyl; and L is —O—, —CH$_2$—O—, —O—CH$_2$—, or —CH$_2$—CH$_2$—O—;

(4) B is —C(=O)— or —S(=O)$_2$—;
(5) J is —CH$_2$—, —CH$_2$—CH$_2$—, —NH—, —NH—CH$_2$—, —CH$_2$—NH—, —CH$_2$—NH—C(=O)—, —CH$_2$—NH—C(=O)—$C_1$–$C_6$alkyl- and —CH$_2$—NH—C(=O)—CH($C_3$–$C_{12}$cycloalkyl)-;
(6) B—J combinations are —C(=O)—CH$_2$—NH—C(=O)—CH($C_1$–$C_6$alkyl)-, —C(=O)—CH$_2$—NH—C(=O)—CH($C_3$–$C_{12}$cycloalkyl)-, —C(=O)—NH—($C_2$–$C_6$alkyl)-, —S(=O)$_2$—NH—($C_2$–$C_6$alkyl)-, —C(=O)—NH—, —S(=O)$_2$—NH—, —C(=O)—CH$_2$— and —S(=O)$_2$—CH$_2$—;
(7) M is selected from the group consisting of $R^9$,

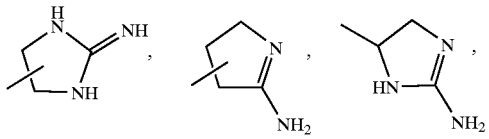

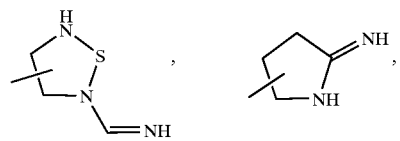

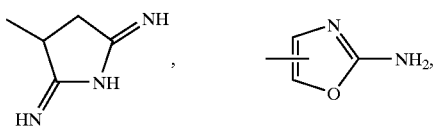

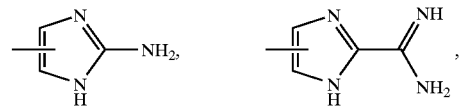

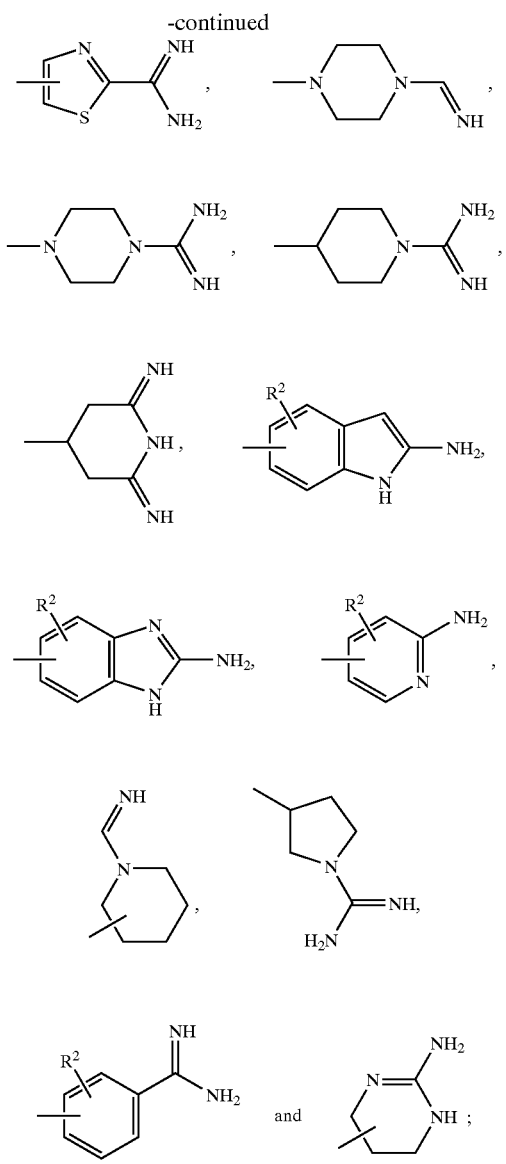

especially where M is not $R^9$.

A number of different preferences have been given above, and following any one of these preferences results in a compound of this invention that is more presently preferred than a compound in which that particular preference is not followed (e.g. compounds of formula III or formula III' are more preferred than compounds of formula II that are not compounds of formula III or formula III'; and compounds of formula II are more preferred than compounds of formula I that are not compounds of formula II). However, substituent preferences in particular are generally independent [although the B—J preferences are not entirely independent of the B preferences and J preferences], and additive; and following more than one of these preferences may result in a more presently preferred compound than one in which fewer of the preferences are followed.

Presently particularly preferred compounds of this invention are the compounds of Examples 1 to 76, and the pharmaceutically acceptable salts thereof.

Pharmacology and Utility

The compounds of this invention are antagonists of IL-2/IL-2R binding. Their activity as antagonists of IL-2/IL-2R binding in vitro can be measured by methods such as the scintillation proximity assay described in Example 77 to demonstrate that the compounds inhibit binding of IL-2 to IL-2Rα in a dose-dependent fashion. Other methods, such as ELISA, enzyme-linked protein binding assays, and energy transfer assays, can also be used.

In addition to these assays demonstrating that compounds antagonize binding of IL-2 to IL-2Rα, other measurements can be used to demonstrate directly the binding of compounds to IL-2. Such methods include NMR, x-ray crystallography, analytical ultracentrifugation, surface plasmon resonance (SPR, Biacore), and isothermal calorimetry. By these methods, compounds of this invention can be shown to bind to IL-2 with one-to-one stoichiometry; furthermore, compounds can be shown to bind at the IL-2 surface that is used to bind IL-2Rα.

Cell-based assays to study inhibition of IL-2/IL-2Rα binding use phosphorylation of STAT5 as a marker of IL-2 activity on CTLL-2 cells. When IL-2 binds to its receptor, an intracellular signal is transduced from Jak1 and Jak3 proteins to STAT5. Phosphorylated STAT5 then translocates to the nucleus and activates transcription. Inhibition of STAT5 phosphorylation therefore indicates that the compounds interfere with IL-2 mediated signal transduction. For selectivity studies, one can monitor STAT5 phosphorylation in response to IL-15 binding. IL-15 is homologous to IL-2 and signals through the IL-2 dimeric receptor. IL-15 does not bind to IL-2Rα, and selective IL-2 inhibitors should not inhibit IL-15 signaling. A description of the assay is given in Example 78.

The activity of compounds of this invention can be measured in vivo by activity against animal models of the selected disease.

The therapeutic ratio of a compound can be determined for a selected disease, for example, by comparing the dose that gives effective activity in a suitable in vivo model in a suitable animal species, with the dose that gives significant weight loss (or other observable side-effects) in the test animal species.

Pharmaceutical Compositions and Administration

In general, compounds of this invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease, its severity, the age and relative health of the animal being treated, the potency of the compound(s), and other factors. A representative dose will range from 0.001 to 100 milligrams per kilogram body weight of the animal per day(mg/Kg/day); for example, from 0.01 to 10 mg/Kg/day. A person of ordinary skill in the art will be able without undue experimentation, having regard to that skill and this disclosure, to determine a therapeutically effective amount of a compound of this invention for a given disease.

In general, compounds of this invention will be administered as pharmaceutical compositions by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Gennaro, ed., "Remington: The Science and Practice of Pharmacy", 20th ed., 2000, Lippincott, Williams & Wilkins, Philadelphia, Pa. Suitable liquid carriers, especially for injectable solutions, include water, aqueous saline solution, aqueous dextrose solution, and glycols.

The amount of a compound of this invention in the composition may vary widely depending on the type of composition, size of a unit dosage, kind of excipients, and other factors well known to those of ordinary skill in the art. In general, the final composition may comprise from 0.001 percent by weight (% w) to 90% w of the compound of this invention, preferably 0.01% w to 10% w, with the remainder being the excipient or excipients.

A pharmaceutical composition of this invention may optionally contain, in addition to a compound of this invention, at least one other compound of this invention, and/or at least one pharmaceutically active compound selected from compounds conventionally used in the treatment of the selected disease. For example, in the case of allograft rejection, the composition may contain one or more of the conventional immunosuppressants mentioned in the BACKGROUND TO THE INVENTION.

Additionally, compounds conventionally used in the treatment of the selected disease may also be co-administered with compound(s) of this invention. "Co-administered" here includes administration during the course of treatment with the compound(s) of this invention, and is not limited to administration at the same time as the administration of the compound(s) of this invention, depending on appropriate dosing schedules for the conventional compounds and for the compound(s) of this invention.

Preparation of the Compounds of This Invention

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser, "Reagents for Organic Synthesis", vols 1–17, 1991, John Wiley and Sons, New York, N.Y.; Rodd, "Chemistry of Carbon Compounds", vols. 1–5 and supps, 1989, Elsevier Science Publishers; "Organic Reactions", vols 1–40, 1991, John Wiley and Sons, New York, N.Y.; March, "Advanced Organic Chemistry", 4th ed., 1992, John Wiley and Sons, New York, N.Y.; and Larock, "Comprehensive Organic Transformations", 1989, VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Unless specified to the contrary, the reactions described herein take place at atmospheric pressure over a temperature range between about 0° C. and 125° C.

The preparation of the core of the compounds of formula I may be accomplished by methods similar to those seen in Examples 16 and other like examples; i.e. as in Scheme I below, where substituents and variations in ring size of the compound of formula I have been omitted for clarity.

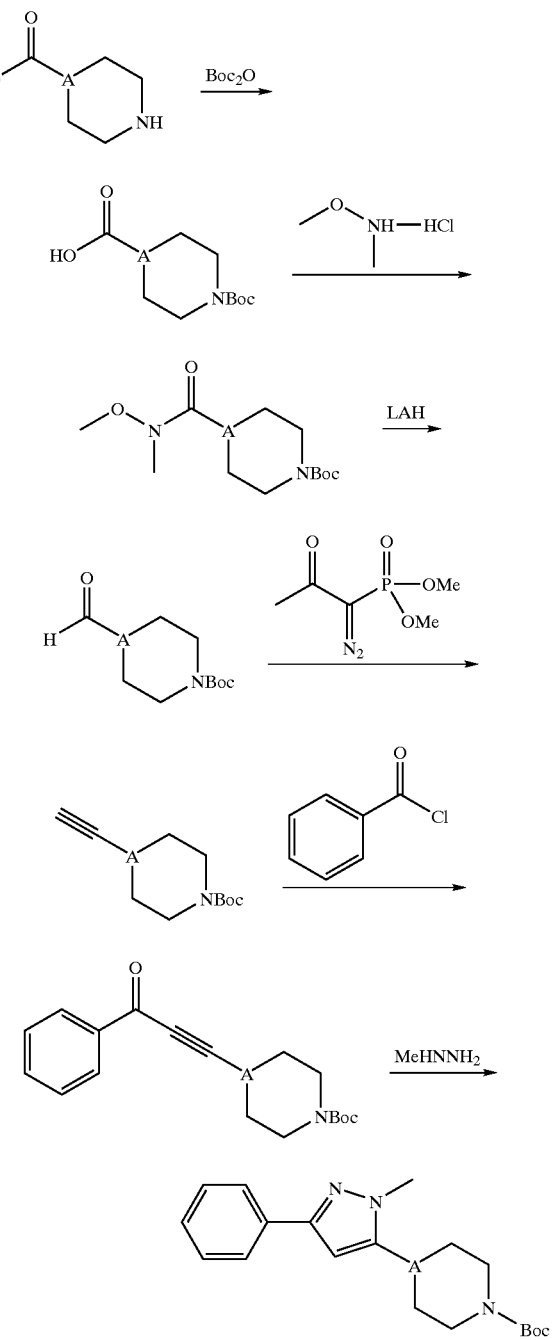

Scheme I

As seen in Scheme I, above, a piperidine or piperazine carboxylic acid is protected at the nitrogen, then reacted with dimethylhydroxylamine, followed by reduction with an agent such as lithium aluminum hydride to form the corresponding aldehyde, then treated with a reagent such as dimethyl 1-diazo-2-oxopropylphosphonate to convert the aldehyde into an acetylene. Reaction of the acetylene with an aryl chloride gives an arylacetylene, and this is reacted with an alkylhydrazine to form the imidazole center ring. The resulting compound can be deprotected in the conventional manner.

Elaboration of the aryl group can be accomplished by a variety of methods shown in Scheme II:

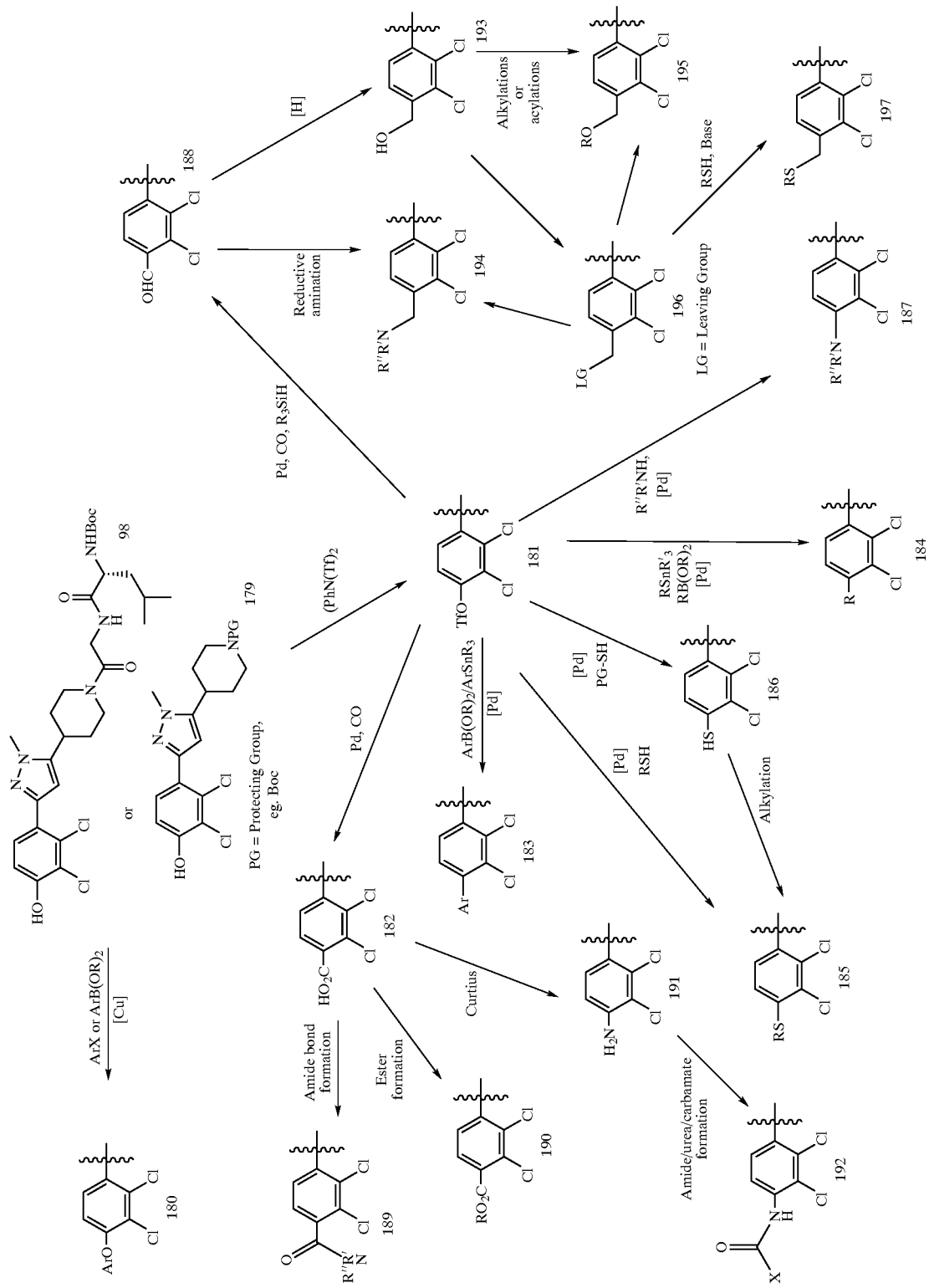

The phenols 98 and 179 can be used to prepare biaryl ether type analogues 180 using, for example, Ullman type couplings as described by, for example, Evans et al., *Tetrahedron Lett.* 1998, 39, 2937–2940, *J. Am. Chem. Soc.* 1997, 119, 3395–3396, *J. Am. Chem. Soc.* 1997, 119, 10539–10540, and *Tetrahedron Lett.* 1998, 39, 2933–2936). Compounds 98 and 179 may also be used to make the corresponding trifluoromethanesulfonyloxy intermediate 181, using, for example, N-phenyltrifluoromethansulfonimide in the presence of a base such as triethylamine. The triflated phenol 181 is a valuable precursor since it may be used in various palladium-catalyzed transformations to provide further intermediates/analogues such as the carboxylic acid 182 (via palladium-catalyzed carbonylation using carbon monoxide, see, for example, *Tetrahedron Lett.* 1992, 33, 3939–3942), biaryls, arylvinyls, and arylalkyls 183 and 184 (via Suzuki/Stille/Heck couplings). Compound 181 may also be used to prepare aryl sulfides such as 185 and 186 (see, for example, Nan Zheng et al., *J. Org. Chem.* 1998, 63, 9606–9607.). Further, triflated phenols such as 181 can be used as substrates for the preparation of substituted aromatic amines such as 187 using conditions developed by, for example, Buchwald (see, for example, *J. Org. Chem.* 2000, 65, 1158–1174, and references therein). In addition, triflate 181 may be converted to the corresponding aldehyde, 188, using palladium catalysis under a carbon monoxide atmosphere in the presence of a reducing agent such as a trialkylsilane.

Carboxylic acid 182 can be used to make amides such as 189 and esters such as 190. In addition, compound 182 can be subjected to a Curtius rearrangement to provide the aniline 191 which in turn may be converted to amides, ureas, and carbamates 192.

The aromatic aldehyde 188 can be reduced to the corresponding benzylic alcohol 193 or subjected to reductive amination to furnish benzylic amines such as 194. The alcohol 193 may be alkylated or converted to esters to yield compounds such as 195. It may also be converted to an alkylating agent such 196 (for example, a benzylic bromide) which in turn can be used to provide benzylic thiols such as 197.

Elaboration of the —B—J—M portion of the molecule may be accomplished by the methods generally described in Examples 1 through 76, and as illustrated in Scheme II

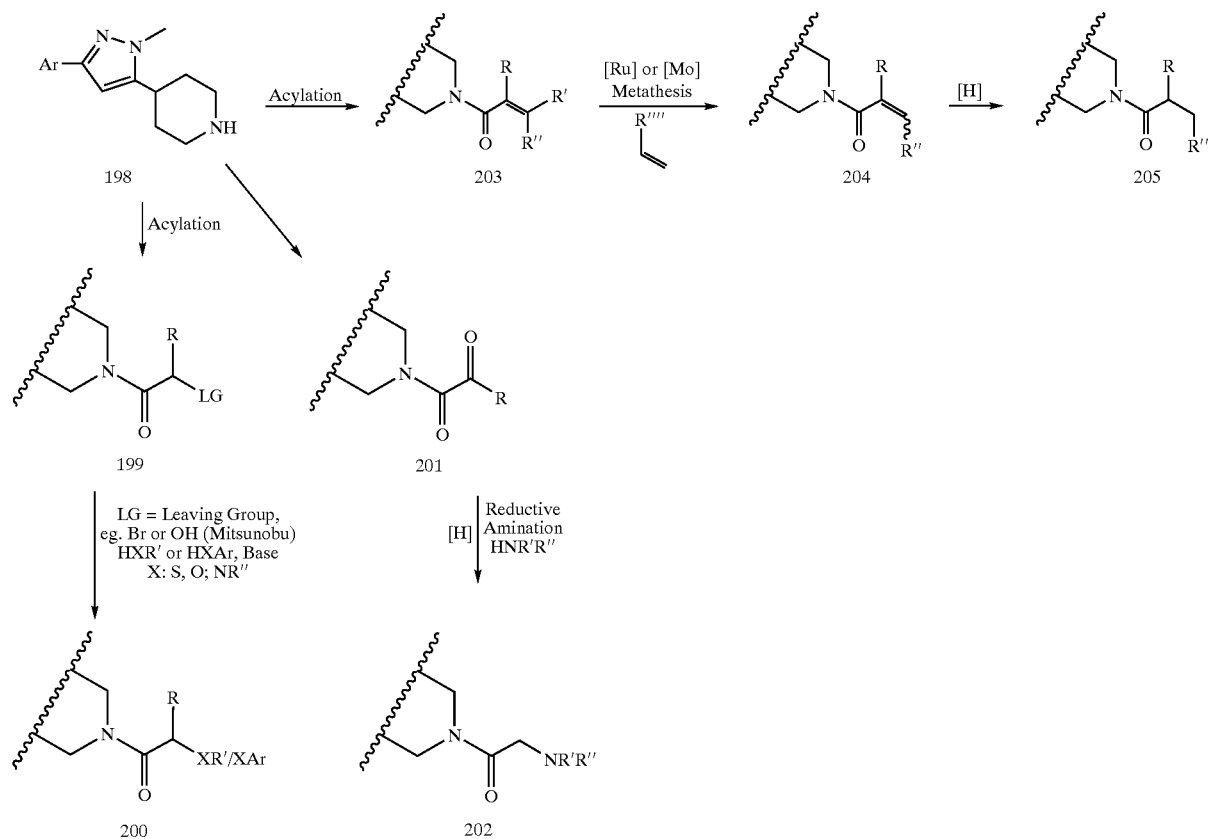

Scheme III

Referring to Scheme III above, the piperidine derivative 198 (e.g. 25) can be reacted with acylating agents containing a leaving group (e.g., bromine) at, for example, the ω-position to provide alkylating agents such as 199. These alkylating agents may be reacted further with nucleophiles, such as amines or alcohols, to provide compounds (200) with a linkage to a guanidine-like fragment or a guanidine mimetic. Compound 198 may also be acylated to provide α-diketo derivatives such as 201. These compounds may be used in reductive aminations to provide additional linked guanidine type compounds 202. Alternatively, 198 can be acylated to provide acrylic derivatives such as 203, which can be used in a cross-metathesis transformation (for a review and leading references, see: *Tetrahedron* 1998, 39, 2805), yielding compounds 204 which may be further manipulated (reduced) to analogues such as 205.

The preparation of compounds of formula I'

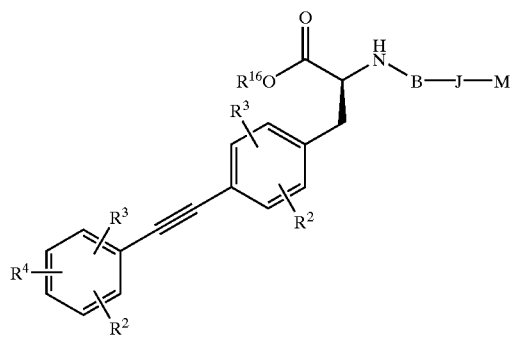

is accomplished generally by the method of Tilley et al., *J. Am. Chem. Soc.* 1997, 119, 7589–7590 and its supplemental materials, and Tilley et al., *J. Org. Chem.* 1995, 55, 906–910, i.e.;

the 4-trifluoromethanesulfonyloxy compound. This is reacted with an optionally ring-substituted phenylacetylene in the presence of a palladium catalyst, and the amine deprotected with acid. Elaboration of the amine to form the compounds of formula I' proceeds in the same manner as for the compounds of formula I. It is assumed in this scheme that $R^{16}$ is not hydrogen or acetylamino-$C_1$–$C_{12}$alkyl; if $R^{16}$ is desired to be either of these, then the scheme may be carried through using as $R^{16}$ a protecting group which is removed by hydrolysis at the appropriate point in the synthesis to give the compound of formula I' where $R^{16}$ is hydrogen, and optionally then treated to give the appropriate N-alkylcarbamate.

The syntheses are illustrated generally in the following Examples 1–76.

Other methods of synthesis are also usable, and a person of ordinary skill in the art, having regard to that skill, this disclosure, and the references cited herein, will be able to prepare desired compounds of this invention without undue experimentation.

EXAMPLES

The following non-limiting examples illustrate the invention. All commercially available materials were used as received. All synthesized compounds were characterized by $^1$H NMR (Bruker DMX 400 MHz spectrometer) and/or electrospray mass-spectroscopy (ES (+) MS, Hewlett-

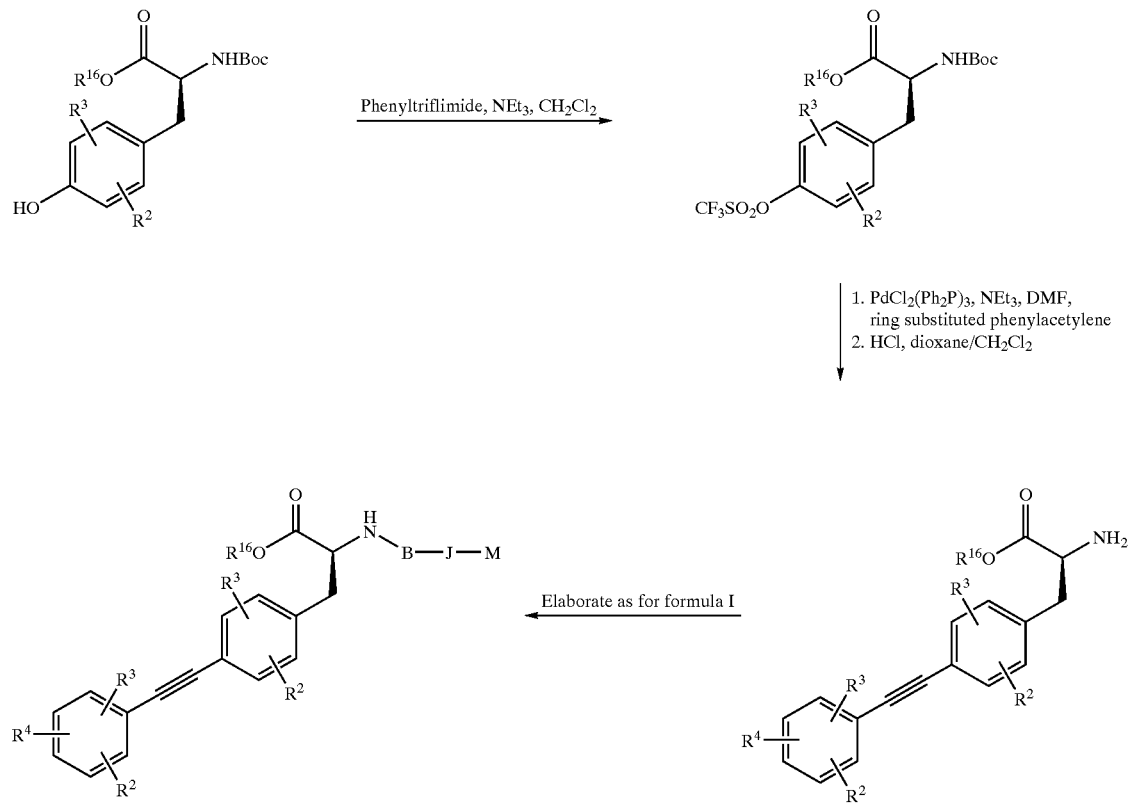

An optionally ring-substituted tyrosine is protected at the amine nitrogen, then treated with phenyltriflimide to give Packard Series 1100 MSD). Abbreviations for reagents and methods are those conventional in the art.

Example 1

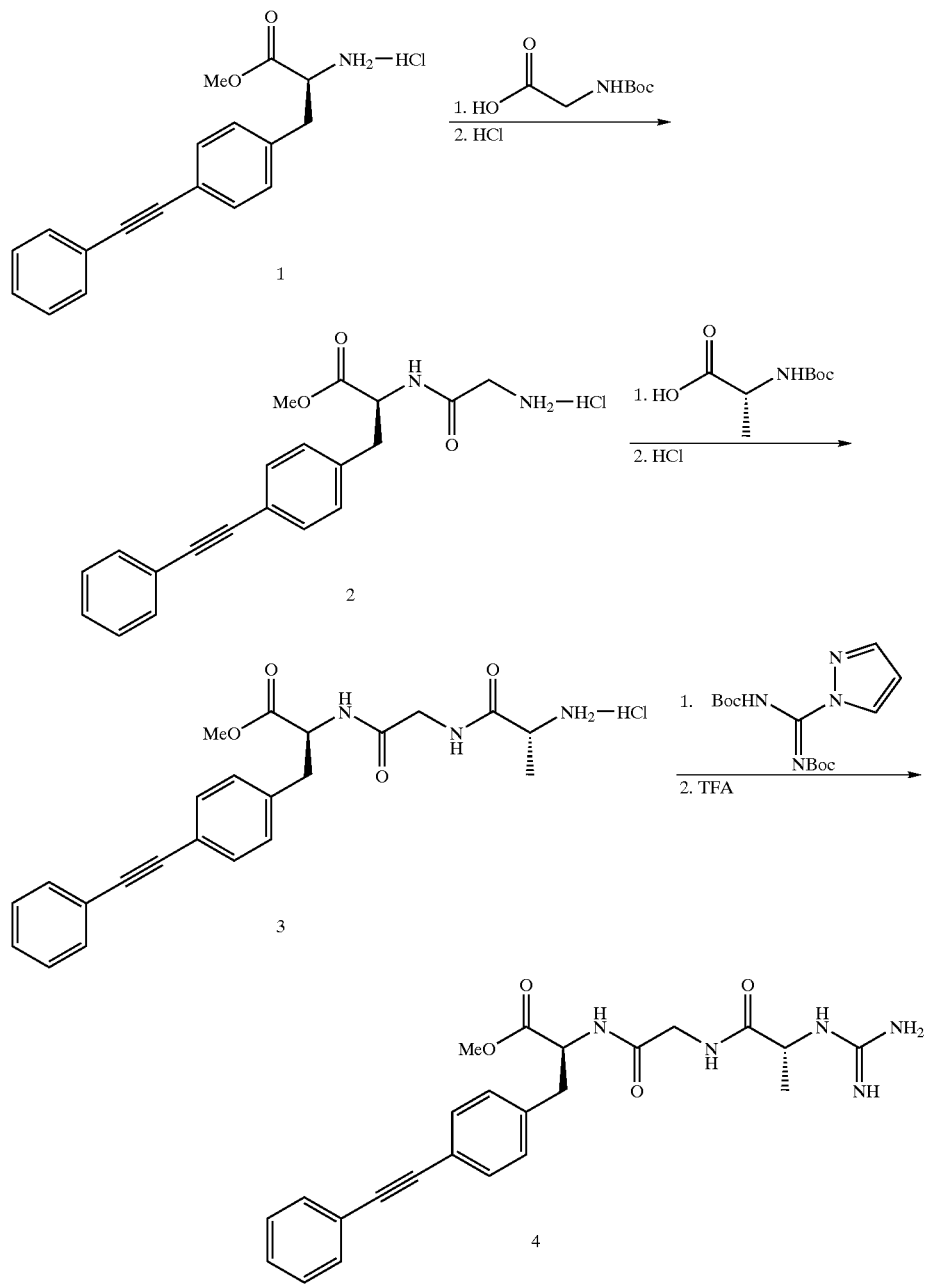

Amine HCl salt 1 was prepared according to the method of Tilley et al., *J. Am. Chem. Soc.* 1997, 119, 7589–7590 and its supplemental materials, and Tilley et al., *J. Org. Chem.* 1995, 55, 906–910.

a) To a solution of 1 (0.25 g, 0.8 mmol) in dichloromethane (6 mL) was added N-Boc-glycine (0.18 g, 1.0 mmol), EDC (0.19 g, 1.0 mmol), HOBt (0.15 g, 1.0 mmol), and triethylamine (0.28 mL, 2.0 mmol). The mixture was stirred overnight and then was partitioned between dichloromethane and water. The aqueous layer was washed with dichloromethane (2×); the organic layer was washed with 1M HCl and saturated $NaHCO_3$. The organic layer was dried over $Na_2SO_4$, filtered, and concentrated in vacuo to provide the desired amide.

The crude residue was dissolved in HCl/dioxane (4.0N, 5 mL), stirred for 45 minutes, and then concentrated in vacuo to provide 2.

b) To a solution of 2 (0.1 g, 0.27 mmol) in dichloromethane (2 mL) was added N-Boc-D-alanine (66 mg, 0.35 mmol), EDC (67 mg, 0.35 mmol), HOBt (53 mg, 0.35 mmol), and triethylamine (0.1 mL, 0.7 mmol). The mixture was stirred overnight and then was partitioned between dichloromethane and water. The aqueous layer was washed with dichloromethane; the organic layer was washed with 1M HCl and saturated $NaHCO_3$. The organic layer was dried over $Na_2SO_4$, filtered, and concentrated in vacuo to provide the desired amide.

The crude residue was dissolved in HCl/dioxane (4.0N, 5 mL), stirred for 30 minutes, and then concentrated in vacuo to provide 3 (110 mg).

c) To a solution of 3 (75 mg, 0.17 mmol) in MeOH (2.5 mL) was added (tert-butoxycarbonylimino-pyrazol-1-yl-methyl)-carbamic acid tert-butyl ester (77 mg, 0.25 mmol) and triethylamine (45 μL, 0.32 mmol). The mixture was stirred overnight and then was partitioned between dichloromethane and water. The aqueous layer was washed with dichloromethane (2×); the organic layer was washed with 1M HCl, dried over Na$_2$SO$_4$, filtered, and concentrated in vacuo.

The residue was dissolved in dichloromethane (1.5 mL) and TFA (1.5 mL) was added. The solution was stirred for 2 h and then concentrated to an oil. Purification of the material by RP HPLC to provide 4 as a white solid. ES (+) MS m/e=450 (M+1).

Example 2

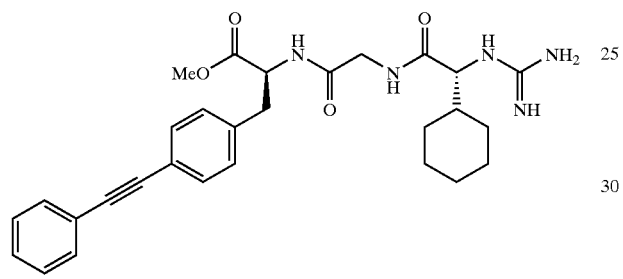

Title compound 5 was prepared according to the procedure of Example 1a–c except for using N-Boc-D-cyclohexylglycine as a reagent instead of N-Boc-D-alanine. ES (+) MS m/e=518 (M+1).

Example 3

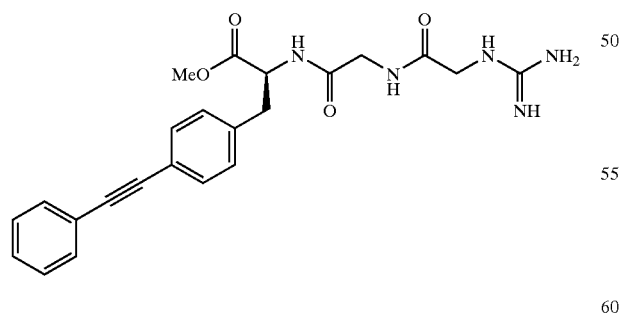

Title compound 6 was prepared according to the procedure of Example 1a–c except for using N-Boc-glycine as a reagent instead of N-Boc-D-alanine. ES (+) MS m/e=436 (M+1).

Example 4

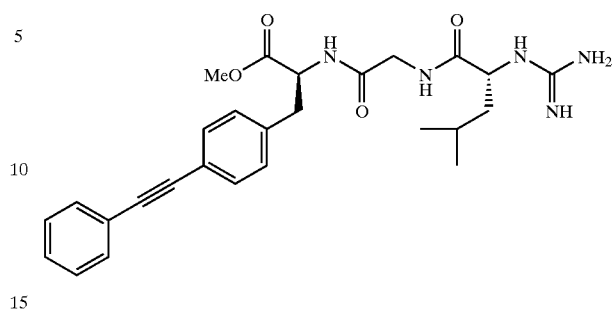

Title compound 7 was prepared according to the procedure of Example 1a–c except for using N-Boc-D-leucine as a reagent instead of N-Boc-D-alanine. ES (+) MS m/e=492 (M+1).

Example 5

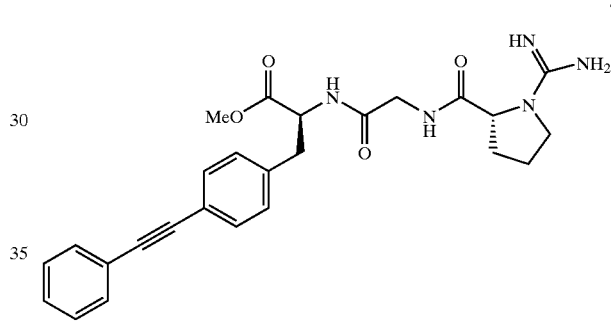

Title compound 8 was prepared according to the procedure of Example 1a–c except for using N-Boc-D-proline as a reagent instead of N-Boc-D-alanine. ES (+) MS m/e=476 (M+1).

Example 6

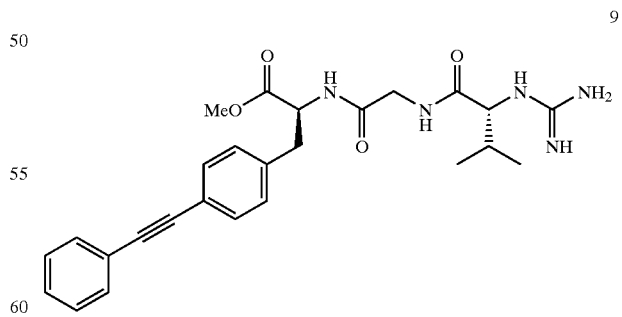

Title compound 9 was prepared according to the procedure of Example 1a–c except for using N-Boc-D-valine as a reagent instead of N-Boc-D-alanine. ES (+) MS m/e=478 (M+1).

Example 7

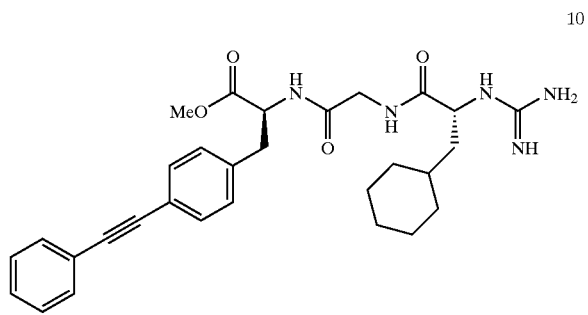

10

Title compound 10 was prepared according to the procedure of Example 1a–c except for using N-Boc-D-cyclohexylalanine as a reagent instead of N-Boc-D-alanine. ES (+) MS m/e=532 (M+1).

Example 8

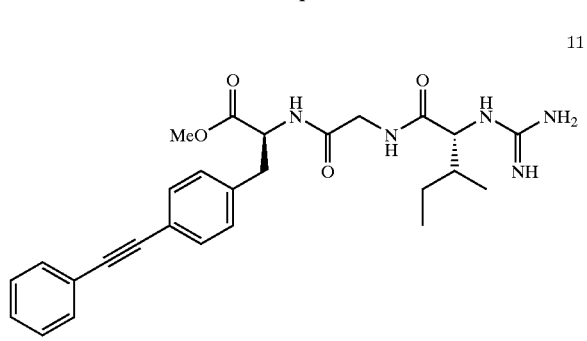

11

Title compound 11 was prepared according to the procedure of Example 1a–c except for using N-Boc-D-isoleucine as a reagent instead of N-Boc-D-alanine. ES (+) MS m/e= 492 (M+1).

Example 9

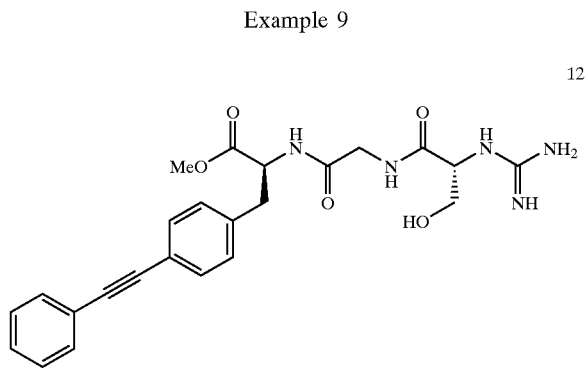

12

Title compound 12 was prepared according to the procedure of Example 1a–c except for using N-Boc-D-serine as a reagent instead of N-Boc-D-alanine. ES (+) MS m/e=466 (M+1).

Example 10

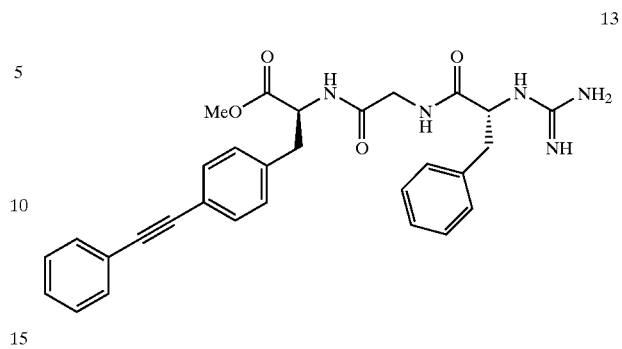

13

Title compound 13 was prepared according to the procedure of Example 1a–c except for using N-Boc-D-phenylalanine as a reagent instead of N-Boc-D-alanine. ES (+) MS m/e=526 (M+1).

Example 11

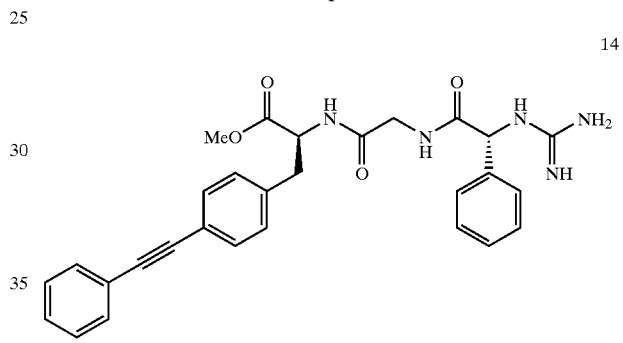

14

Title compound 14 was prepared according to the procedure of Example 1a–c except for using N-Boc-D-phenylglycine as a reagent instead of N-Boc-D-alanine. ES (+) MS m/e=512 (M+1).

Example 12

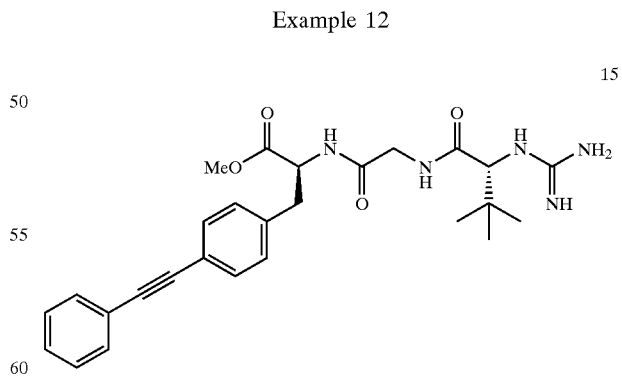

15

Title compound 15 was prepared according to the procedure of Example 1a–c except for using N-Boc-D-tert-butylglycine as a reagent instead of N-Boc-glycine. ES (+) MS m/e=492 (M+1).

Example 13

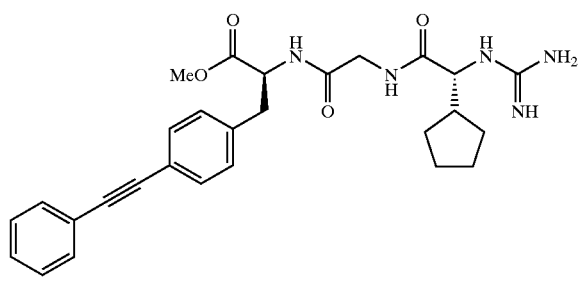

Title compound 16 was prepared according to the procedure of Example 1a–c except for using N-Boc-cyclopentylglycine as a reagent instead of N-Boc-glycine. ES (+) MS m/e=504 (M+1).

Example 14

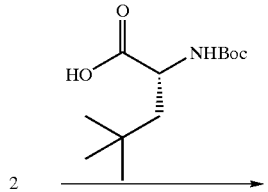

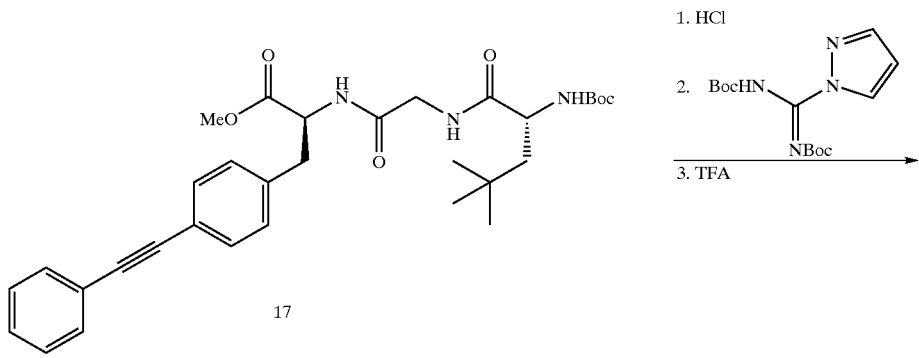

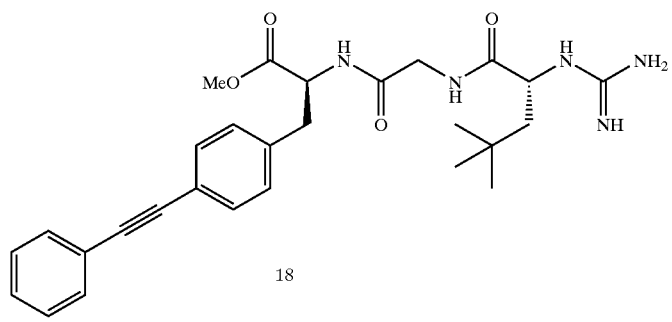

a) To a solution of 2 (0.48 g, 1.3 mmol) in dichloromethane (8 mL) was added N-Boc-D-t-butylalanine (0.39 g, 1.6 mmol), EDC (0.3 g, 1.6 mmol), HOBt (0.25 g, 1.6 mmol), and triethylamine (0.45 mL, 3.2 mmol). The mixture was stirred overnight and then was partitioned between dichloromethane and water. The aqueous layer was washed with dichloromethane; the organic layer was washed with 1M HCl and sat. NaHCO$_3$. The organic layer was dried over Na$_2$SO$_4$, filtered, and concentrated in vacuo to provide 17 (0.67 g).

b) Amide 17 (~0.2 mmol) was dissolved in HCl/dioxane (4.0N, 5 mL), stirred for 2 h, and then concentrated in vacuo.

To the crude HCl salt in MeOH (1 mL) was added (tert-butoxycarbonylimino-pyrazol-1-yl-methyl)-carbamic acid tert-butyl ester (93 mg, 0.3 mmol) and triethylamine (84 μL, 0.6 mmol). The reaction was stirred for 40 h and then concentrated in vacuo.

The dry residue was dissolved in dichloromethane (1.5 mL) and TFA (1.5 mL), stirred 3 h, and then concentrated to dryness. The material was purified by RP HPLC to provide 18 as a white solid. ES (+) MS m/e=506 (M+1).

Example 15

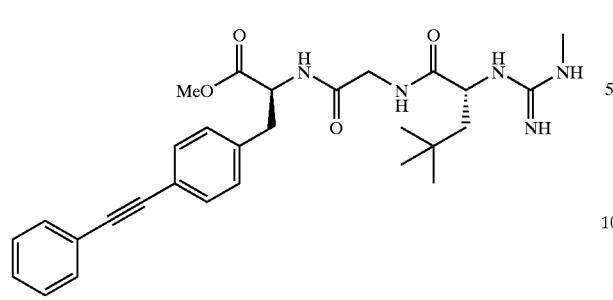

The title compound was prepared according to the procedure of Example 14 except for using (tert-butoxycarbonylimino-pyrazol-1-yl-methyl)-methylcarbamic acid tert-butyl ester as a reagent instead of (tert-butoxycarbonylimino-pyrazol-1-yl-methyl)-carbamic acid tert-butyl ester. ES (+) MS m/e=520 (M+1).

Example 16

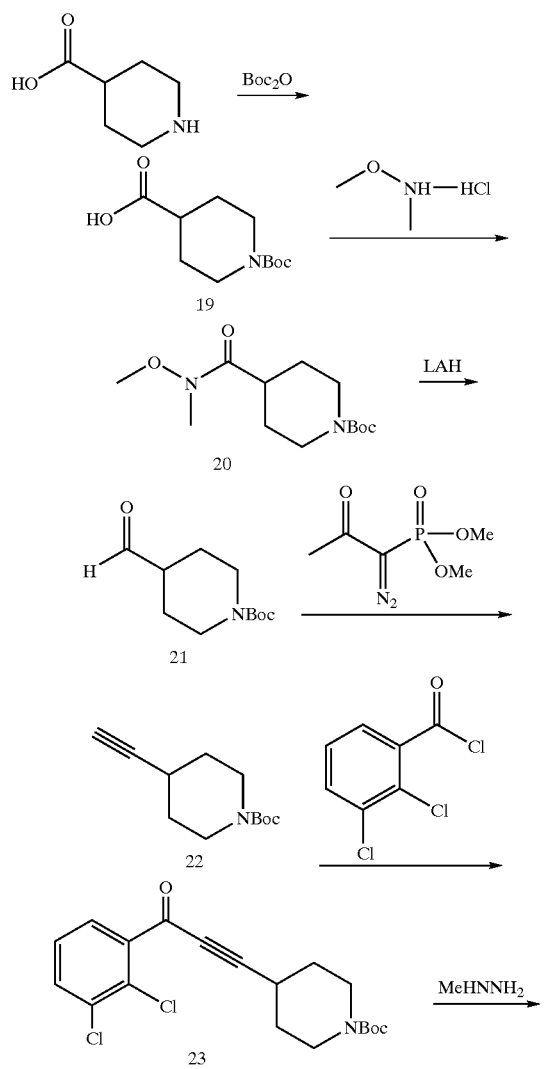

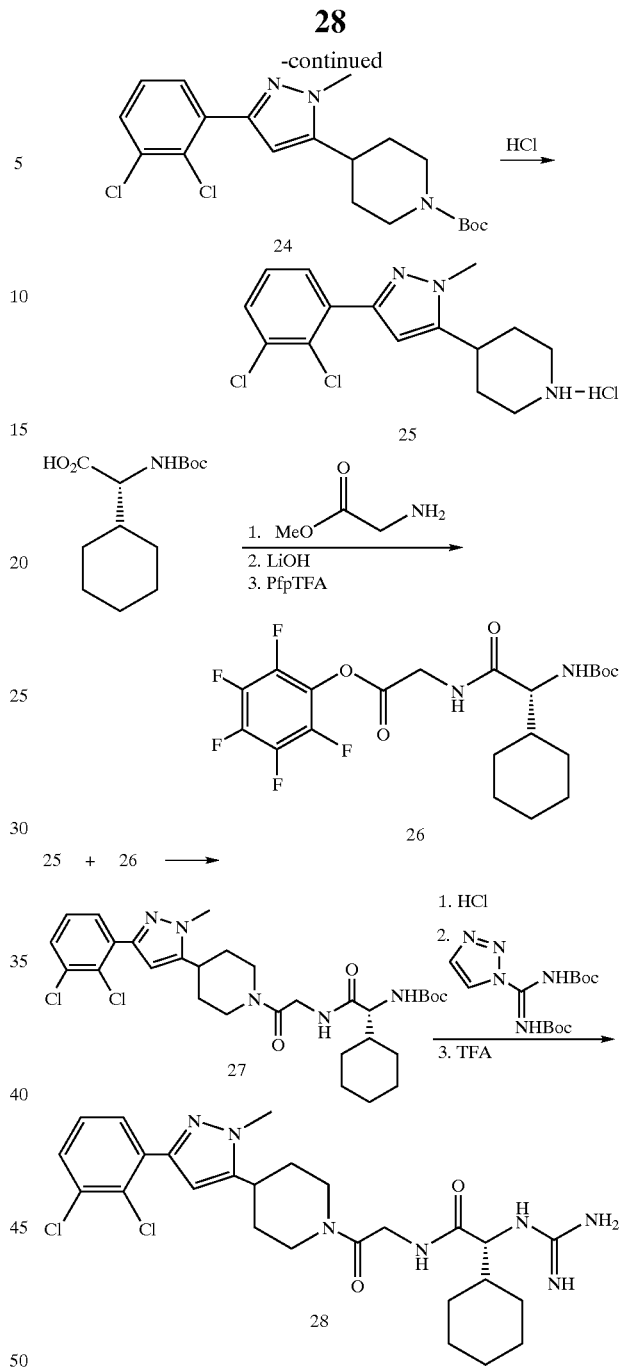

a) To a heterogeneous solution of isonipecotic acid (45.0 g, 0.35 mol), NaOH (41.8 g, 1.05 mol) in THF (350 mL) and water (650 mL) was added di-tert-butyl dicarbonate (91.3 g, 0.42 mol). The mixture was stirred overnight at room temperature and then diluted with ethyl acetate (500 mL). The resulting biphasic solution was separated and the basic aqueous layer was acidified to pH 2–3 by slow addition of concentrated HCl. The aqueous layer was washed with ethyl acetate (3×500 mL); the combined organic layer was dried over $MgSO_4$ and then concentrated under reduced pressure to afford 19 (76.9 g, 96%). $^1$H NMR ($CDCl_3$) δ1.45 (s, 9H), 1.59–1.64 (m, 2H), 1.89–1.92 (m, 2H), 2.46–2.48 (m, 1H), 2.82–2.88 (m, 2H), 4.01 (m, 2H).

b) To a solution containing 19 (76.9 g, 0.34 mol), HOBt (54.4 g, 0.40 mol), EDC (77.1 g, 0.40 mol), and triethylamine (160 mL, 1.14 mol) in dichloromethane (700 mL) was added N,O-dimethylhydroxylamine hydrochloride (39.3 g, 0.40 mol). The resulting mixture was stirred overnight at room temperature. The solution was partitioned between water and dichloromethane; the aqueous layer was washed with ethyl acetate (2×500 mL). The combined organic layer was washed with brine, dried over MgSO$_4$, and concentrated under reduced pressure to afford crude 20 (79.5 g, 87%). ES (+) MS m/e=217 (M−55).

c) To a solution of 20 (1.0 g, 3.7 mmol) in THF (8.0 mL) at −78° C. was added dropwise lithium aluminum hydride (1.0M in THF, 4.0 mL, 4.0 mmol). Upon complete addition, the reaction mixture was stirred for 15 minutes at −78° C. The reaction was quenched by slow addition of isopropanol followed by aqueous 1.0M HCl (50 mL). The aqueous layer was washed with ethyl acetate (3×50 mL). The combined organic layer was dried over MgSO$_4$ and concentrated under reduced pressure to afford crude 21 (0.8 g, 99%). ES (+) MS m/e=158 (M−55).

d) To a heterogeneous solution of 21 (23.7 g, 0.11 mol) and potassium carbonate (30.7 g, 0.22 mol) in MeOH (1.0 L) was added dropwise dimethyl-1-diazo-2-oxopropylphosphonate (21.3 g, 0.11 mol) [Muller et al., *Syn. Lett.*, 1996, 521] in MeOH (100 mL). The resulting mixture was stirred for 3 hours and concentrated under reduced pressure. The residue was diluted with diethyl ether (500 mL) and 5% aqueous NaHCO$_3$ (700 mL). The layers were separated and the aqueous layer was washed with diethyl ether (2×500 mL). The organic layer was dried over MgSO$_4$ and concentrated under reduced pressure to afford crude 22 (22.4 g, 96%). $^1$H NMR (CDCl$_3$) δ1.45 (s, 9H), 1.57–1.60 (m, 2H), 1.75–1.77 (m, 2H), 2.09 (s, 1H), 2.57–2.58 (m, 1H), 3.15–3.20 (m, 2H), 3.67 (m, 2H).

e) To a solution of 22 (22.4 g, 107 mmol), 2,3-dichlorobenzoyl chloride (22.4 g, 107 mmol), copper(I) iodide (1.0 g, 5.3 mmol), and triethylamine (15 mL, 107 mmol) in toluene (500 mL) was added dichlorobis(triphenylphosphine)palladium(II) (3.75 g, 5.3 mmol). The resulting mixture was stirred overnight and then diluted with saturated sodium bicarbonate (500 mL) and ethyl acetate (500 mL). The aqueous layer was washed with ethyl acetate (500 mL); the organic layer was washed with brine, dried over MgSO$_4$, and concentrated under reduced pressure. The residue was purified by flash chromatography (SiO$_2$: 25 to 50% ethyl acetate in hexanes) to afford 23 (31.9 g, 78%). ES (+) MS m/e=326 (M−55).

f) To a solution of 23 (31.9 g, 83.4 mmol) in ethanol (160 mL) at 0° C. was added methylhydrazine (8.9 mL, 167 mmol). The resulting mixture was stirred for 15 minutes at 0° C. and then concentrated under reduced pressure. Purification of the residue by flash chromatography (SiO$_2$: 25 to 50% ethyl acetate in hexanes) afforded 24 (16.0 g, 46%) as a pure regioisomer. Concentration of mixed fractions provided additional 24 (16.0 g, 46%) as a 9:1 mixture of regioisomers. ES (+) MS m/e=410 (M+1).

g) To a solution of 24 (16.0 g, 38.4 mmol) in dioxane (100 mL) was added HCl/dioxane (4.0N, 100 mL). The reaction mixture was stirred at room temperature for 1 hour and then was concentrated under reduced pressure to afford 25 (14.4 g, 99%). ES (+) MS m/e=310 (M+1).

h) To N-Boc-D-cyclohexylglycine (10.0 g, 38.9 mmol) in dichloromethane (100 mL) was added EDC (8.2 g, 42.8 mmol), HOBt monohydrate (6.5 g, 42.8 mmol) and triethylamine (11.9 mL, 85.5 mmol). Glycine methyl ester hydrochloride (5.8 g, 46.6 mmol) was added and the reaction mixture was stirred overnight at room temperature. The mixture was diluted with dichloromethane (60 mL) and partitioned with water (70 mL). The organic layer was separated, and the aqueous layer was extracted with dichloromethane (2×60 mL). The combined organic layer was washed with 1M HCl (60 mL), saturated NaHCO$_3$ (60 mL) and dried over Na$_2$SO$_4$. The solvent was removed under reduced pressure to afford the desired amide (12.0 g, 94%).

To the amide (12.0 g, 36.7 mmol) in THF/water (3:1, 150 mL) was added lithium hydroxide (2.0 g, 83.5 mmol). The reaction mixture was stirred at room temperature overnight and then acidified using 1 M HCl (100 mL). The mixture was extracted with ethyl acetate (3×100 mL) and the combined organic extracts were dried over Na$_2$SO$_4$ and concentrated in vacuo to yield the desired carboxylic acid (9.7 g, 84%).

To the acid (9.7 g, 30.9 mmol) in THF (120 mL) was added pyridine (2.8 mL, 34.0 mmol) and pentafluorophenyl trifluoroacetate (5.8 mL, 34.0 mmol). The reaction mixture was stirred at room temperature for 2 hours and then the solvent was removed under reduced pressure. The resulting residue was dissolved in ethyl acetate (100 mL) and was washed with 1M HCl (70 mL) and saturated NaHCO$_3$ (70 mL). The organic layer was dried over Na$_2$SO$_4$ and concentrated in vacuo to afford 26 (13.5 g, 91%). ES (+) MS m/e=425 (M−55).

To amine hydrochloride salt 25 (19 mg, 0.06 mmol) in dichloromethane (1 mL) with triethylamine (19 μL, 0.13 mmol) was added ester 26 (32 mg, 0.07 mmol). The reaction was stirred at room temperature for 3 h and then the solvent was removed under reduced pressure to yield 27 which was used without purification. ES (+) MS m/e=606 (M+1).

A solution of 27 (34 mg, 0.06 mmol) in HCl/dioxane (4N, 1 mL) was stirred at room temperature for 30 min. The solvent was removed under reduced pressure to provide the desired amine as the hydrochloride salt which was used without purification.

To the amine hydrochloride salt (30 mg, 0.06 mmol) in MeOH (1 mL) with triethylamine (23 μL, 0.17 mmol) was added N,N'-bis-Boc-1-guanylpyrazole (26 mg, 0.08 mmol). The reaction mixture was stirred at room temperature overnight. The solvent was removed under reduced pressure to yield the protected guanidine which was used without purification.

The protected guanidine (42 mg, 0.06 mmol) was dissolved in TFA/dichloromethane (1:1, 1 mL) and stirred at room temperature for 3 h. The solvent was removed under reduced pressure to afford the crude guanidine as the trifluoroacetate salt. The crude material was purified by RP HPLC to provide 28. ES (+)MS m/e=548 (M+1).

Example 17

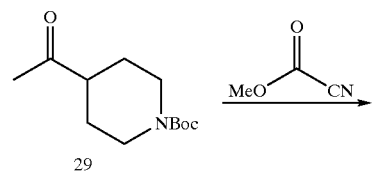

29

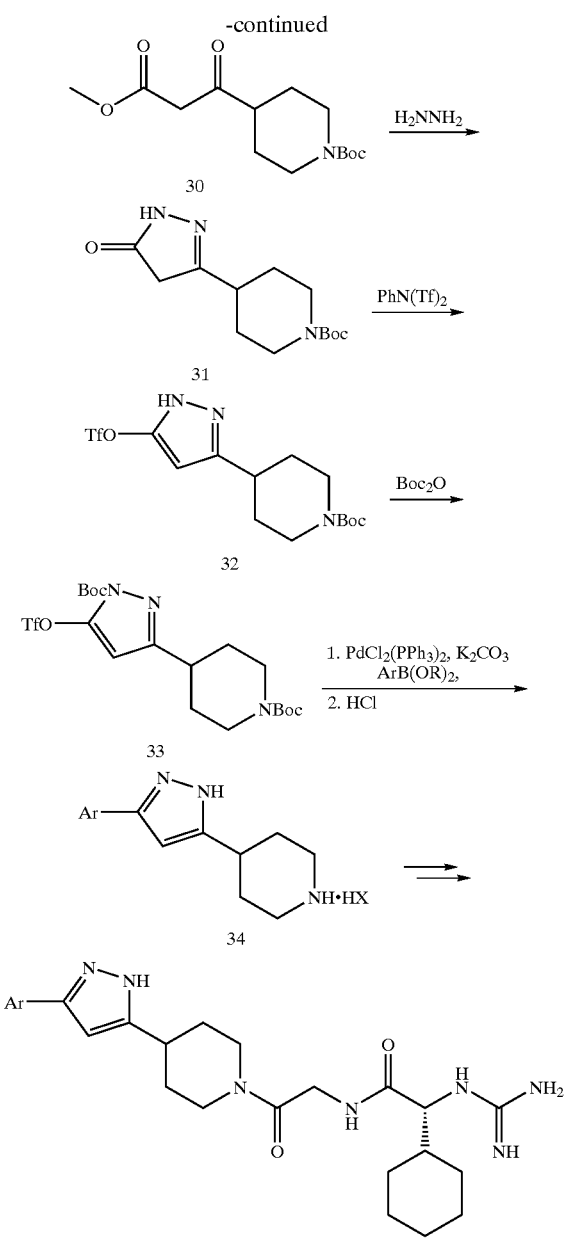

a) To a solution of 29 (25 g, 110 mmol) in THF (435 mL) at −78° C. was added dropwise lithium bis(trimethylsilyl) amide (1.0M in THF, 220 mL, 220 mmol). To the resulting mixture was added methyl cyanoformate (15.7 mL, 198 mmol). After 30 minutes at −78° C., the reaction was warmed to room temperature, diluted with diethyl ether, and then quenched with water. The mixture was extracted with water, 0.5N aqueous HCl, and brine. The organic layer was dried over $Na_2SO_4$ and concentrated to yield 30 (33.4 g) as a colorless oil. A pure sample was obtained by flash column chromatography ($SiO_2$: gradient 0 to 40% ethyl acetate in hexane). $^1$H NMR (400 MHz, $CDCl_3$) δ4.10 (br s, 2H), 3.73 (s, 3H), 3.50 (s, 2H), 2.77 (m, 2H), 2.60 (m, 1H), 1.83 (m, 2H), 1.57 (m, 2H), 1.44 (s, 9H); TLC ($SiO_2$: 20% ethyl acetate in hexane): $R_f$=0.13, TLC ($SiO_2$; 50% ethyl acetate in hexane): $R_f$=0.34; ES (+) MS m/e=286 (M+1).

b) A mixture of the crude product 30 (32.8 g) obtained in the previous step and hydrazine hydrate (5.58 mL, 115 mmol) in ethanol (120 mL) was heated at 70° C. until TLC indicated complete consumption of the starting material (~1 h). The reaction was cooled to ambient temperature and the resulting precipitate (11.5 g of 31) was collected by filtration. The filtrate was concentrated, re-dissolved in hot ethanol, and allowed to reach room temperature. After standing for several hours a second crop of 31 (4.3 g) was collected and when combined provided 31 (15.8 g, 54% from 29) as an off-white solid. $^1$H NMR (400 MHz, $CD_3OD$) δ4.11 (m, 2H), 3.30 (m, 1H), 2.86 (br s, 2H), 2.73 (m, 2H), 1.88 (m, 2H), 1.53 (m, 2H), 1.46 (s, 9H); TLC ($SiO_2$: 10% methanol in dichloromethane): $R_f$=0.27; ES (+) MS m/e=268 (M+1).

c) A solution of 31 (11.5 g, 43.0 mmol) and N-phenyltrifluoromethanesulfonimide (19.9 g, 55.9 mmol) in anhydrous dichloromethane (150 mL) under nitrogen at 0° C. was treated with triethylamine (60 mL, 430 mmol). The mixture was allowed to reach ambient temperature. After 1 h, HPLC indicated complete consumption of 31 and the solvent was removed under reduced pressure. Purification of the crude residue by flash column chromatography ($SiO_2$: gradient 0 to 40% ethyl acetate in hexane) yielded 32 (14.8 g, 86%) as a white solid. $^1$H NMR (400 MHz, $CDCl_3$) δ5.95 (s, 1H), 4.13 (br s, 2H), 2.82 (m, 3H), 1.94 (m, 2H), 1.61 (m, 2H), 1.46 (s, 9H); TLC ($SiO_2$; 50% ethyl acetate in hexane): $R_f$=0.45; ES (+) MS m/e=400 (M+1).

d) To a solution of 32 (14.8 g, 36.9 mmol) in dichloromethane (35 mL) was added a mixture of di-tert-butyl dicarbonate (12.1 g, 55.6 mmol), DMAP (0.45 g, 3.71 mmol), and triethylamine (75 mL) in dichloromethane (70 mL). After 1 h, HPLC indicated complete conversion of the starting material. The solvent was removed under reduced pressure and the crude residue was purified by flash column chromatography ($SiO_2$: gradient 0 to 10% ethyl acetate in hexane) to yield 33 (16.9 g, 91%) as a white solid. $^1$H NMR (400 MHz, $CDCl_3$) δ6.08 (s, 1H), 4.23 (br s, 2H), 3.47 (m, 1H), 2.81 (m, 2H), 2.00 (m, 2H), 1.64 (s, 9H), 1.49 (m, 2H), 1.47 (s, 9H); TLC ($SiO_2$: 20% ethyl acetate in hexane): $R_f$=0.36; ES (+) MS m/e=344 (M−156).

e) Suzuki couplings with 33.

General Procedure A: In a typical procedure aqueous potassium carbonate (2M, 200 mol %) was added to a solution of 33 (1M, 100 mol %, 0.2–0.4 mmol) and the arylboronic acid (110 mol %) in DMF/dioxane (2.5:1). The resulting solution was heated to 110° C. followed by addition of $PdCl_2(PPh_3)_2$ (10 mol %). The reaction was monitored by HPLC and allowed to cool to room temperature when 33 had been completely consumed. The mixture was filtered through a plug of Celite filter aid and concentrated. The residue was dissolved in dichloromethane (0.5 mL) and treated with HCl/dioxanes (4N, 4 mL) for 1 h. After removal of the solvent under reduced pressure, the crude residue was purified by RP HPLC to yield the corresponding 4-(5-aryl-pyrazol-3-yl)-piperidine trifluoroacetic acid salt 34.

General Procedure B: The Suzuki coupling was carried out as described in the general procedure A. The crude product was first purified by RP HPLC and then dissolved in dichloromethane (0.5 mL) and treated with HCl/dioxanes (4N, 4 mL) for 1 h. Removal of the solvent under reduced pressure yielded the corresponding 4-(5-aryl-pyrazol-3-yl)-piperidine hydrochloride salt 34.

General Procedure C: The Suzuki coupling was carried out as described in the general procedure A. The crude product was first purified by flash column chromatography and then dissolved in dichloromethane (0.5 mL) and treated with HCl/dioxane (4N, 4 mL) for 1 h. Removal of the solvent under reduced pressure yielded the corresponding 4-(5-aryl-pyrazol-3-yl)-piperidine hydrochloride salt 34.

Example 18

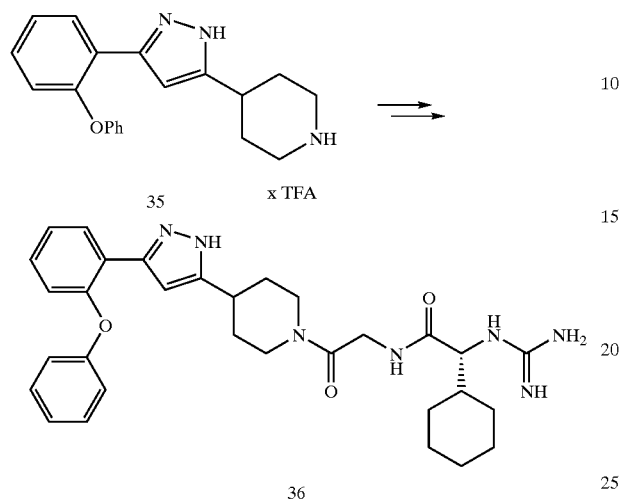

General Procedure A of Example 17e above was followed using 100 mg (0.20 mmol) of 33 and 4-phenoxyboronic acid to provide 35 (56 mg, 64%). ES (+) MS m/e=320 (M+1).

Title compound 36 was prepared according to the procedure of Example 16i,j except for using 35 as a reagent instead of 25. ES (+) MS m/e=558 (M+1).

Example 19

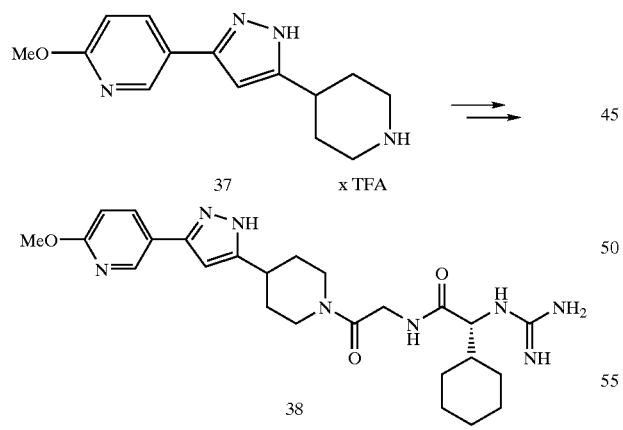

General Procedure A of Example 17e above was followed using 200 mg (0.40 mmol) of 33 and 2-methoxy-5-pyridineboronic acid to provide 37 (45 mg, 30%). ES (+) MS m/e=259 (M+1).

Title compound 38 was prepared according to the procedure of Example 16i,j except for using 37 as a reagent instead of 25. ES (+) MS m/e=497 (M+1).

Example 20

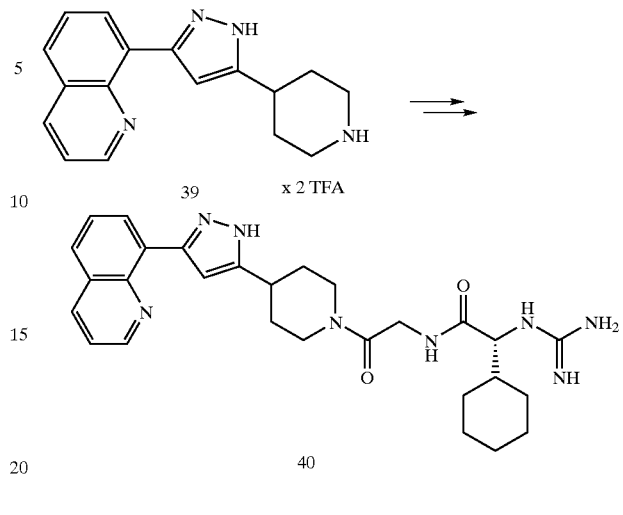

General Procedure A of Example 17e above was followed using 150 mg (0.30 mmol) of 33 and 8-quinolineboronic acid to provide 39 (48 mg, 32%). ES (+) MS m/e=279 (M+1).

Title compound 40 was prepared according to the procedure of Example 16i,j except for using 39 as a reagent instead of 25. ES (+) MS m/e=517 (M+1).

Example 21

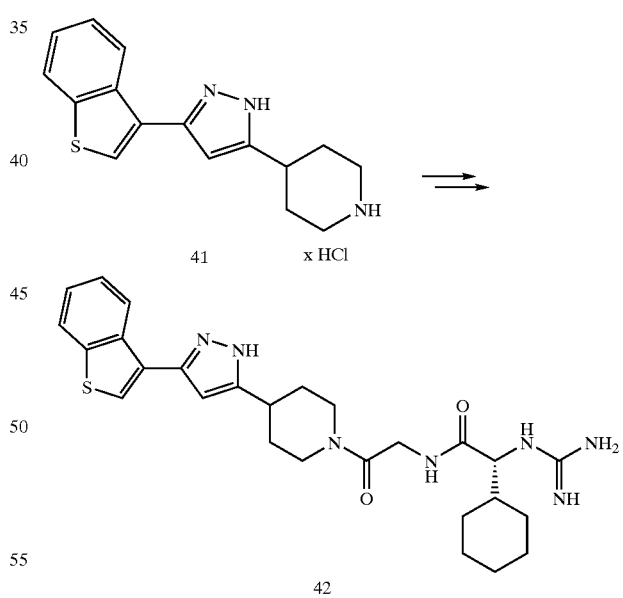

General Procedure B of Example 17e above was followed using 200 mg (0.40 mmol) of 33 and benzothiaphene-3-boronic acid to provide 41 (55 mg, 43%). ES (+) MS m/e=284 (M+1).

Title compound 42 was prepared according to the procedure of Example 16i,j except for using 41 as a reagent instead of 25. ES (+) MS m/e=522 (M+1).

Example 22

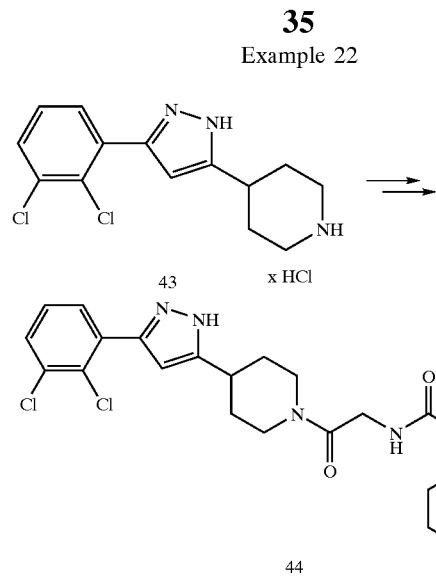

General Procedure B of Example 17e above was followed using 200 mg (0.40 mmol) of 33 and (2,3-dichlorophenyl) boronic acid to provide 43 (31 mg, 23%). ES (+) MS m/e=296 (M+1).

Title compound 44 was prepared according to the procedure of Example 16i,j except for using 43 as a reagent instead of 25. ES (+) MS m/e=534 (M+1).

Example 23

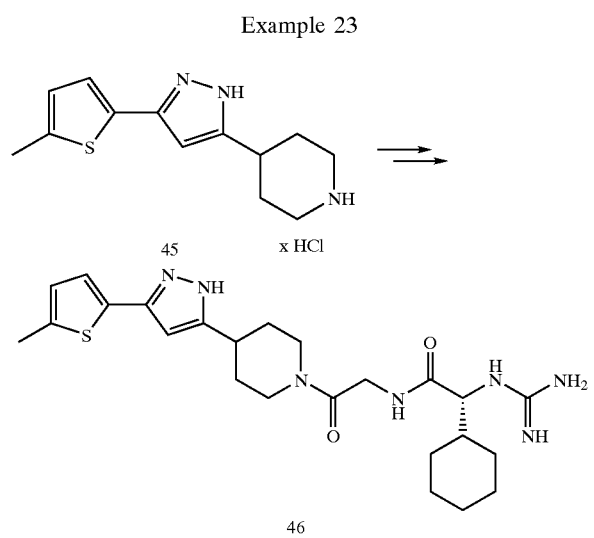

General Procedure B of Example 17e above was followed using 200 mg (0.40 mmol) of 33 and 5-methylthiophene-2-boronic acid to provide 45 (45 mg, 40%). ES (+) MS m/e=248 (M+1).

Title compound 46 was prepared according to the procedure of Example 16i,j except for using 45 as a reagent instead of 25. ES (+) MS m/e=486 (M+1).

Example 24

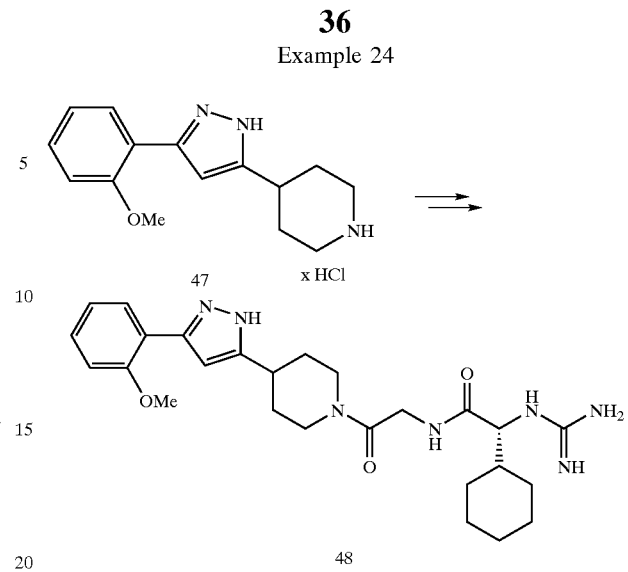

General Procedure C of Example 17e above was followed using 100 mg (0.20 mmol) of 33 and (2-methoxyphenyl) boronic acid to provide 47 (40 mg, 69%). ES (+) MS m/e=258 (M+1).

Title compound 48 was prepared according to the procedure of Example 16i,j except for using 47 as a reagent instead of 25. ES (+) MS m/e=496 (M+1).

Example 25

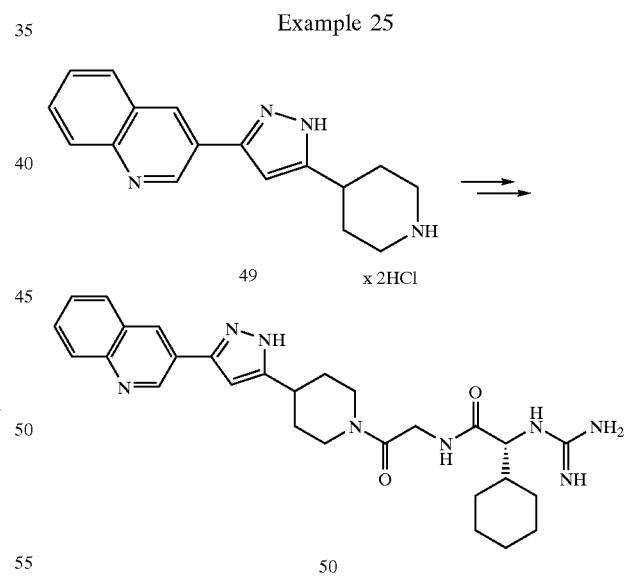

General Procedure C of Example 17e above was followed using 100 mg (0.20 mmol) of 33 and 3-quinolineboronic acid to provide 49 (61 mg, 87%). ES (+) MS m/e=279 (M+1).

Title compound 50 was prepared according to the procedure of Example 16i,j except for using 49 as a reagent instead of 25. ES (+) MS m/e=517 (M+1).

Example 26

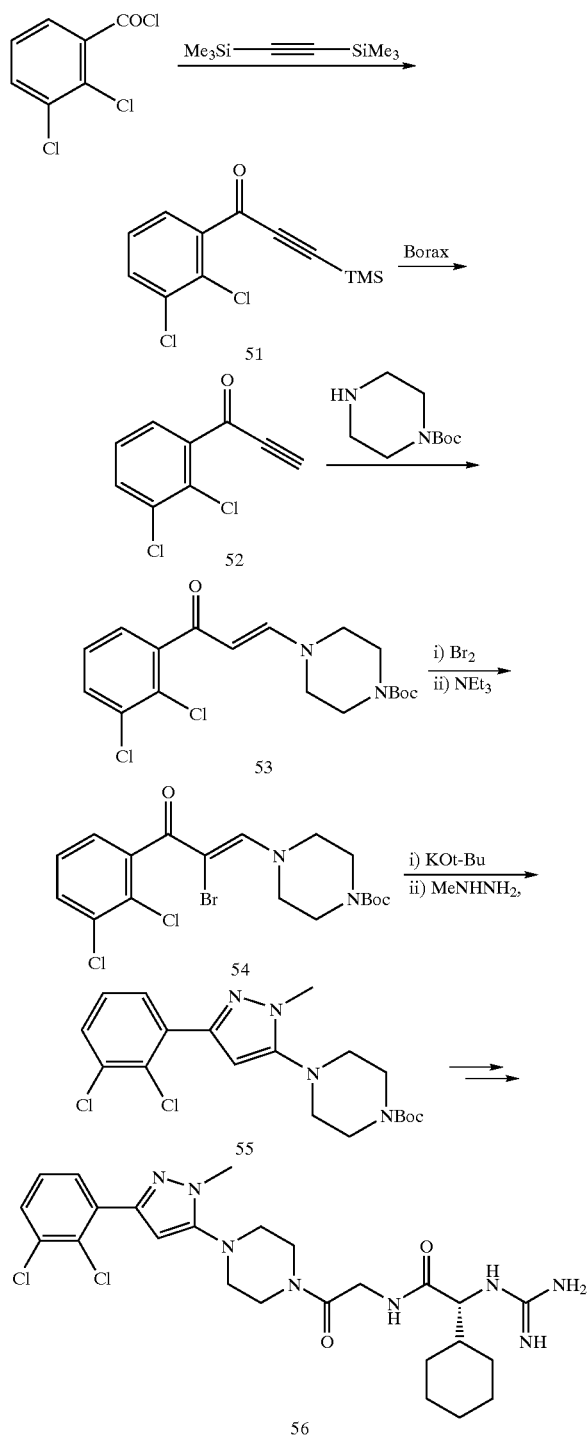

a) To a 0° C. solution of 2,3-dichloro-benzoyl chloride (10.0 g, 47.7 mmol) and bis(trimethylsilyl)acetylene (13.0 mL, 57.3 mmol) in anhydrous dichloromethane (240 mL) was added aluminum chloride (7.40 g, 55.8 mmol) portionwise. The resulting mixture was stirred under nitrogen at 0° C. for 1 h. The reaction mixture was poured into ice-water, the phases were separated, and the aqueous layer was extracted with dichloromethane (2×). The combined organic layer was washed with 5% aqueous NaHCO$_3$ (3×), dried (Na$_2$SO$_4$), and concentrated, avoiding heating. The residue was taken up in hexane, filtrated through a plug of silica gel, and concentrated, avoiding heating, to give 51 (11.9 g, 92%) as a colorless oil. $^1$H NMR (400 MHz, CDCl$_3$) δ7.85 (d, 1H, J=7.8 Hz), 7.64 (d, 1H, J=8.0 Hz), 7.33 (app t, 1H, J=7.9 Hz), 0.29 (s, 9H); TLC (SiO$_2$: 20% ethyl acetate in hexane): R$_f$=0.46; ES (+) MS m/e=271 (M+1).

b) To a mixture of 51 (11.9 g, 43.9 mmol) in THF/H$_2$O/MeOH (5:1:3, 90 mL) was added borax (353 mg, 1.76 mmol). The reaction was stirred at room temperature and closely monitored by TLC (SiO$_2$: 20% ethyl acetate in hexane). When almost all of 51 had been consumed (~15 minutes), ethyl acetate was added and the mixture was extracted with 1% aqueous citric acid. The phases were separated and the aqueous layer was extracted with ethyl acetate (2×). The combined organic layer was washed with brine, dried over Na$_2$SO$_4$, and concentrated. The residue was purified by flash column chromatography (SiO$_2$: gradient 0 to 3% ethyl acetate in hexane) to yield 52 (6.30 g, 71%) as an off-white solid. $^1$H NMR (400 MHz, CDCl$_3$) δ7.94 (d, 1H, J=7.8 Hz), 7.67 (d, 1H, J=8.1 Hz), 7.35 (app t, 1H, J=7.9 Hz), 3.51 (s, 1H); TLC (SiO$_2$: 20% ethyl acetate in hexane): R$_f$=0.27; ES (+)MS m/e=199 (M+1).

c) To a mixture of 52 (300 mg, 1.51 mmol) and piperazine-1-carboxylic acid tert-butyl ester (337 mg, 1.81 mmol) was added anhydrous dichloromethane (4 mL). After 45 min TLC indicated complete consumption of 52. The solvent was removed in vacuo and the residue was purified by flash column chromatography (SiO$_2$: gradient 40 to 70% ethyl acetate in hexane) to yield 53 (310 mg, 53%) as a white solid. $^1$H NMR (400 MHz, CDCl$_3$) δ7.46 (d, 1H, J=7.5 Hz), 7.22 (m, 3H), 5.48 (d, 1H, J=12.3 Hz), 3.51 (m, 4H), 3.34 (m, 4H), 1.47 (s, 9H); TLC (SiO$_2$: 50% ethyl acetate in hexane): R$_f$=0.12; ES (+) MS m/e=385 (M+1).

To a solution of 53 (300 mg, 0.78 mmol) in dichloromethane (0.65 mL) at 0° C. under nitrogen was added bromine (42 μL, 0.82 mmol) dropwise. After 10 min, the reaction was diluted with diethyl ether (0.5 mL) and triethylamine (114 μL, 0.81 mmol) was added dropwise. After 1 h at 0° C., the white precipitate was removed by filtration and the filtrate was concentrated in vacuo to provide 54 (359 mg, 99%) as a light yellow foam. $^1$H NMR (400 MHz, CDCl$_3$) δ7.48 (d, 1H, J=7.9 Hz), 7.24 (m, 2H), 7.15 (d, 1H, J=7.5 Hz), 3.71 (br s, 4H), 3.51 (m, 4H), 1.46 (s, 9H); ES (+) MS m/e=465 (M+1).

d) To a 0° C. solution of 54 (359 mg, 0.80 mmol) in THF (anhydrous, 3 mL) under nitrogen was added potassium tert-butoxide (97 mg, 0.80 mmol). After 1 h the reaction was allowed to reach ambient temperature and a solution of methylhydrazine (211 μL, 3.98 mmol) in dichloromethane (1 mL) was added. The resulting mixture was heated at 50° C. for 1.5 h. After cooling to room temperature, diethyl ether was added and the reaction mixture was washed with water. The organic layer was dried over Na$_2$SO$_4$ and concentrated. The residue was purified by flash column chromatography (SiO$_2$: gradient 20 to 50% ethyl acetate in hexane) to yield 55 (260 mg, 80%) as a colorless film. $^1$H NMR (400 MHz, CDCl$_3$) δ7.64 (d, 1H, J=7.8 Hz), 7.38 (d, 1H, J=7.9 Hz), 7.18 (app t, 1H, J=8.0 Hz), 6.31 (s, 1H), 3.77 (s, 3H), 3.56 (m, 4H), 2.91 (m, 4H), 1.46 (s, 9H); $^{13}$C NMR (100 MHz, CDCl$_3$) δ155.0, 151.8, 147.6, 135.3, 134.1, 130.9, 129.9, 129.4, 127.6, 96.4, 80.5, 52.5, 44.0, 35.4, 28.8; The regiochemistry was determined by NOESY. TLC (SiO$_2$: 50% ethyl acetate in hexane): R$_f$=0.44; ES (+) MS m/e=411 (M+1).

e) Title compound 56 was prepared according to the procedure of Example 16g,i,j except for using 55 as a reagent instead of 24. ES (+) MS m/e=549 (M+1).

Example 27

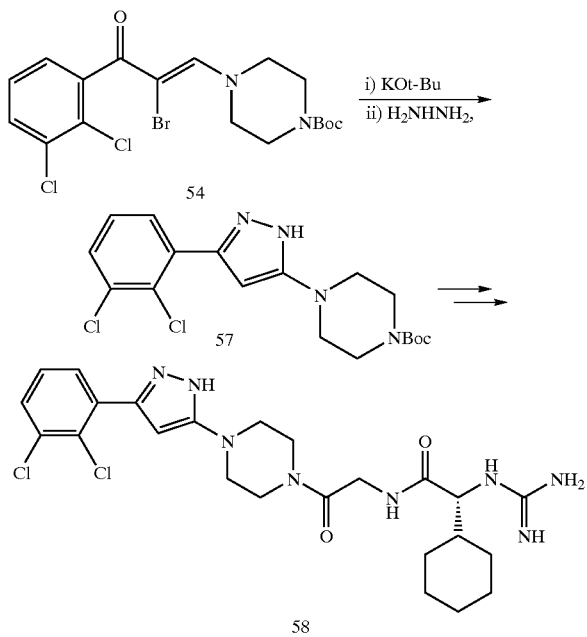

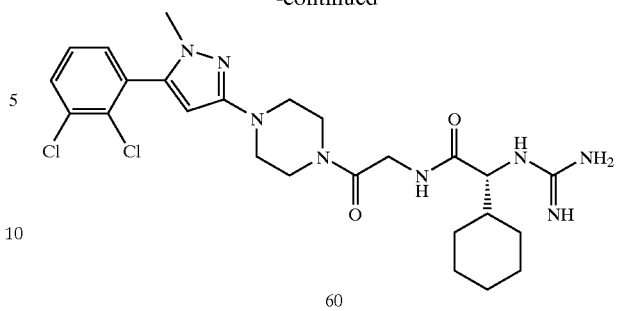

a) To a solution of 57 (130 mg, 0.33 mmol) in anhydrous THF (2 mL) was added sodium hydride (60% in mineral oil, 20 mg, 0.49 mmol). The flask was purged with nitrogen followed by addition of iodomethane (41 μL, 0.65 mmol). The resulting mixture was stirred under nitrogen until HPLC indicated complete consumption of 57. The reaction mixture was diluted with diethyl ether and washed with water. The organic phase was dried over $Na_2SO_4$ and concentrated. $^1$H NMR (400 MHz, $CDCl_3$) indicated a 1:1 mixture of 59 and 55. A pure sample of 59 (41 mg, 31%) was obtained by RP HPLC. $^1$H NMR (400 MHz, $CDCl_3$) δ7.58 (d, 1H, J=7.7 Hz), 7.29–7.22 (m, 2H), 5.74 (s, 1H), 3.59 (m, 7H), 3.25 (m, 4H), 1.48 (s, 9H). ES (+) MS m/e=411 (M+1).

b) Title compound 60 was prepared according to the procedure of Example 16g,i,j except for using 59 as a reagent instead of 24. ES (+) MS m/e=549 (M+1).

a) Pyrazole 57 was synthesized from 54 (1.00 g, 2.15 mmol) according to the procedure of Example 26e except hydrazine (1.0M in THF, 10.8 mL, 10.8 mmol) was used as a reagent and 57 was isolated as a white solid (0.25 g, 29%). $^1$H NMR (400 MHz, $CDCl_3$) δ7.46 (d, 1H, J=8.0 Hz), 7.39 (d, 1H, J=7.8 Hz), 7.24 (app t, 1H, J=7.9 Hz), 6.03 (s, 1H), 3.58 (m, 4H), 3.23 (m, 4H), 1.48 (s, 9H); TLC ($SiO_2$: 50% ethyl acetate in hexane): $R_f$=0.15; ES (+) MS m/e=341 (M−56).

b) Title compound 58 was prepared according to the procedure of Example 16g,i,j except for using 57 as a reagent instead of 24. ES (+) MS m/e=535 (M+1).

Example 28

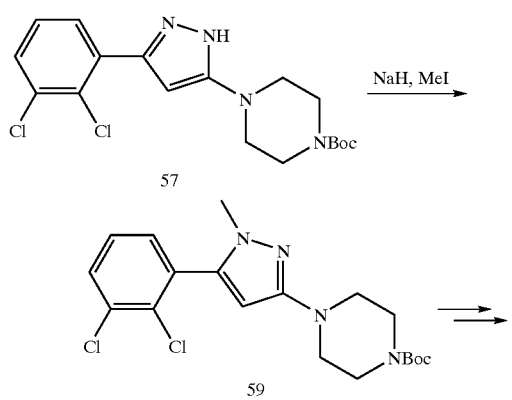

Example 29

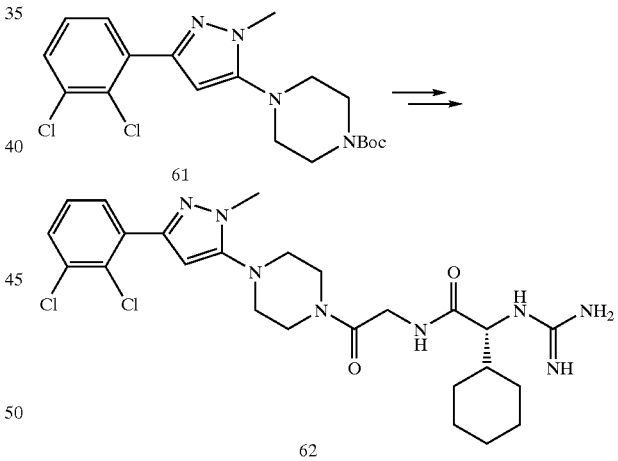

a) Compound 61 was prepared according to the procedure of Example 26c–e except for using 3-methyl-piperazine-1-carboxylic acid tert-butyl ester (prepared using literature procedures: Giardina et al. *J. Med. Chem.* 1993, 36, 690–698) as a reagent instead of piperazine-1-carboxylic acid tert-butyl ester. $^1$H NMR (400 MHz, $CDCl_3$) δ7.65 (d, 1H, J=7.8 Hz), 7.40 (d, 1H, J=7.9 Hz), 7.19 (app t, 1H, J=7.8 Hz), 6.40 (s, 1H), 3.88 (m, 2H), 3.79 (s, 3H), 3.21 (app t, 1H, J=10.5 Hz,), 3.00–2.82 (m, 3H), 2.78 (app t, 1H, J=9.9 Hz), 1.47 (s, 3H), 0.93 (d, 3H, J=5.6 Hz); ES (+) MS m/e=425 (M+1).

b) Title compound 62 was prepared according to the procedure of Example 16g,ij except for using 61 as a reagent instead of 24. ES (+) MS m/e=563 (M+1).

Example 30

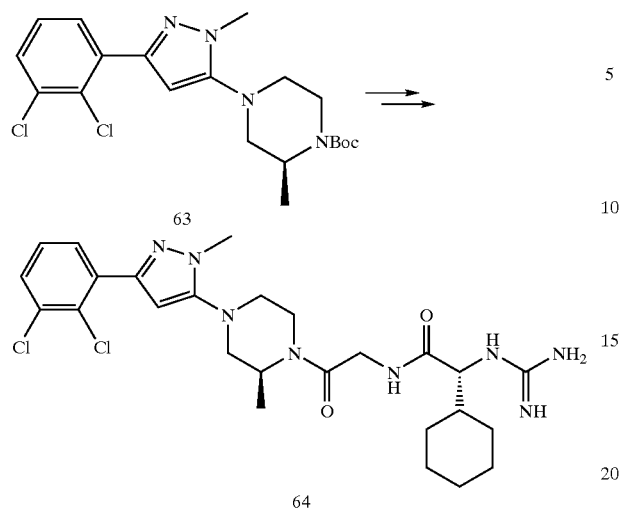

a) Compound 63 was prepared according to the procedure of Example 26c–e except for using 2S-methylpiperazine-1-carboxylic acid tert-butyl ester as a reagent instead of piperazine-1-carboxylic acid tert-butyl ester. $^1$H NMR (400 MHz, CDCl$_3$) δ7.63 (d, 1H, J=7.8 Hz), 7.40 (d, 1H, J=7.9 Hz), 7.19 (app t, 1H, J=7.9 Hz), 6.29 (s, 1H), 4.36 (br s, 1H), 3.96 (d, 1H, J=12.9 Hz), 3.80 (s, 3H), 3.25 (app t, 1H, J=12.6 Hz), 3.08 (d, 1H, J=11.0 Hz), 2.90 (app q, 2H, J=11.5 Hz), 2.74 (app t, 1H, J=11.8 Hz), 1.48 (s, 9H), 1.18 (d, 3H, J=6.6 Hz); ES (+) MS m/e=425 (M+1).

b) Title compound 64 was prepared according to the procedure of Example 16g,i,j except for using 63 as a reagent instead of 24. ES (+) MS m/e=563 (M+1).

Example 31

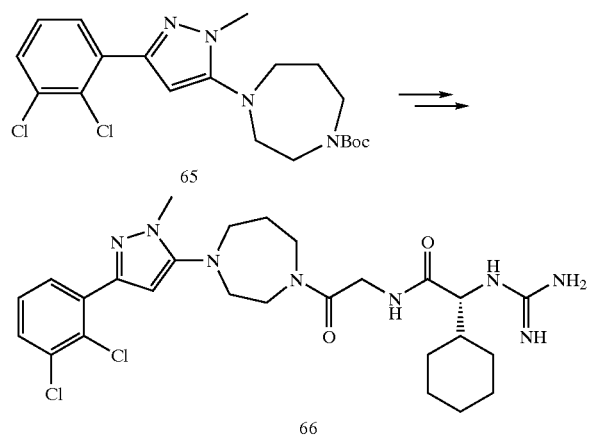

a) Compound 65 was prepared according to the procedure of Example 26c–e except for using tert-butyl 1-homopiperazinecarboxylate as a reagent instead of piperazine-1-carboxylic acid tert-butyl ester. $^1$H NMR (400 MHz, CDCl$_3$) δ7.66 (d, 1H, J=7.6 Hz), 7.41 (d, 1H, J=7.9 Hz), 7.21 (app t, 1H, J=7.8 Hz), 6.31 (s, 1H), 3.78 (s, 3H), 3.63–3.53 (br m, 4H), 3.17 (m, 4H), 1.94 (m, 2H), 1.48 (s, 9H); TLC (SiO$_2$; 35% ethyl acetate in hexane): R$_f$=0.24. ES (+) MS m/e=425 (M+1).

b) Title compound 66 was prepared according to the procedure of Example 16g,i,j except for using 65 as a reagent instead of 24. ES (+) MS m/e=563 (M+1).

Example 32

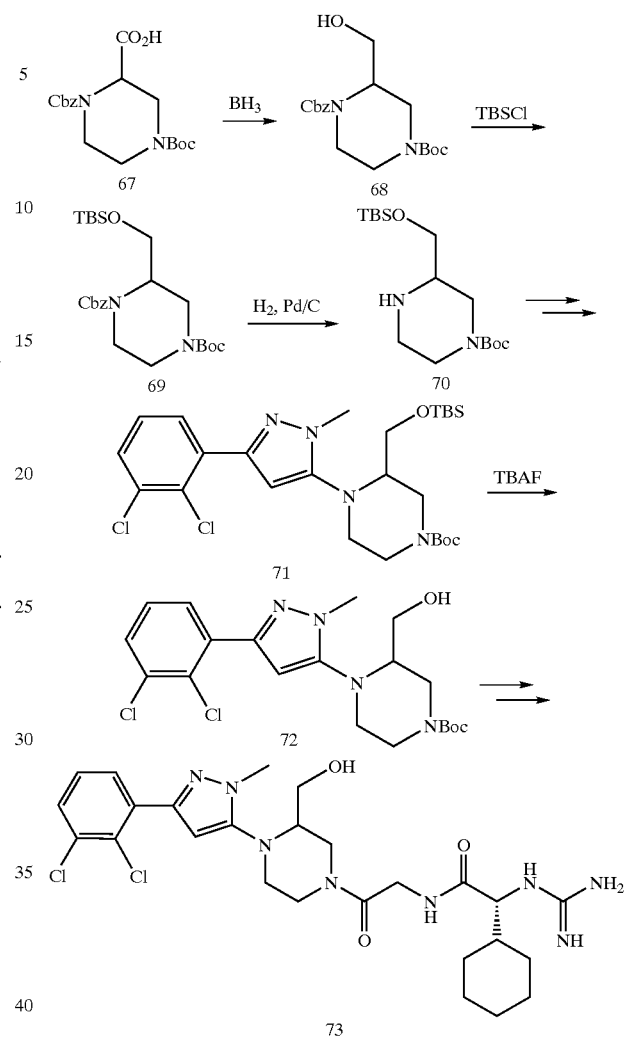

a) To a solution of piperazine-1,2,4-tricarboxylic acid 1-benzyl ester 4-tert-butyl ester (67) (prepared by the method of Dorsey et al. J. Med. Chem. 1994, 37, 3443–3451) (8.6 g, 23.6 mmol) in dry THF (90 mL) at room temperature was added borane.THF (1.0M in THF, 70 mL, 70 mmol). The resulting mixture was stirred at 70° C. for 1 hour and then cooled to room temperature. The reaction was quenched by dropwise addition of isopropanol and partitioned between saturated sodium bicarbonate (100 mL) and diethyl ether (100 mL). The aqueous layer was washed with diethyl ether (2×100 mL); the organic layer was dried over MgSO$_4$ and concentrated under reduced pressure to afford 68 (8.2 g, 99%). ES (+) MS m/e=373 (M+23).

b) To a solution of 68 (3.15 g, 9.0 mmol) and imidazole (0.67 g, 9.9 mmol) in dry DMF (18 mL) at room temperature was added tert-butyldimethylsilyl chloride (1.49 g, 9.9 mmol). The resulting mixture was stirred for 18 hours and then partitioned between water (100 mL) and ethyl acetate (100 mL). The aqueous layer was washed with ethyl acetate (2×50 mL); the organic layer was dried over MgSO$_4$ and concentrated under reduced pressure. The residue was purified by flash chromatography (SiO$_2$: 10 to 20% ethyl acetate in hexanes) to afford 69 (4.1 g, 98%). ES (+) MS m/e=487 (M+23).

c) A solution of 69 (4.1 g, 8.8 mmol) and 10% palladium on carbon (0.47 g, 0.44 mmol) in ethanol (30 mL) under an atmosphere of $H_2$ was shaken on a Parr hydrogenator (40 psi) for 1 h. After filtration, the filtrate was concentrated under reduced pressure to afford 70 (2.73 g, 93%). ES (+) MS m/e=331 (M+1).

d) Compound 71 was prepared according to the procedure of Example 26c–e except for using 70 as a reagent instead of piperazine-1-carboxylic acid tert-butyl ester. ES (+) MS m/e=555 (M+1).

e) To a solution of 71 (0.268 g, 0.48 mmol) in THF (2.5 mL) at 0° C. was added tetrabutylammonium fluoride (1.0M in THF, 0.96 mL, 0.96 mmol) dropwise. The resulting mixture was stirred for 30 minutes and concentrated under reduced pressure. The residue was purified by flash chromatography ($SiO_2$: 50 to 100% ethyl acetate in hexane) to afford 72 (0.14 g). ES (+) MS m/e=441 (M+1).

f) Title compound 73 was prepared according to the procedure of Example 16g,i,j except for using 72 as a reagent instead of 24. ES (+) MS m/e=579 (M+1).

Example 33

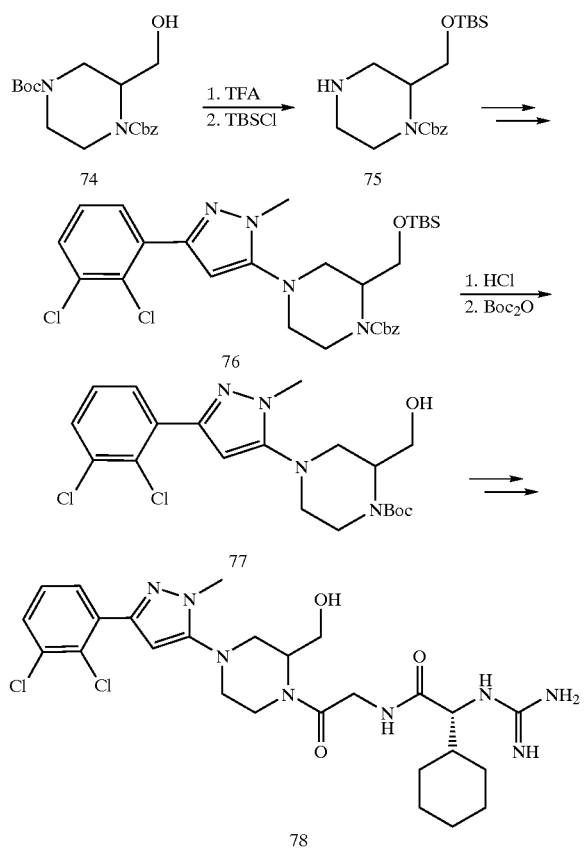

a) To a solution of 74 (4.26 g, 12.2 mmol) in dichloromethane (30 mL) was slowly added trifluoroacetic acid (8 mL). After stirring at ambient temperature for 45 min the reaction was diluted with 1,2-dichloroethane. The solvent was evaporated and the residue was dissolved in dichloromethane. To the resulting solution was added tert-butyldimethylsilyl chloride (5.50 g, 36.6 mmol), DMAP (300 mg, 2.44 mmol), and triethylamine (7.00 mL, 48.8 mmol). The mixture was stirred at room temperature overnight and then poured onto silica gel and purified by flash column chromatography ($SiO_2$: 0 to 6% methanol in dichloromethane) to yield 75 (3.40 g, 76%). TLC ($SiO_2$: 5% menthanol in dichloromethane): $R_f$=0.27; ES (+) MS m/e=365 (M+1).

b) Compound 76 was prepared according to the procedure of Example 26c–e except for using 75 as a reagent instead of piperazine-1-carboxylic acid tert-butyl ester. TLC ($SiO_2$: 20% ethyl acetate in hexane): $R_f$=0.24; ES (+) MS m/e=589 (M+1).

c) A mixture of 76 (794 mg, 1.35 mmol) in aqueous HCl (6N, 10 mL) was heated at reflux until HPLC indicated complete deprotection of the starting material. The solvent was evaporated and the residue was dissolved in methanol (3.5 mL) and treated with triethylamine (1.5 mL) and di-tert-butyl dicarbonate (297 mg, 1.35 mmol) at room temperature. After 1 h, the solvent was removed in vacuo and the residue was purified by flash column chromatography ($SiO_2$: 20 to 90% ethyl acetate in hexane) to yield 77 (540 mg, 91%) as a white powder. TLC ($SiO_2$: 50% ethyl acetate in hexane): $R_f$=0.08; ES (+) MS m/e=441 (M+1).

Title compound 78 was prepared according to the procedure of Example 16g,i,j except for using 77 as a reagent instead of 24. ES (+) MS m/e=579 (M+1).

Example 34

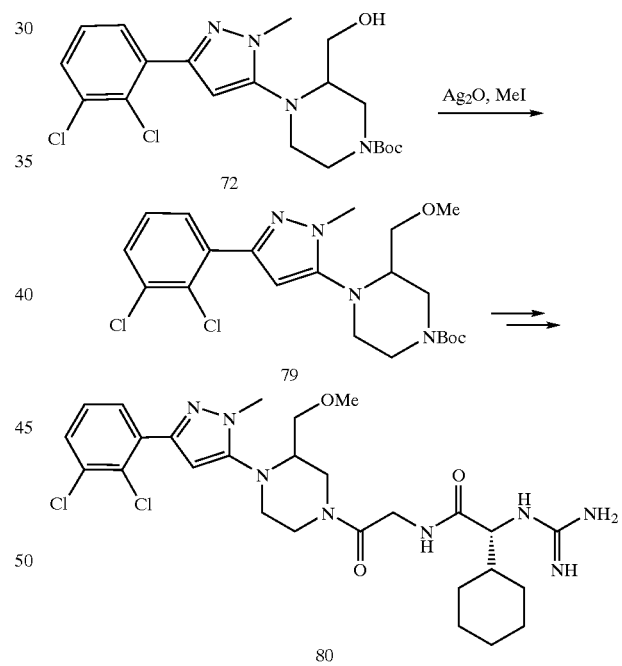

a) To a solution of 72 (100 mg, 0.23 mmol) and silver (I) oxide (157 mg, 0.68 mmol) in acetonitrile (1.1 mL) was added iodomethane (0.28 mL, 4.6 mmol). The resulting mixture was heated at 40° C. for 18 h and then cooled to room temperature. The heterogeneous solution was filtered and the filtrate concentrated under reduced pressure to afford crude 79 (0.1 g, 97%). ES (+) MS m/e=455 (M+1).

b) Title compound 80 was prepared according to the procedure of Example 16g,i,j except for using 79 as a reagent instead of 24. ES (+) MS m/e=593 (M+1).

Example 35

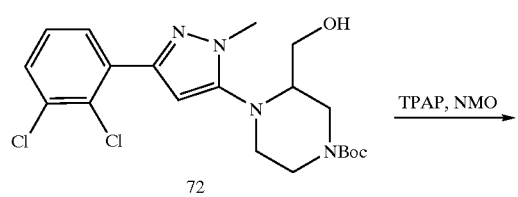

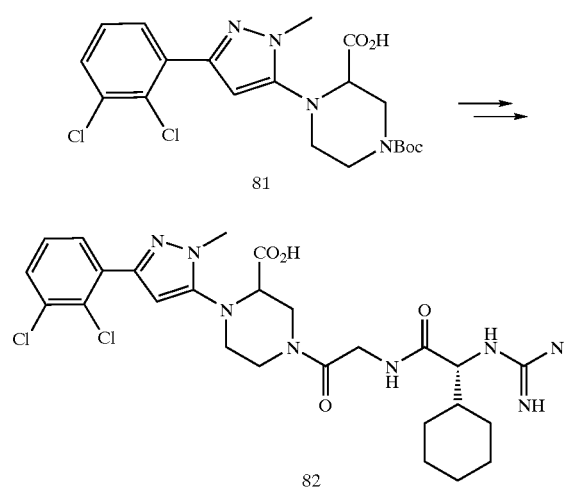

a) To a solution of 72 (110 mg, 0.25 mmol) and N-methylmorpholine-N-oxide (87 mg, 0.75 mmol) in wet acetonitrile (1.25 mL) was added tetrapropylammonium perruthenate (26 mg, 0.075 mmol). The resulting mixture was stirred at ambient temperature until LC/MS indicated complete conversion to product. The mixture was concentrated and purified by flash column chromatography (SiO$_2$: 0 to 10% methanol in dichloromethane) to yield 81 (60 mg, 53%). ES (+) MS m/e=455 (M+1).

b) Title compound 82 was prepared according to the procedure of Example 16g,ij except for using 81 as a reagent instead of 24. ES (+) MS m/e=593 (M+1).

Example 36

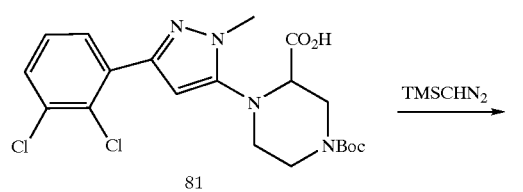

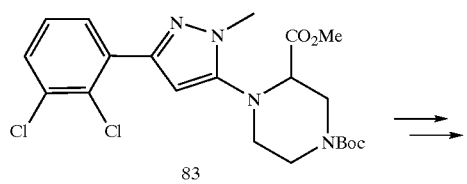

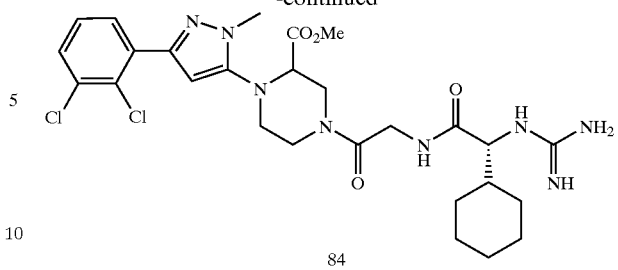

a) To a solution of 81 (45 mg, 0.09 mmol) in benzene/methanol (3:1, 5 mL) at room temperature was added trimethylsilyldiazomethane (2.0M in hexanes, 65 μL, 0.13 mmol). The resulting mixture was stirred for 15 minutes and concentrated under reduced pressure to afford crude 83 (46 mg, 100%). ES (+) MS m/e=469 (M+1).

b) Title compound 84 was prepared according to the procedure of Example 16g,i,j except for using 83 as a reagent instead of 24. ES (+) MS m/e=607 (M+1).

Example 37

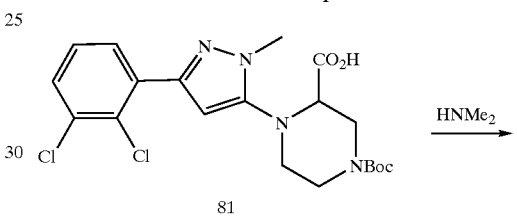

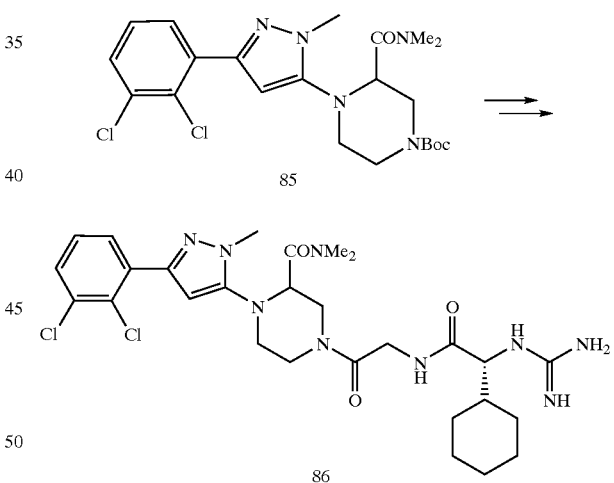

a) To a solution of 81 (60 mg, 0.13 mmol) in dichloromethane (0.7 mL) at room temperature was added (chloromethylene)dimethyl ammonium chloride (36 mg, 0.28 mmol). The resulting mixture was stirred for 1 hour, followed by addition of dimethylamine (2.0M in THF, 0.13 mL, 0.26 mmol). The reaction stirred for 30 minutes and then partitioned between water (5 mL) and ethyl acetate (5 mL). The aqueous layer was washed with ethyl acetate (5 mL); the organic layer was dried over MgSO$_4$ and concentrated under reduced pressure to afford crude 85 (60 mg, 95%). ES (+) MS m/e=482 (M+1).

b) Title compound 86 was prepared according to the procedure of Example 16g,i,j except for using 85 as a reagent instead of 24. ES (+) MS m/e=620 (M+1).

Example 38

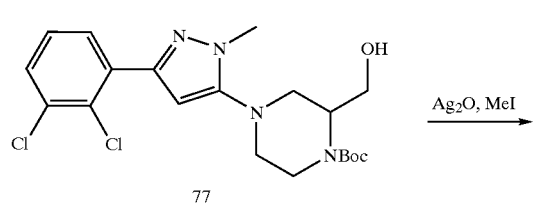

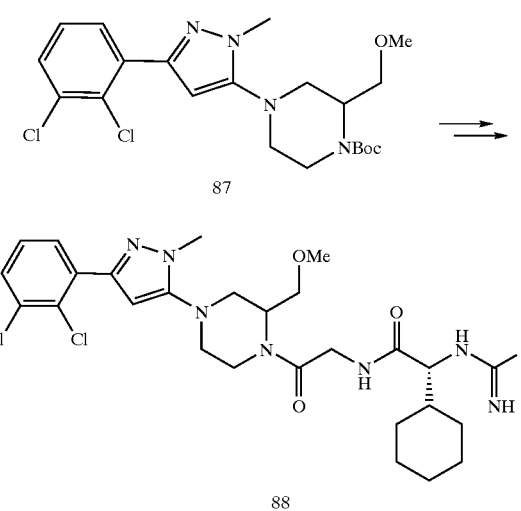

a) A mixture of 77 (70.0 mg, 0.16 mmol), Ag$_2$O (110 mg, 0.48 mmol), and iodomethane (60 μL, 0.95 mmol) in acetonitrile (0.5 mL) was refluxed under nitrogen for 2 h. After cooling to room temperature, the mixture was filtered through a plug of Celite and concentrated to yield 87 (79 mg, over theory) as a white solid. $^1$H NMR (400 MHz, CDCl$_3$) δ7.65 (dd, 1H, J$_1$=7.8 Hz, J$_2$=1.5 Hz), 7.40 (dd, 1H, J$_1$=7.9 Hz, J$_2$=1.5 Hz), 7.20 (app t, 1H, J=7.9 Hz), 6.29 (s, 1H), 4.36 (br s, 1H), 4.02 (m, 1H), 3.88 (app t, 1H, J=9.3 Hz), 3.78 (s, 3H), 3.46 (m, 1H), 3.39 (s, 3H), 3.34 (m, 1H), 3.10 (m, 1H), 3.07 (m, 1H), 2.82–2.72 (m, 2H), 1.48 (s, 9H); ES (+) MS m/e=455 (M+1).

b) Title compound 88 was prepared according to the procedure of Example 16g,i,j except for using 87 as a reagent instead of 24. ES (+) MS m/e=593 (M+1).

Example 39

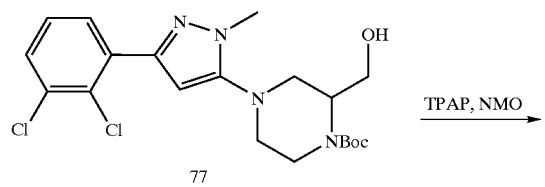

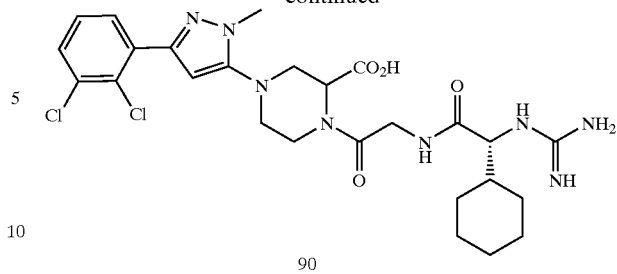

a) Compound 89 was prepared according to the procedure of Example 35a except for using 77 (100 mg, 0.23 mmol) as a reagent instead of 72. TLC (SiO$_2$: 10% methanol in dichloromethane): R$_f$=0.28; ES (+) MS m/e=455 (M+1).

b) Title compound 90 was prepared according to the procedure of Example 16g,i,j except for using 89 as a reagent instead of 24. ES (+) MS m/e=593 (M+1).

Example 40

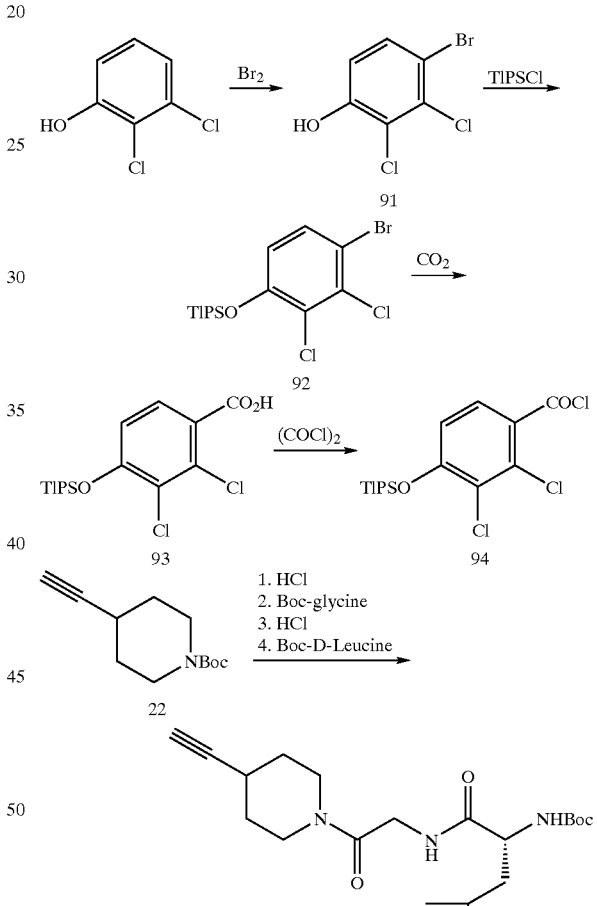

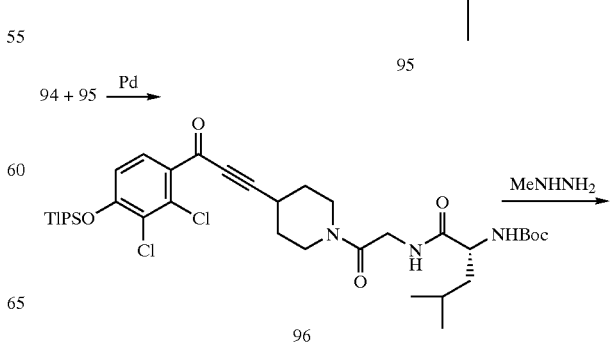

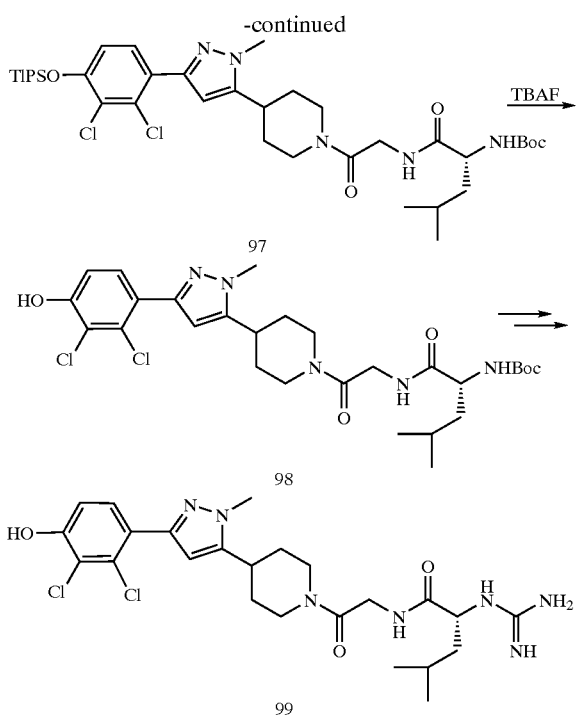

a) To a solution of 2,3-dichlorophenol (10.0 g, 61.3 mmol) in dichloromethane (50 mL) was added bromine (4.11 mL, 79.8 mmol) dropwise. After 2 h, HPLC indicated complete consumption of the starting material. The reaction mixture was slowly poured into a 10% aqueous sodium thiosulfate solution. The phases were separated and the aqueous layer was extracted with dichloromethane (3×). The combined organic layer was dried over $Na_2SO_4$ and concentrated. Purification of the crude residue by flash column chromatography ($SiO_2$: 0 to 20% ethyl acetate in hexane) yielded 91 (7.86 g, 53%) as a white solid. Spectroscopic data is identical to that of commercially available 4-bromo-2,3-dichloro-phenol from ChemService Inc. $^1$H NMR (400 MHz, $CDCl_3$) δ7.44 (d, 1H, J=8.9 Hz), 6.86 (d, 1H, J=8.9 Hz), 5.72 (s, 1H); TLC ($SiO_2$: 20% ethyl acetate in hexane): $R_f$=0.29.

b) To a solution of 91 (11.7 g, 48.4 mmol) in dry THF (100 mL) was added triethylamine (7.4 mL, 53.2 mmol) followed by triisopropylsilyl chloride (11.4 mL, 53.2 mmol). The reaction was stirred for 1 h at room temperature. Water (250 mL) and ethyl acetate (250 mL) were added and the layers separated. The aqueous layer was washed with additional ethyl acetate (200 mL). The organic layers were combined, dried over $MgSO_4$, filtered through a short plug of silica gel, concentrated under reduced pressure, and dried under high vacuum at 50° C. for 48 h to yield 92 (19.0 g, 99%) of a viscous oil. $^1$H-NMR (400 MHz, $CDCl_3$) δ7.36 (d, 1H, J=8.9 Hz), 6.72 (d, 1H, J=8.9 Hz), 1.32–1.27 (m, 3H), 1.10 (d, 18H, J=7.7 Hz).

c) To a −78° C. solution of 92 (15.4 g, 38.7 mmol) in anhydrous THF (385 mL) under nitrogen was added n-butyl lithium (1.57M in hexane, 24.6 mL, 38.7 mmol) dropwise. After 10 min at −78° C., carbon dioxide was bubbled through the solution for approximately 10 minutes. The mixture was allowed to reach room temperature and was quenched by careful addition of water (310 mL) followed by aqueous HCl (1.0N, 38.7 mL, 38.7 mmol). The mixture was extracted with diethyl ether (3×) and the combined organic layer was dried over $MgSO_4$ and concentrated. Purification of the crude residue by flash column chromatography ($SiO_2$: 0 to 70% ethyl acetate in hexane) yielded 93 (6.65 g, 47%) as a white solid. TLC ($SiO_2$: 30% ethyl acetate in hexane): $R_f$=0.39; ES (+) MS m/e=363 (M+1).

d) To a solution of 93 (6.45 g, 17.8 mmol) in anhydrous dichloromethane (120 mL) under nitrogen was added DMF (1.38 mL, 17.8 mmol) followed by dropwise addition of oxalyl chloride (2.01 mL, 23.1 mmol). After 10 min HPLC indicated complete consumption of the starting material and 1,2-dichloroethane was added. The solvent was removed in vacuo and the excess oxalyl chloride was removed by co-evaporation with 1,2-dichloroethane. The residue was dried under high vacuum to provide 94 which was used without further purification.

e) A solution of 22 (1.5 g, 7.0 mmol) in HCl/dioxane (4.0N, 10 mL) was stirred at room temperature for 30 minutes. The solvent was removed under reduced pressure to afford the desired amine (1.0 g, 100%) as the hydrochloride salt.

To N-Boc-glycine (1.5 g, 8.4 mmol) in dichloromethane (30 mL) was added EDC (1.6 g, 8.4 mmol), HOBt monohydrate (1.3 g, 8.4 mmol) and triethylamine (2.4 mL, 16.9 mmol). The piperidine amine (1.0 g, 7.0 mmol) was added and the reaction was stirred at room temperature overnight. The reaction mixture was partitioned with water (20 mL) and separated. The aqueous layer was extracted with dichloromethane (2×20 mL), and the combined organic layer was washed with 1M HCl (30 mL), saturated $NaHCO_3$ (30 mL) and dried over $Na_2SO_4$. The solvent was removed under reduced pressure to yield the desired amide (1.8 g, 96%).

To the amide (1.8 g, 6.8 mmol) was added HCl/dioxane (4.0N, 10 mL) and the reaction was stirred at room temperature for 30 minutes. The solvent was removed under reduced pressure to give the desired amine (1.4 g, 100%) as the hydrochloride salt.

To N-Boc-D-leucine (1.9 g, 8.1 mmol) in dichloromethane (30 mL) was added EDC (1.6 g, 8.1 mmol), HOBt monohydrate (1.2 g, 8.1 mmol) and triethylamine (2.2 mL, 16.3 mmol). To the activated acid solution was added amine (1.4 g, 6.8 mmol) and the reaction was stirred at room temperature for 4 h. The reaction mixture was partitioned with water (20 mL) and separated. The aqueous layer was extracted with dichloromethane (2×20 mL), and the combined organic layer was washed with 1M HCl (30 mL), saturated $NaHCO_3$ (30 mL) and dried over $Na_2SO_4$. The solvent was removed under reduced pressure to provide the crude amide (2.2 g); purification by flash chromatography ($SiO_2$: 25% ethyl acetate in hexanes) provided 95 (1.1 g).

f) A round bottom flask containing 94 (~17.8 mmol), CuI (0.17 g, 0.89 mmol), $PdCl_2(PPh_3)_2$ (0.63 mg, 0.89 mmol), and 95 (6.75 g, 17.8 mmol) was flushed with nitrogen for several minutes and then charged with a degassed solution of triethylamine (4.97 mL, 35.6 mmol) in toluene (120 mL). The reaction was monitored by HPLC and the solvent removed was removed when 94 had been completely consumed. The crude product 96 obtained was used without further purification.

g) A solution of 96 and methylhydrazine (9.47 mL, 178 mmol) in ethanol (120 mL) was stirred at ambient temperature for 1.5 h. The reaction mixture was concentrated and then redissolved in dichloromethane. The organic phase was washed with water and the resulting aqueous layer was extracted with dichloromethane (2×). The combined organic layer was dried over $Na_2SO_4$ and concentrated. Purification of the crude residue by flash column chromatography ($SiO_2$: 50 to 100% ethyl acetate in hexane) provided 97 (7.0 g, 52% for three steps from 93) as a white foam. TLC ($SiO_2$: ethyl acetate): $R_f$=0.19; ES (+) MS m/e=752 (M+1).

h) To a 0° C. solution of 97 (7.0 g, 9.3 mmol) in anhydrous THF (50 mL) was added tetrabutylammonium fluoride (1.0M in THF, 14 mL, 14 mmol) dropwise. The reaction mixture was stirred for 30 min and then partitioned between water (200 mL) and ethyl acetate (200 mL). The aqueous layer was washed with ethyl acetate (3×200 mL); the combined organic layer was dried over MgSO$_4$ and concentrated under reduced pressure. Purification of the crude product by flash column chromatography (SiO$_2$: 10% methanol in ethyl acetate) yielded 98 (5.0 g, 90%) as a solid. $^1$H NMR (400 MHz, CD$_3$OD) δ7.35 (d, 1H, J=8.5 Hz), 7.14 (d, 1H, J=8.8 Hz), 6.40 (s, 1H), 4.61 (d, 1H, J=12.8 Hz), 4.16–4.05 (m, 4H), 3.88 (s, 3H), 3.25 (m, 1H), 3.06 (m, 1H), 2.83 (m, 1H), 2.01 (m, 2H), 1.71–1.53 (m, 6H), 1.44 (s, 9H), 2.83 (m, 6H); TLC (SiO$_2$: 5% methanol in dichloromethane): R$_f$=0.10; ES (+) MS m/e= 596 (M+1).
i) Title compound 99 was prepared according to the procedure of Example 16j except for using 98 as a reagent instead of 27. ES (+) MS m/e=538 (M+1).

Example 41

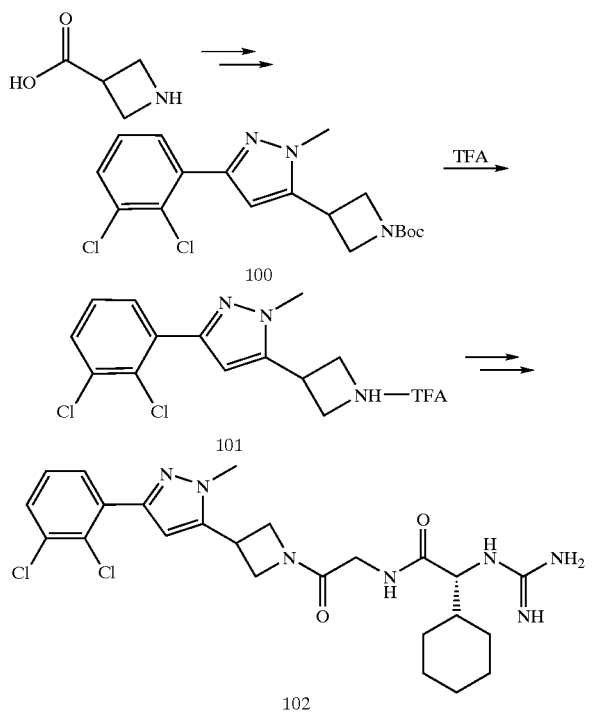

a) Compound 100 was prepared according to the procedure of Example 16a–f except for using azetidine-3-carboxylic acid as a reagent instead of piperidine-4-carboxylic acid.
b) To a solution of 100 (3.46 g, 9.1 mmol) in dichloromethane (20 mL) was added trifluoroacetic acid (5 mL). The resulting mixture was stirred for 3 hours at room temperature and concentrated under reduced pressure to afford crude 101 (4.4 g, 98%). ES (+) MS m/e=282 (M+1).
c) Title compound 102 was prepared according to the procedure of Example 16i,j except for using 101 as a reagent instead of 25. ES (+) MS m/e=520 (M+1).

Example 42

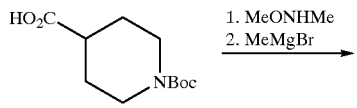

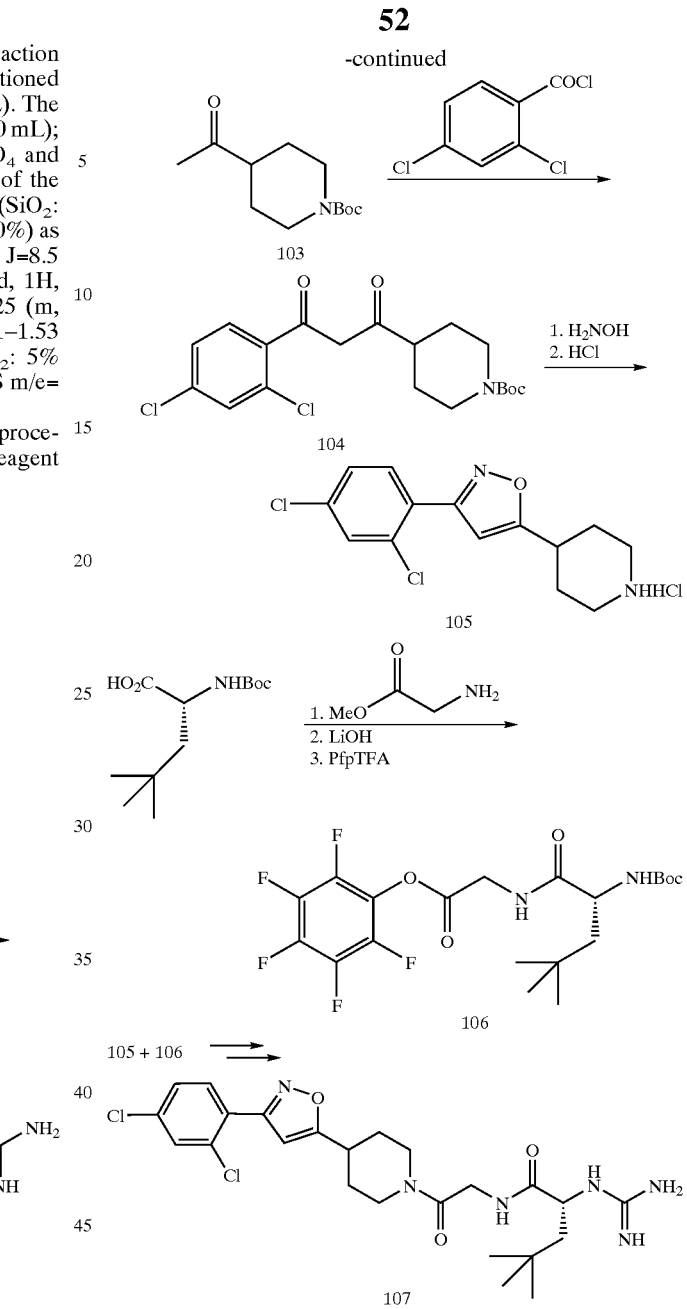

a) To N-Boc-isonipecotic acid (40 g, 0.17 mol) in dichloromethane (800 mL) was added EDC (36.8 g, 0.192 mol), HOBt monohydrate (29.4 g, 0.192 mol), triethylamine (51.0 mL, 0.366 mol) and N,O-dimethylhydroxylamine hydrochloride (18.7 g, 0.192 mol). The reaction mixture was stirred overnight at room temperature and then partitioned between water and dichloromethane. The aqueous layer was extracted with dichloromethane (3×200 mL); the combined organic layer was washed with 1M HCl (300 mL), saturated NaHCO$_3$ (300 mL) and dried over Na$_2$SO$_4$. The solvent was removed under reduced pressure to afford the desired amide (41.4 g, 87%).
b) To the amide (24.0 g, 88.2 mmol) in anhydrous THF (320 mL) at −78° C. under nitrogen was added via syringe over 10 minutes methyl magnesium bromide (1M in THF, 106 mL, 106 mmol). The reaction mixture was warmed to 0° C., stirred for 2 h, and then quenched with 1M HCl (150 mL). The mixture was extracted with ethyl acetate (3×200 mL) and the combined organic layer was dried over Na₂SO₄. The solvent was removed under vacuum to yield ketone 103 (19.4 g, 97%) as a yellow oil. ES (+) MS m/e=154 (M−55).

c) To a solution of 103 (500 mg, 2.2 mmol) in anhydrous THF (9 mL) at −78° C. under nitrogen was added dropwise via syringe lithium diisopropylamide (2.0M in heptane/THF/ether, 1.2 mL, 2.4 mmol). The mixture was stirred at −78° C. for 30 minutes, and then 2,4-dichlorobenzoyl chloride (339 μL, 2.4 mmol) in THF (1 mL) was added dropwise. The reaction mixture was warmed to −10° C., stirred for 2 h, and then quenched with water (10 mL). The aqueous layer was extracted with ethyl acetate (3×20 mL); the combined organic layer was washed with 1M HCl (10 mL), saturated NaHCO₃ (10 mL) and dried over Na₂SO₄. The solvent was removed under reduced pressure to give 839 mg of crude material which was purified by flash chromatography (SiO₂: 25% ethyl acetate in hexanes followed by 50% MeOH in ethyl acetate) to afford 104 (250 mg, 28%). ES (+) MS m/e=344 (M−55).

d) To a solution of 104 (125 mg, 0.31 mmol) in MeOH (2 mL) was added hydroxylamine (16M in H₂O, 63 μL, 1.0 mmol). The reaction mixture was refluxed for 4 h and the solvent was removed under reduced pressure. The resulting residue was partitioned between ethyl acetate (10 mL) and water (10 mL). The aqueous layer was extracted with ethyl acetate (3×10 mL); the combined organic layer was washed with 1M HCl (10 mL) and dried over Na₂SO₄. The solvent was removed under vacuum to afford the isoxazole (119 mg, 96%) as roughly a 1:1 mixture of regioisomers which was used without further purification. The isoxazole was dissolved in HCl/dioxane (4.0N, 2 mL) and stirred at room temperature for 30 min. The solvent was removed under vacuum to yield 105 (101 mg, 100%). ES (+) MS m/e=298 (M+1).

e) To a solution of N-Boc-D-t-butylalanine (5.0 g, 20.3 mmol) in dichloromethane (80 mL) was added EDC (4.7 g, 24.4 mmol), HOBt (3.3 g, 24.4 mmol), triethylamine (6.2 mL, 44.7 mmol), and then glycine methyl ester hydrochloride (3.1 g, 24.4 mmol). The reaction mixture was stirred overnight at room temperature and then partitioned between water (50 mL) and dichloromethane (20 mL). The aqueous layer was extracted with dichloromethane (2×50 mL); the combined organic layer was washed with 1M HCl (50 mL), saturated NaHCO₃ (50 mL) and dried over Na₂SO₄. The solvent was removed under reduced pressure to afford the desired amide (6.1 g, 95%).

The amide was dissolved in THF/H₂O (3:1, 80 mL) and lithium hydroxide monohydrate (1.6 g, 38.3 mmol) was added. The reaction was stirred overnight at room temperature and then neutralized with 1M HCl (50 mL). The mixture was extracted with ethyl acetate (3×100 mL) and the combined organic layer was dried over Na₂SO₄. The solvent was removed under reduced pressure to yield the carboxylic acid (5.8 g, 100%).

To a solution of the acid in THF (80 mL) was added pyridine (1.7 mL, 21.1 mmol) and pentafluorophenyl trifluoroacetate (3.6 mL, 21.1 mmol). The reaction was incomplete after stirring at room temperature overnight. Additional pentafluorophenyl trifluoroacetate (3.6 mL, 21.1 mmol) was used to drive the reaction to completion (2 h). The solvent was removed under reduced pressure and the resulting residue was dissolved in ethyl acetate (100 mL) and washed with 1M HCl (60 mL) followed by saturated NaHCO₃ (60 mL). The combined organic layer was dried over Na₂SO₄ and concentrated in vacuo to afford 14.0 g of crude material. The crude product was purified by flash chromatography (SiO₂: 50% ethyl acetate in hexane) to provide 106 (11.4 g) which was used without further purification. ES (+) MS m/e=413 (M−55).

f) Title compound 107 was prepared according to the procedure of Example 16g,i,j except for using 105 and 106 as reagents instead of 25 and 26. ES (+) MS m/e=524 (M+1).

Example 43

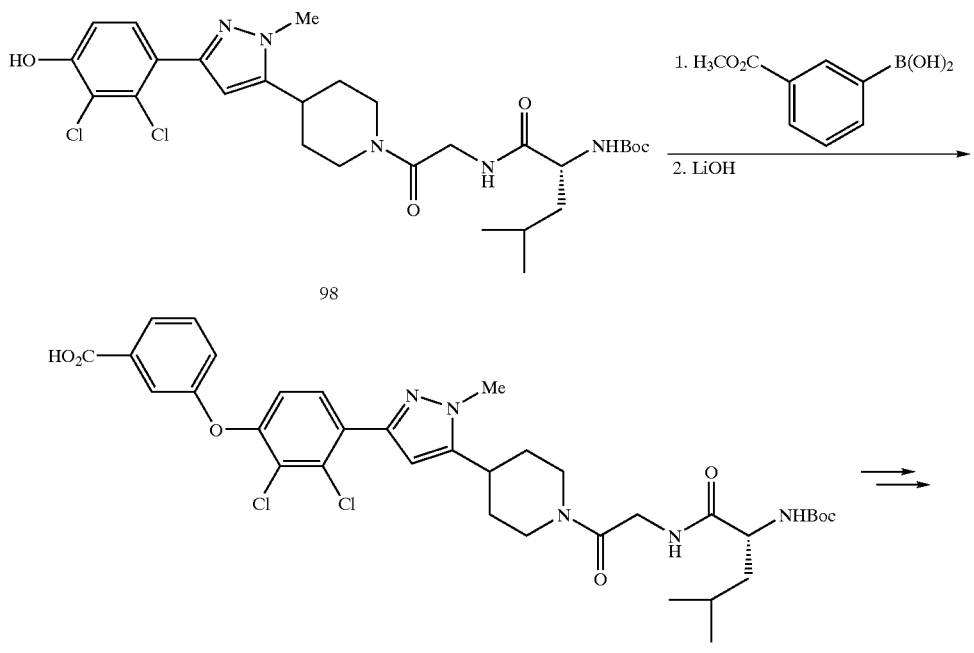

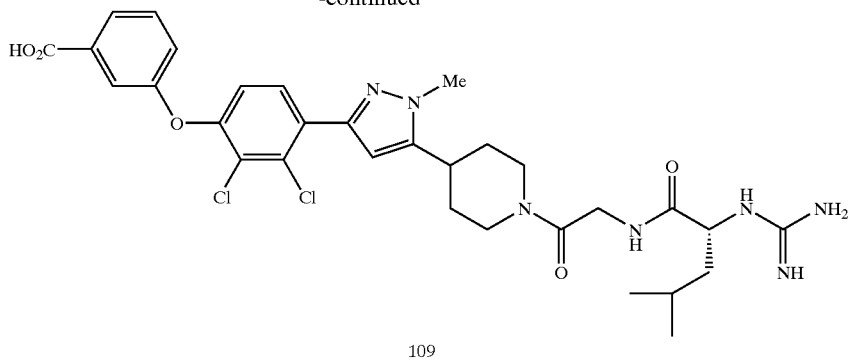

109 a) To phenol 98 (120 mg, 0.20 mmol) in dichloromethane (2 mL) was added (m-carbomethoxy)-phenylboronic acid (67 mg, 0.40 mmol), Cu(OAc)$_2$ (36 mg, 0.20 mmol), triethylamine (139 μL, 1.0 mmol) and molecular sieves (spatula tip). The reaction mixture was stirred at room temperature overnight and then filtered. The filtrate was diluted with dichloromethane (5 mL) and washed with water (5 mL). The aqueous layer was extracted with dichloromethane (3×5 mL); the combined organic layer was dried over Na$_2$SO$_4$ and concentrated under reduced pressure to afford the biaryl ether (250 mg) which was used without further purification.

To a solution of the aryl ether in THF/H$_2$O (3:1, 3 mL) was added lithium hydroxide (23 mg, 1.0 mmol). The reaction mixture was stirred at room temperature overnight and then neutralized with 1M HCl (4 mL). The mixture was extracted with ethyl acetate (3×5 mL); the combined organic layer was dried over Na$_2$SO$_4$ and concentrated under reduced pressure to yield the desired carboxylic acid 108. ES (+) MS m/e=716 (M+1).

b) Title compound 109 was prepared according to the procedure of Example 16j except for using 108 as a reagent instead of 27. ES (+) MS m/e=658 (M+1).

Example 44

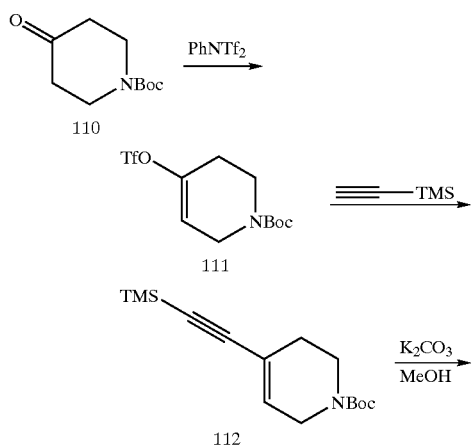

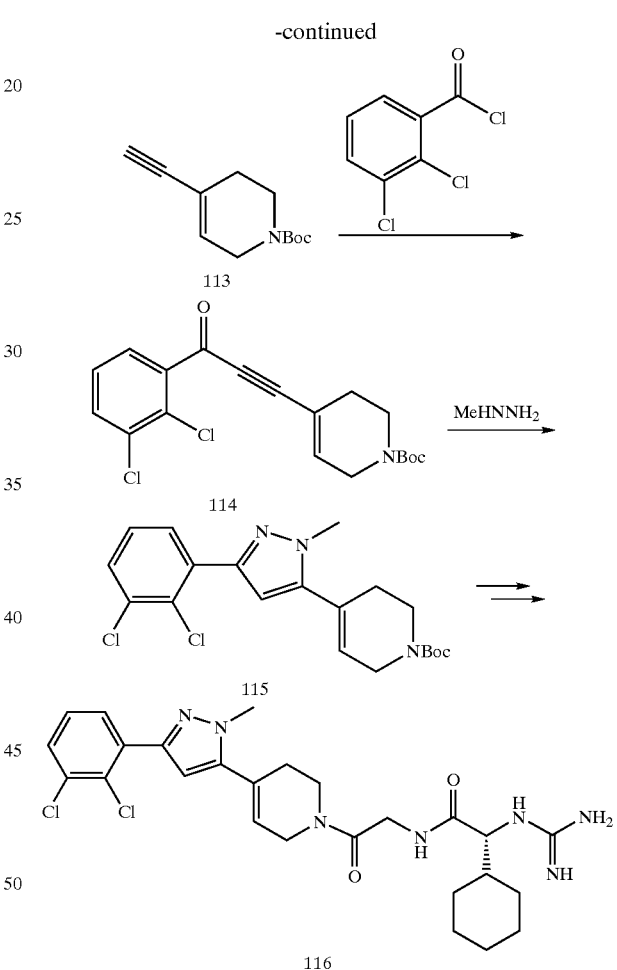

a) To a solution of 110 (5.0 g, 25.0 mmol) in dry THF (50 mL) at −78° C. was added lithium diisopropylamide (2.0M in heptane/THF/ethylbenzene, 19 mL, 38 mmol)) dropwise. The resulting mixture was stirred at −78° C. for 10 minutes followed by addition of N-phenyltrifluoromethane-sulfonimide (10.0 g, 28.0 mmol). The reaction was warmed to room temperature, stirred for 18 hours, and then partitioned between water (100 mL) and ethyl acetate (100 mL). The aqueous layer was washed with ethyl acetate (2×100 mL); the combined organic layer was dried over MgSO$_4$ and concentrated under reduced pressure. The residue was purified by flash chromatography (SiO₂: 15% ethyl acetate in hexanes) to afford 111 (6.32 g, 76%). ES (+) MS m/e=276 (M+1).

b) To a solution of 111 (1.0 g, 3.0 mmol), copper (I) iodide (29 mg, 0.15 mmol), (trimethylsilyl)acetylene (0.36 g, 3.6 mmol) and triethylamine (0.42 mL, 3.0 mmol) in toluene (15 mL) at room temperature was added dichlorobis(triphenylphosphine)palladium(II) (0.106 g, 0.15 mmol). The resulting mixture was stirred for 2 hours and concentrated under reduced pressure. The residue was purified by flash chromatography (SiO₂: 10% ethyl acetate in hexanes) to afford 112 (0.75 g, 89%). ES (+) MS m/e=224 (M−56).

c) To a solution of 112 (0.75 g, 2.7 mmol) in methanol (15 mL) at room temperature was added potassium carbonate (0.75 g, 5.4 mmol). The resulting mixture was stirred for 1 hour and then partitioned between water (50 mL) and ethyl acetate (50 mL). The aqueous layer was washed with ethyl acetate (2×50 mL); the combined organic layer were dried over MgSO₄ and concentrated under reduced pressure to afford crude 113 (0.53 g, 94%). ES (+) MS m/e=152 (M−56).

d) To a solution of 113 (0.52 g, 2.5 mmol), copper (I) iodide (0.024 g, 0.12 mmol), 2,3-dichlorobenzoyl chloride (0.68 g, 3.3 mmol) and triethylamine (0.45 mL, 3.3 mmol) in toluene (12 mL) at room temperature was added dichlorobis(triphenylphosphine)palladium(II) (88 mg, 0.12 mmol). The resulting mixture was stirred for 3 hours and then partitioned between saturated sodium bicarbonate (50 mL) and ethyl acetate (50 mL). The aqueous layer was washed with ethyl acetate (2×50 mL). The combined organic layer was dried over MgSO₄ and concentrated under reduced pressure. The residue was purified by flash chromatography (SiO₂: 25% ethyl acetate in hexanes) to afford 114 (0.93 g, 98%). ES (+) MS m/e=324 (M−56).

e) To a solution of 114 (0.93 g, 2.5 mmol) in ethanol (10 mL) at room temperature was added methylhydrazine (0.22 g, 4.9 mmol). The resulting mixture was stirred for 30 minutes and then concentrated under reduced pressure. The residue was purified by chromatography (SiO₂: 25% to 40% ethyl acetate in hexanes) to afford 115 (0.85 g, 85%) as a single regioisomer. ES (+) MS m/e=408 (M+1).

f) Title compound 116 was prepared according to the procedure of Example 16g,i,j except for using 115 as a reagent instead of 24. ES (+) MS m/e=546 (M+1).

Example 45

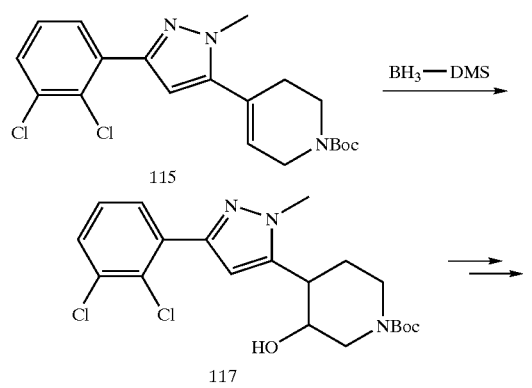

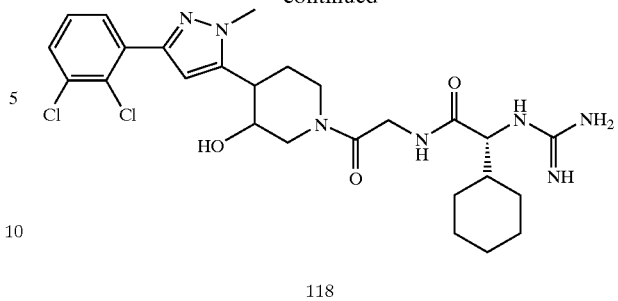

118 a) To a solution containing borane.THF (1.0M in THF, 4.4 mL, 4.4 mmol) in THF (9 mL) at 0° C. was added a solution of 115 (0.9 g, 2.2 mmol) in THF (2 mL). The resulting mixture was stirred for 4 h at room temperature and then treated with 3M NaOH/30% H₂O₂(aq) (1:1, 2 mL). After 15 min, the solution was partitioned between water (50 mL) and ethyl acetate (50 mL). The aqueous layer was washed with ethyl acetate (2×50 mL); the combined organic layer was dried over MgSO₄ and concentrated under reduced pressure. The residue was purified by RP HPLC to afford 117 (0.26 g, 28%). ES (+) MS m/e=426 (M+1).

b) Title compound 118 was prepared according to the procedure of Example 16g,i,j except for using 117 as a reagent instead of 24. ES (+) MS m/e=564 (M+1).

Example 46

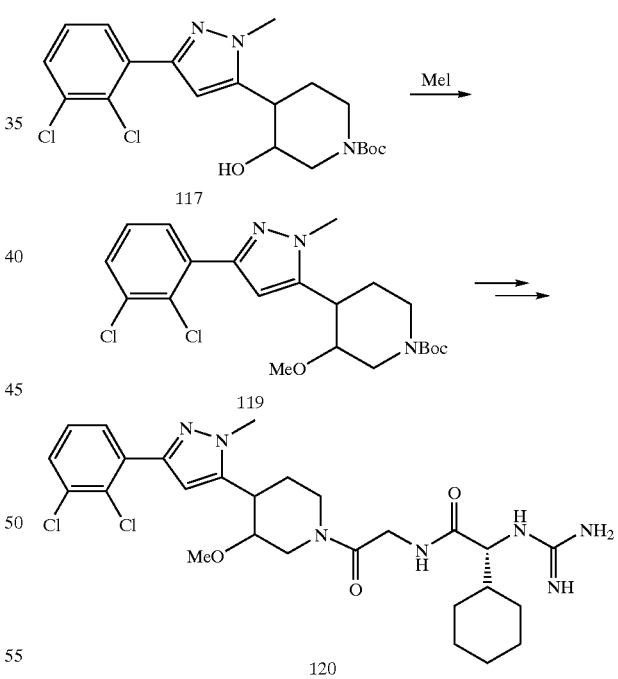

a) To a solution of 117 (50 mg, 0.11 mmol) in DMF (1 mL) at 0° C. was added sodium hydride (60% wt in mineral oil, 7 mg, 0.18 mmol) followed by iodomethane (12 μL, 0.17 mmol). The reaction mixture was stirred for 1 hour at room temperature and then partitioned between water (5 mL) and ethyl acetate (5 mL). The aqueous layer was washed with ethyl acetate (2×5 mL); the combined organic layer was dried and concentrated under reduced pressure to afford crude 119 (30 mg, 59%). ES (+) MS m/e=440 (M+1).

b) Title compound 120 was prepared according to the procedure of Example 16g,i,j except for using 119 as a reagent instead of 24. ES (+) MS m/e=578 (M+1).

Example 47

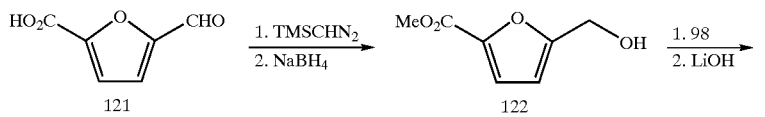

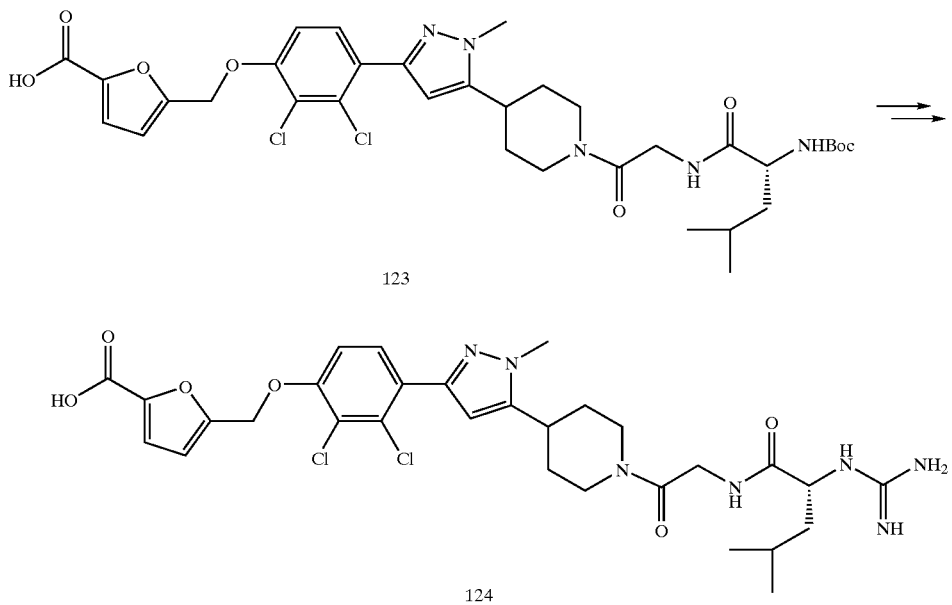

a) To a solution of 121 (0.15 g, 1.1 mmol) in benzene/methanol (5:1, 2 mL) at room temperature was added (trimethylsilyl)diazomethane (2.0M in hexanes, 0.6 mL, 1.2 mmol). The resulting solution was stirred at room temperature for 1 hour and concentrated under reduced pressure. The residue was dissolved in methanol (1 mL) and treated with sodium borohydride (80 mg, 2.1 mmol). After 2 h the reaction mixture was partitioned between water (10 mL) and ethyl acetate (10 mL). The aqueous layer was washed with ethyl acetate (2×10 mL); the combined organic layer was dried over MgSO₄ and concentrated under reduced pressure. The residue was purified by flash chromatography (SiO₂: 10 to 50% ethyl acetate in hexanes) to afford 122 (37 mg, 22%). ES (+) MS m/e=157 (M+1).

b) To a solution of 98 (70 mg, 0.12 mmol), 122 (37 mg, 0.23 mmol), and triphenylphosphine (61 mg, 0.23 mmol) in THF (1 mL) at room temperature was added diethyl azodicarboxylate (37 μL, 0.23 mmol). The resulting solution was stirred for 1 hour and then concentrated under reduced pressure. The residue was dissolved in THF (0.5 mL) and 1M LiOH (2 mL) and heated to 60° C. for 18 hours. The reaction mixture was cooled, concentrated under reduced pressure, and purified by RP HPLC to afford 123 (42 mg, 49%). ES (+) MS m/e=720 (M+1).

c) Title compound 124 was prepared according to the procedure of Example 16j except for using 123 as a reagent instead of 27. ES (+) MS m/e=662 (M+1).

Example 48

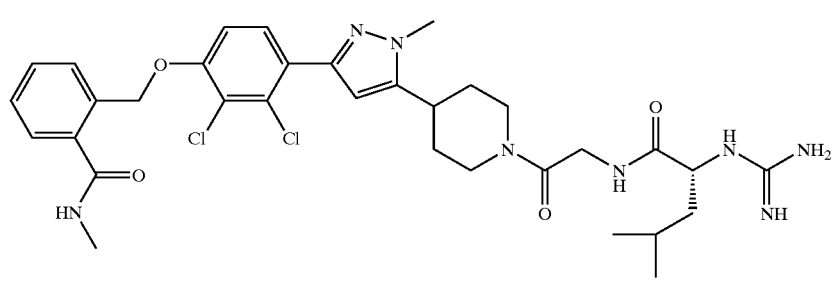

Title compound 125 was prepared from 98 according to the procedure of Example 48b,c except for using 2-hydroxymethyl-N-methylbenzamide as a reagent instead of 122. ES (+) MS m/e=685 (M+1).

Example 49

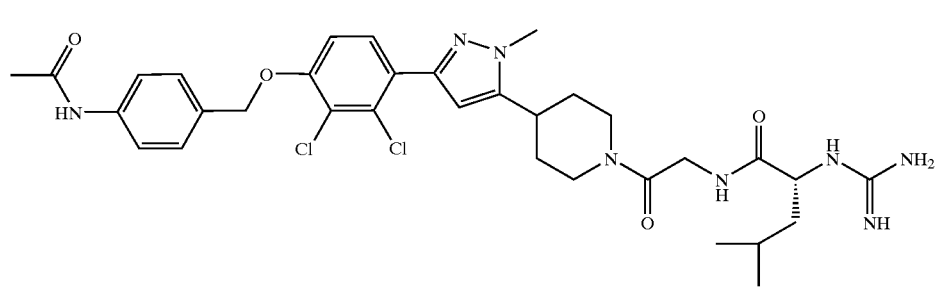

126

Title compound 126 was prepared from 98 according to the procedure of Example 48b,c except for using N-(4-hydroxymethyl-phenyl)acetamide as a reagent instead of 122. ES (+) MS m/e=685 (M+1).

Example 50

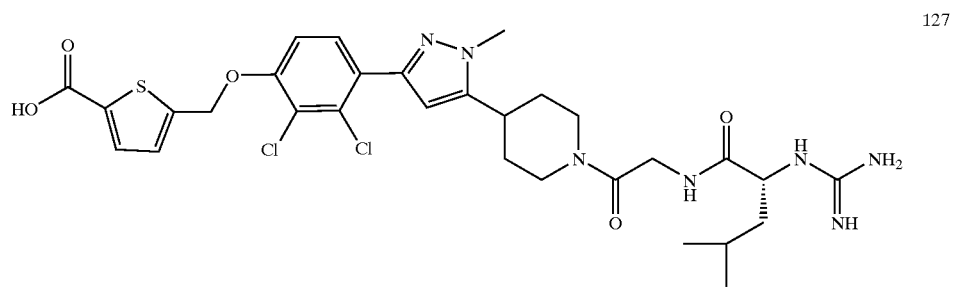

127

Title compound 127 was prepared from 98 according to the procedure of Example 48b,c except for using 5-hydroxymethyl-thiophene-2-carboxylic acid as a reagent instead of 122. ES (+) MS m/e=678 (M+1).

Example 51

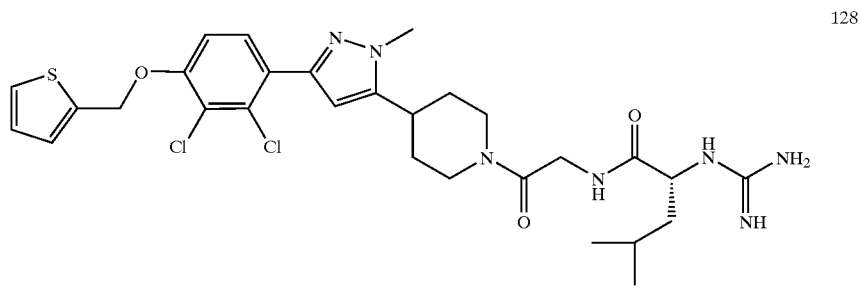

128

Title compound 128 was prepared from 98 according to the procedure of Example 48b,c except for using thiophen-2-yl-methanol as a reagent instead of 122.

Example 52

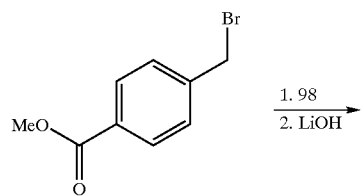

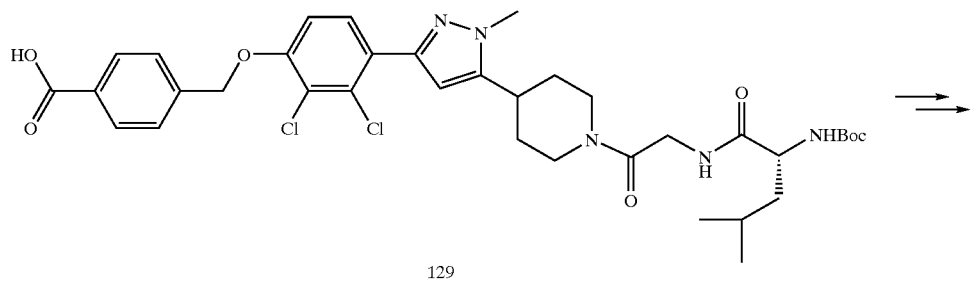

129

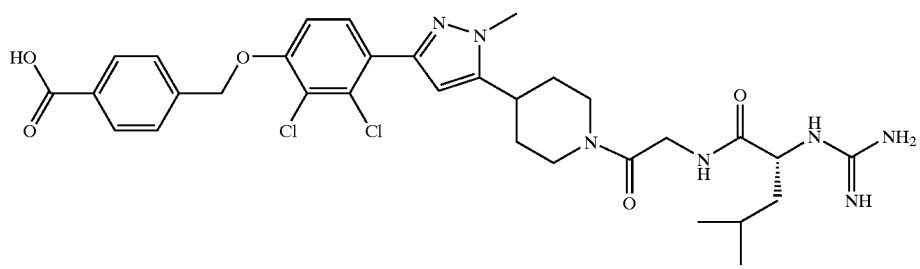

130 a) A heterogeneous solution containing 98 (75 mg, 0.12 mmol), 4-bromomethyl-benzoic acid methyl ester (43 mg, 0.19 mmol), and potassium carbonate (35 mg, 0.25 mmol) in dry DMF (0.5 mL) was heated to 60° C. for 18 h. The reaction mixture was cooled to room temperature and then partitioned between water (10 mL) and ethyl acetate (10 mL). The aqueous layer was washed with ethyl acetate (2×10 mL); the combined organic layer was dried over MgSO$_4$ and concentrated under reduced pressure.

b) The resulting residue was dissolved in THF (0.5 mL) and 1M LiOH (2 mL) and heated to 60° C. for 18 h. The reaction mixture was cooled, concentrated under reduced pressure, and then purified by RP BPLC to afford 129 (36 mg, 39%). ES (+) MS m/e=730 (M+1).

c) Title compound 130 was prepared according to the procedure of Example 16j except for using 129 as a reagent instead of 27. ES (+) MS m/e=672 (M+1).

Example 53

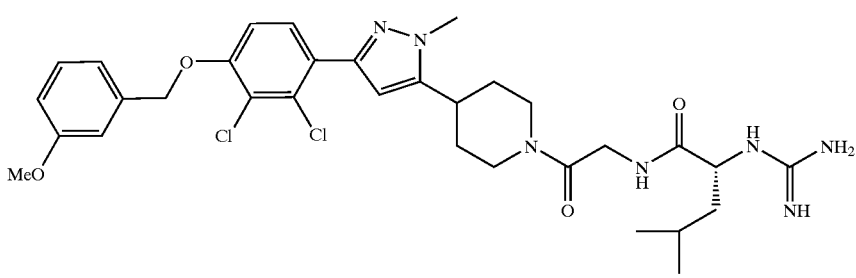

131

Title compound 131 was prepared according to the procedure of Example 52a,c except for using 1-bromomethyl-3-methoxybenzene as a reagent instead of 4-(bromomethyl)benzoic acid methyl ester. ES (+) MS m/e=658 (M+1).

Example 54

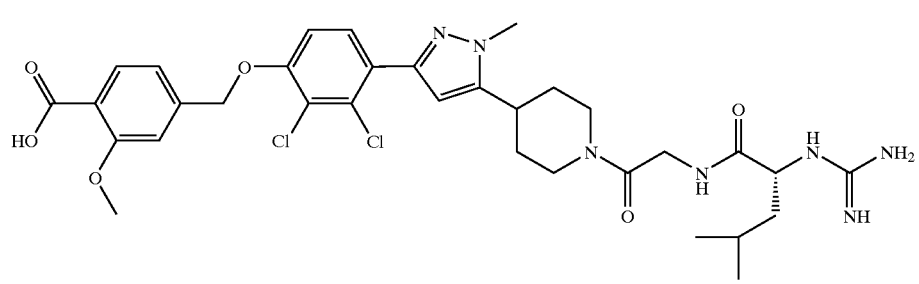

132

Title compound 132 was prepared according to the procedure of Example 52a–c except for using 4-bromomethyl-3-methoxybenzoic acid methyl ester as a reagent instead of 4-(bromomethyl)benzoic acid methyl ester. ES (+) MS m/e= 702 (M+1).

Example 55

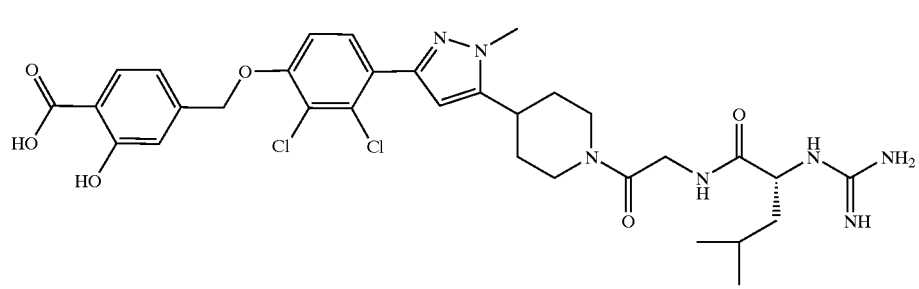

133

Title compound 133 was prepared according to the procedure of Example 52a,c except for using 4-bromomethyl-2-(tert-butyldimethylsilanyloxy)benzoic acid tert-butyldimethylsilyl ester as a reagent instead of 4-(bromomethyl)benzoic acid methyl ester. ES (+) MS m/e= 688 (M+1).

Example 56

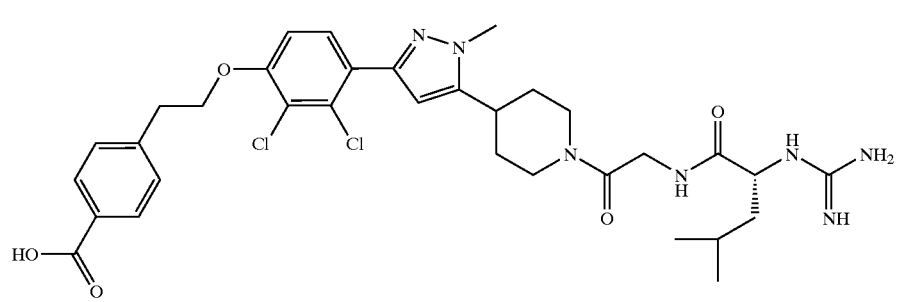

134

Title compound 134 was prepared according to the procedure of Example 52a,c except for using 4-(2-bromoethyl)benzoic acid as a reagent instead of 4-bromomethyl-benzoic acid methyl ester. ES (+) MS m/e=686 (M+1).

Example 57

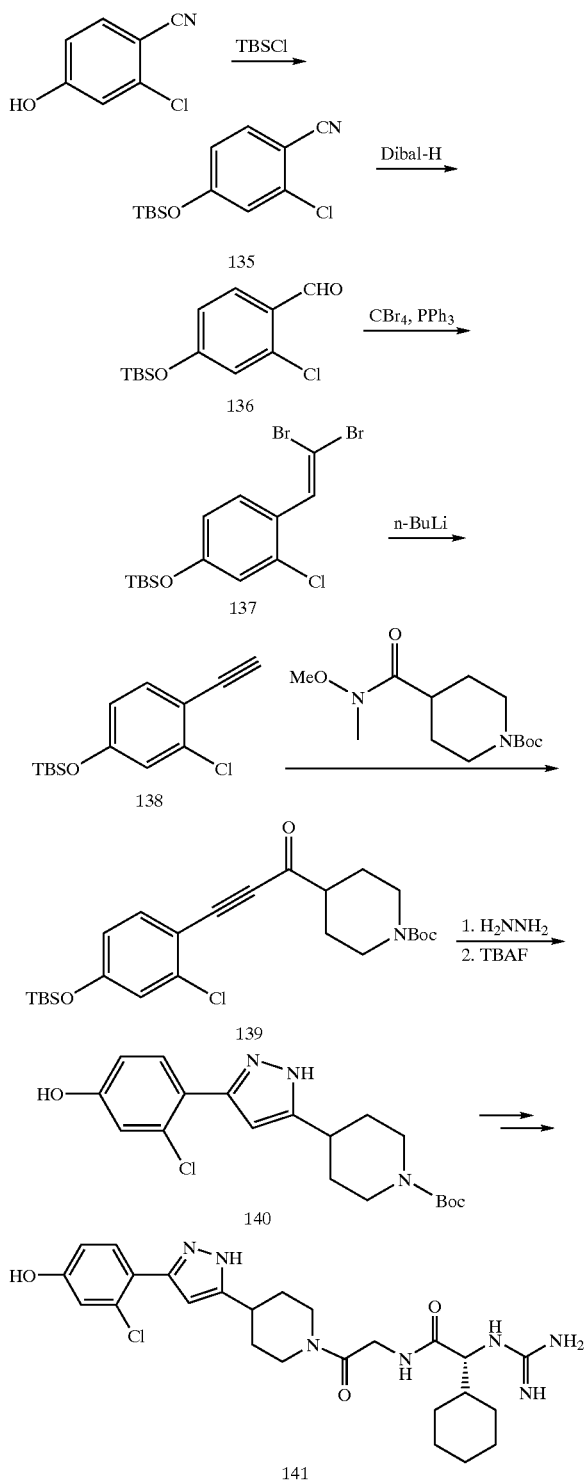

a) To a solution containing 2-chloro-4-hydroxy-benzonitrile (9.5 g, 61.9 mmol) and imidazole (4.63 g, 68.0 mmol) in dry DMF (120 mL) at room temperature was added tert-butyldimethylsilyl chloride (10.3 g, 68.0 mmol). The resulting mixture was stirred for 2 h and then partitioned between water (200 mL) and ethyl acetate (200 mL). The aqueous layer was washed with ethyl acetate (2×200 mL); the combined organic layer was dried over MgSO$_4$, filtered through a short plug of silica gel, and concentrated under reduced pressure to afford 135 (16.5 g, 99%). ES (+) MS m/e=268 (M+1).

b) To a solution containing 135 (16.5 g, 61.6 mmol) in dichloromethane (200 mL) at −78° C. was added diisobutylaluminum hydride (1.5M in toluene, 54.0 mL, 81 mmol) dropwise. The reaction mixture was warmed to room temperature and stirred for 30 min. The reaction was quenched by slow addition of isopropanol, diluted with 1M HCl (100 ml) and stirred for 1 h. The aqueous layer was washed with ethyl acetate (2×200 mL); the combined organic layer was washed with brine, dried over MgSO$_4$, and concentrated to afford 136 (15.9 g, 95%). ES (+) MS m/e=271 (M+1).

c) To a solution containing 136 (10.7 g, 39.3 mmol) and carbon tetrabromide (13.0 g, 39.3 mmol) in dichloromethane (150 mL) was added triphenylphosphine (20.6 g, 78.6 mmol). The resulting mixture was stirred at room temperature and then partitioned between water (300 mL) and ethyl acetate (300 mL). The aqueous layer was washed with ethyl acetate (2×150 mL); the combined organic layer was dried over MgSO$_4$ and concentrated under reduced pressure. The residue was diluted with hexanes and the resulting precipitate was removed by filtration. Concentration of the filtrate under reduced pressure provided 137 (11.3 g, 67%).

d) To a solution containing 137 (11.3 g, 26.4 mmol) in THF (100 mL) at −78° C. was added N-butyllithium (1.6M in hexanes, 33.0 mL, 52.8 mmol). The reaction mixture was warmed to 0° C., stirred for 30 min, and then partitioned between water (200 mL) and ethyl acetate (200 mL). The aqueous layer was washed with ethyl acetate (2×200 mL); the combined organic layer was dried over MgSO$_4$ and concentrated under reduced pressure to afford crude 138 (7.0 g, 99%).

e) To a solution containing 138 (0.75 g, 2.8 mmol) in THF (11 mL) at −78° C. was added lithium bis(trimethylsilyl)amide (1.0M in THF, 3.0 mL, 3.0 mmol). Upon complete addition, a solution of 4-(methoxymethylcarbamoyl)piperidine-1-carboxylic acid tert-butyl ester (0.76 g, 2.8 mmol) in THF (3 mL) was added and the resulting mixture was allowed to warm to 0° C. The reaction mixture was stirred for 30 minutes, warmed to room temperature, and then partitioned between saturated ammonium chloride (50 mL) and ethyl acetate (50 mL). The aqueous layer was washed with ethyl acetate (2×50 mL); the combined organic layer was dried over MgSO$_4$ and concentrated under reduced pressure to afford 139 (1.3 g, 97%).

f) To a solution containing 139 (6.0 g, 12.5 mmol) in ethanol (12 mL) was added hydrazine (1 mL). The resulting mixture was stirred at room temperature for 1 h and then partitioned between water (50 mL) and ethyl acetate (50 mL). The aqueous layer was washed with ethyl acetate (3×50 mL); the combined organic layer was dried over MgSO$_4$ and concentrated under reduced pressure. To the resulting residue in THF (12 mL) at 0° C. was added tetrabutylammonium fluoride (1.0M in THF, 13 mL, 13 mmol) dropwise. After 30 min the solution was partitioned between water (50 mL) and ethyl acetate (50 mL). The aqueous layer was washed with ethyl acetate (3×50 mL); the combined organic layer was dried over MgSO$_4$ and concentrated under reduced pressure. The residue was purified by flash chromatography (SiO$_2$: 50 to 75% ethyl acetate in hexanes) to afford 140 (3.43 g, 72%).

g) Title compound 141 was prepared according to the procedure of Example 16g,i,j except for using 140 as a reagent instead of 24. ES (+) MS m/e=516 (+1).

Example 58

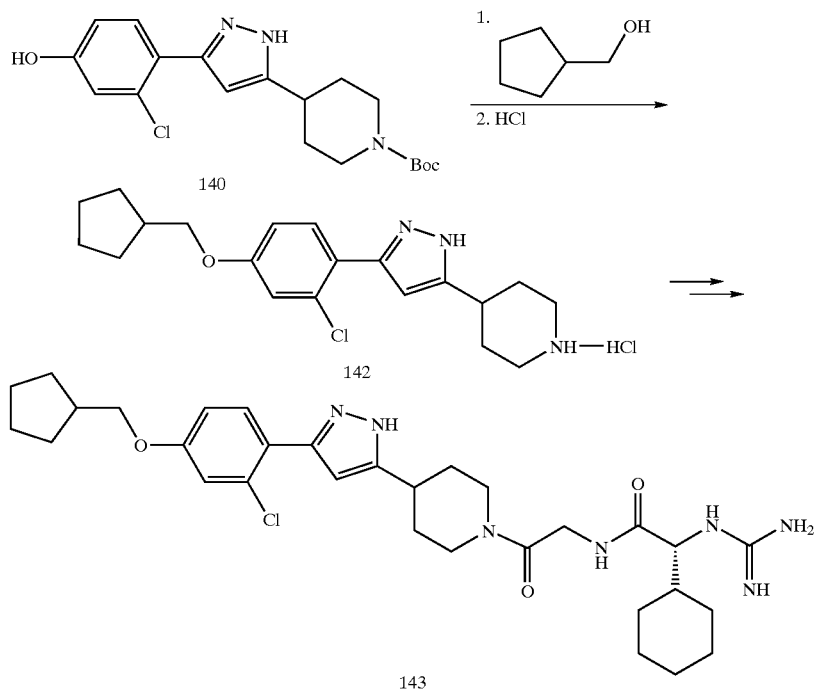

a) To a solution containing 140 (80 mg, 0.21 mmol), triphenylphosphine (56 mg, 0.21 mmol), and cyclopentanemethanol (23 μL, 0.21 mmol) in dichloromethane (1 mL) was added di-tert-butyl-azodicarboxylate (49 mg, 0.21 mmol). The resulting mixture was stirred for 18 h, concentrated under reduced pressure, and then purified by flash chromatography (SiO$_2$: 50% ethyl acetate in hexanes). To the resulting residue in dioxane (0.5 mL) was added HCl/dioxane (4.0N, 1 mL). After stirring for 1 h, the mixture was concentrated under reduced pressure to afford 142 (64 mg, 76%). ES (+) MS m/e=360 (M+1).

b) Title compound 143 was prepared according to the procedure of Example 16i,j except for using 142 as a reagent instead of 25. ES (+) MS m/e=598 (M+1).

Example 59

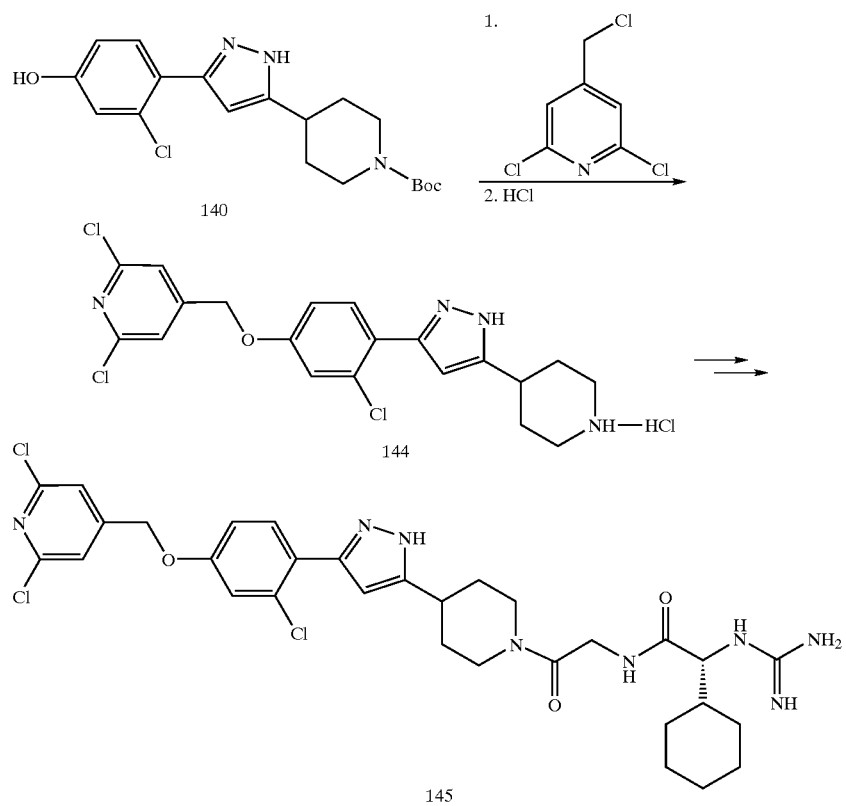

a) A solution of 140 (100 mg, 0.26 mmol), 2,6-dichloro-4-chloromethyl-pyridine hydrochloride (75 mg, 0.32 mmol), and cesium carbonate (258 mg, 0.79 mmol) in DMSO (1 mL) was stirred at 65° C. for 1 hour. The reaction mixture was cooled to room temperature and then partitioned between water (10 mL) and ethyl acetate (10 mL). The aqueous layer was washed with ethyl acetate (3×10 mL); the combined organic layer was dried over MgSO₄ and concentrated under reduced pressure. The residue was purified by flash chromatography (SiO₂: 50 to 75% ethyl acetate in hexanes).

To a solution of the residue in dioxane (0.5 mL) was added HCl/dioxane (4.0N, 1 mL). The reaction mixture was stirred for 1 hour and then concentrated under reduced pressure to afford 144 (36 mg, 27%). ES (+) MS m/e=439 (M+3).

b) Title compound 145 was prepared according to the procedure of Example 16i,j except for using 144 as a reagent instead of 25. ES (+) MS m/e=675 (M+1).

Example 60

146

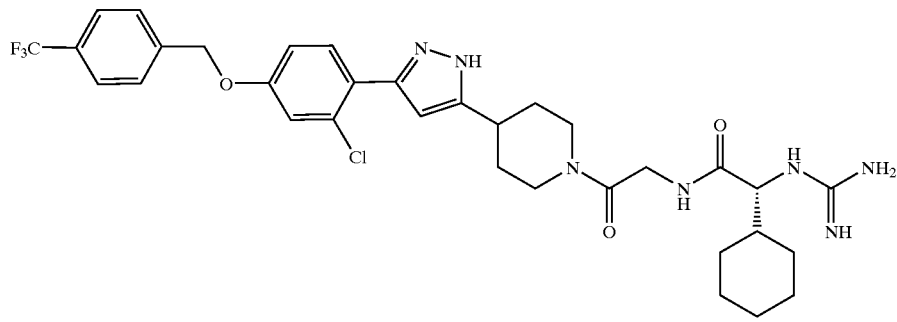

Title compound 146 was prepared according to the procedure of Example 59a,b except for using 1-bromomethyl-4-trifluoromethylbenzene as a reagent instead of 2,6-dichloro-4-chloromethylpyridine hydrochloride. ES (+) MS m/e=674 (M+1).

Example 61

147

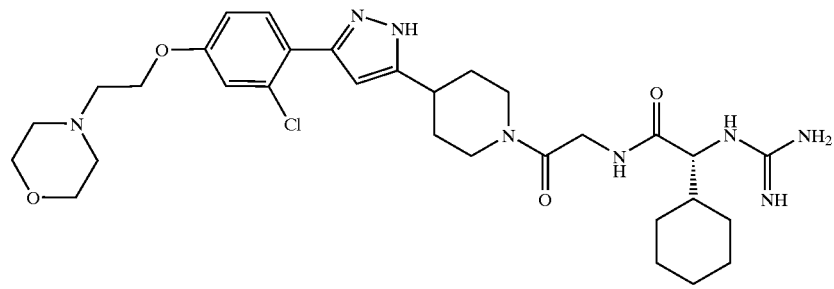

Title compound 147 was prepared according to the procedure of Example 59a,b except for using 4-(2-chloroethyl)-morpholine hydrochloride as a reagent instead of 2,6-dichloro-4-chloromethyl-pyridine hydrochloride. ES (+) MS m/e=629 (M+1).

Example 62

148

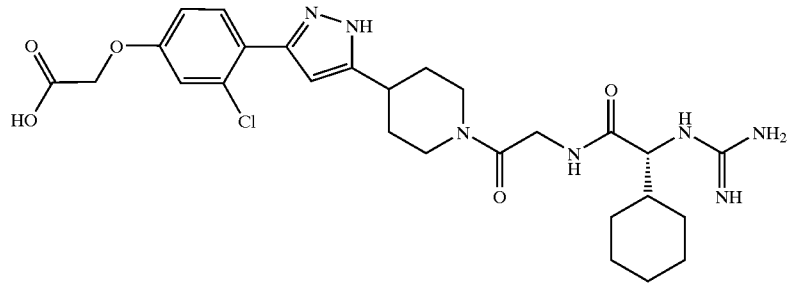

Title compound 148 was prepared according to the procedure of Example 52a–c except for using methyl bromoacetate as a reagent instead of 4-bromomethyl-benzoic acid methyl ester. ES (+) MS m/e=574 (M+1).

Example 63

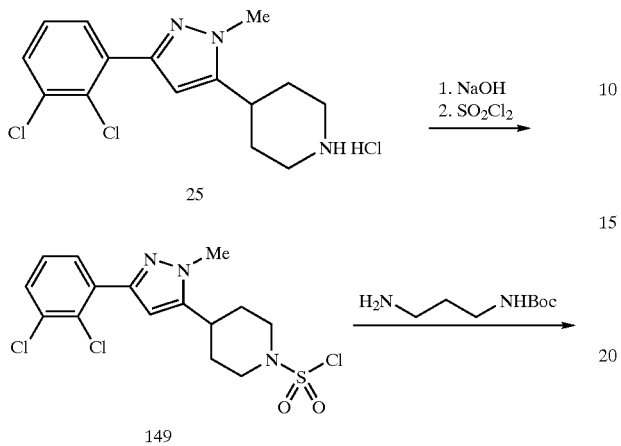

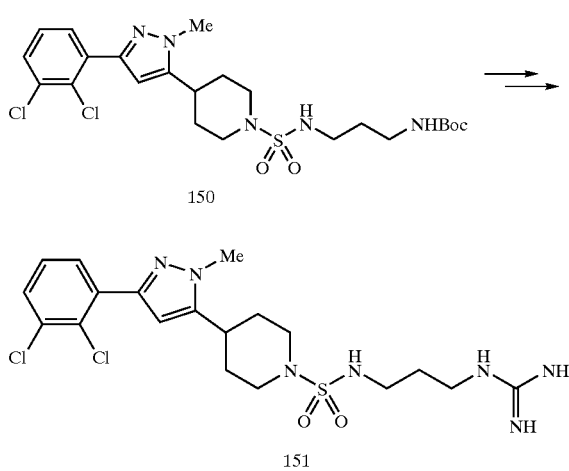

a) To a solution of 25 (1.0 g, 2.9 mmol) in dichloromethane (10 mL) was added 1M NaOH (10 mL). The aqueous layer was extracted with dichloromethane (2×10 mL); the combined organic layer was dried over $Na_2SO_4$, concentrated under reduced pressure, and azeotroped with benzene (3×5 mL) to give the free amine (891 mg, 99%). To a solution of sulfuryl chloride (1.0M in dichloromethane, 2.7 mL, 2.7 mmol) in dichloromethane (20 mL) at −78° C. under nitrogen was added the free amine in dichloromethane (5 mL) and triethylamine (443 µL, 3.2 mmol) dropwise. The reaction was stirred at −78° C. for 2 h, the dry ice bath was removed, and stirring continued at room temperature overnight. The mixture was diluted with dichloromethane (10 mL), partitioned with 1M HCl (20 mL) and separated. The aqueous layer was extracted with dichloromethane (3×10 mL); and the combined organic layer was dried over $Na_2SO_4$ and concentrated under reduced pressure to yield 149 (809 mg, 72%). ES (+) MS m/e=410 (M+1).

b) To 149 (60 mg, 0.15 mmol) in dichloromethane (1 mL) was added triethylamine (23 µL, 0.17 mmol) followed by N-Boc-propanediamine (39 mg, 0.23 mmol). The reaction was stirred overnight at room temperature and then was partitioned between dichloromethane (5 mL) and 1M HCl (5 mL). The aqueous layer was extracted with dichloromethane (2×5 mL); the combined organic layer was dried over $Na_2SO_4$ and concentrated under reduced pressure to provide 150. ES (+) MS m/e=490 (M−55).

c) Title compound 151 was prepared according to the procedure of Example 16j except for using 150 as a reagent instead of 27. ES (+) MS m/e=488 (M+1).

Example 64

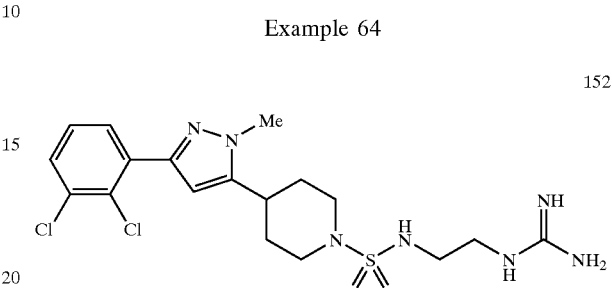

Title compound 152 was prepared from 149 according to the procedure of Example 63b,c except for using N-Boc-ethylenediamine as a reagent instead of N-Boc-propanediamine. ES (+) MS m/e=474 (M+1).

Example 65

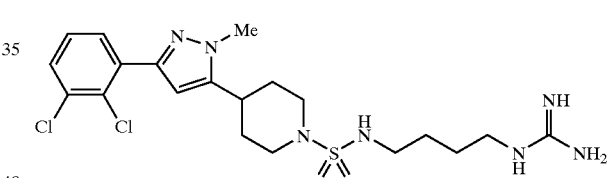

Title compound 153 was prepared from 149 according to the procedure of Example 63b,c except for using N-Boc-butanediamine as a reagent instead of N-Boc-propanediamine. ES (+) MS m/e=502 (M+1).

Example 66

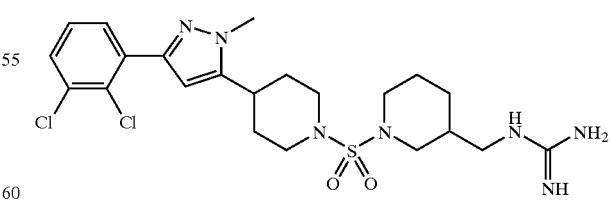

Title compound 154 was prepared from 149 according to the procedure of Example 63b,c except for using 3-aminomethyl-N-Boc-piperidine as a reagent instead of N-Boc-propanediamine.

Example 67

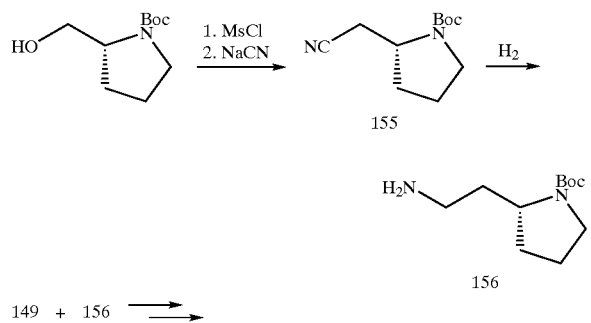

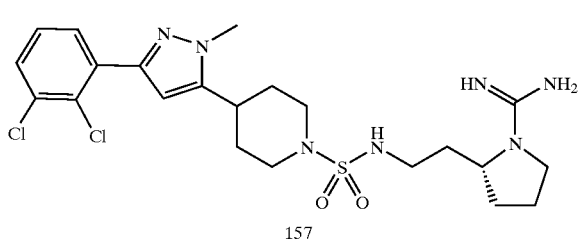

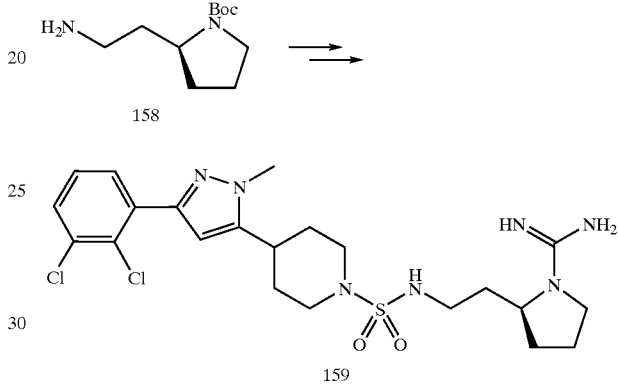

a) To a solution of Boc-D-prolinol (3.05 g, 15.1 mmol) in dichloromethane (30 mL) at 0° C. was added triethylamine (2.66 mL, 19 mmol) followed by mesyl chloride (1.35 mL, 17.5 mmol). The reaction mixture was warmed to room temperature, stirred for 2 h, and then partitioned between dichloromethane and water. The aqueous layer was extracted with dichloromethane; the organic layer was extracted with 1M HCl, dried over MgSO$_4$, and concentrated in vacuo.
To the resulting yellow oil in DMF (20 mL) at 55° C. was added NaCN (1.47 g, 30 mmol). The reaction was stirred overnight and monitored by TLC. After 15 h, the reaction was only 50% complete. To the solution was added KCN (1.3 g, 20 mmol) and the reaction was stirred an additional 24 h. The reaction mixture was cooled to room temperature and then partitioned between dichloromethane and water. The organic layer was extracted with water, dried over MgSO$_4$, and concentrated in vacuo. Purification of the residue by flash chromatography (SiO$_2$: 20% ethyl acetate in hexanes) provided 155 (1.75 g, 55%) as a colorless oil.

b) To a solution of 155 (1.75 g, 8.3 mmol) in saturated ammonia/ethanol (30 mL) was added Raney nickel (slurry in water, 3 mL). The solution was shaken on a Parr hydrogenator (H$_2$, 40 psi) for 3 h, filtered through Celite, and then washed with methanol. The filtrate was dried over Na$_2$SO$_4$ and concentrated in vacuo to provide (1.75 g, 100%) of 156.

c) Title compound 157 was prepared from 149 according to the procedure of Example 63b,c except for using (R)-2-aminoethyl-N-Boc-pyrrolidine as a reagent instead of N-Boc-propanediamine. ES (+)MS m/e=514 (M+1).

Example 68

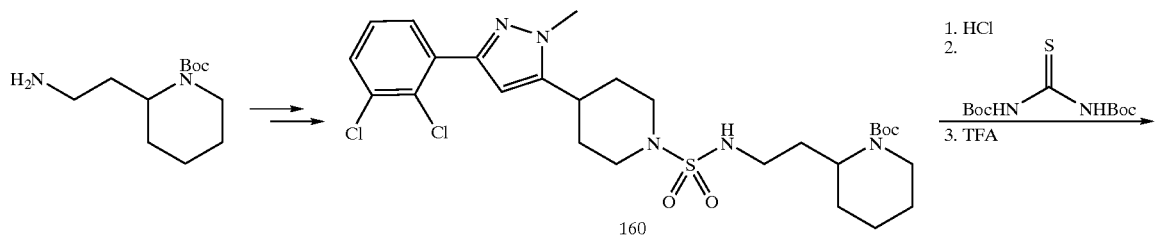

a) Compound 158 was prepared according to the procedure of Example 67a,b except for using Boc-L-prolinol as a reagent instead of Boc-D-prolinol.

b) Title compound 159 was prepared from 149 according to the procedure of Example 63b,c except for using (S)-2-aminoethyl-N-Boc-pyrrolidine as a reagent instead of N-Boc-propanediamine. ES (+) MS m/e=600 (M+1).

Example 69

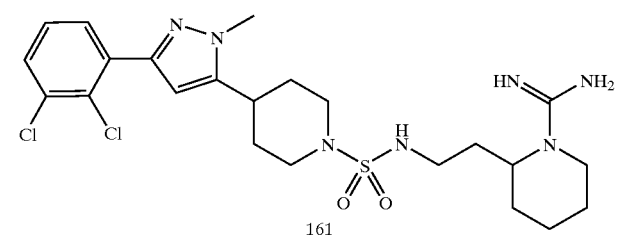

a) Compound 160 was prepared from 149 according to the procedure of Example 63b except for using 2-aminoethyl-N-Boc-piperidine as a reagent instead of N-Boc-propanediamine. ES (+) MS m/e=600 (M+1).

b) A solution of 160 in HCl/dioxane (4N, 1 mL) was stirred at room temperature for 30 min. The solvent was removed under reduced pressure to provide the desired amine as the hydrochloride salt which was used without purification.

To the hydrochloride salt (107 mg, 0.2 mmol) in dichloromethane (0.5 mL) was added a solution of 2-chloro-N-methylpyridinium iodide (77 mg, 0.3 mmol), N,N'-bis-Boc-thiourea (83 mg, 0.3 mmol), and triethylamine (42 μL, 0.3 mmol) in dichloromethane (0.5 mL). The reaction was stirred at room temperature overnight and the solvent was removed under reduced pressure.

The protected guanidine was dissolved in TFA/dichloromethane (1: 1, 1 mL) and stirred at room temperature for 3 h. The solvent was removed under reduced pressure to afford the crude guanidine as the trifluoroacetate salt. The crude material was purified by RP HPLC to provide 161. ES (+) MS m/e=542 (M+1).

Example 70 a) To a solution of 25 (4.5 g, 12.9 mmol) and triethylamine (3.8 mL, 27.1 mmol) in dichloromethane (60 mL) was added portionwise triphosgene (3.8 g, 12.9 mmol). The reaction was stirred at room temperature for 30 minutes and then partitioned between dichloromethane (20 mL) and 1M HCl (50 mL). The aqueous layer was extracted with dichloromethane (3×50 mL); the combined organic layer was dried over $Na_2SO_4$ and concentrated under reduced pressure to provide 162 (4.8 g, 100%). ES (+) MS m/e=372 (M+1).

b) To a solution of 162 (74 mg, 0.20 mmol) in dichloromethane (1 mL) was added triethylamine (56 μL, 0.40 mmol) followed by N-Boc-propanediamine (35 mg, 0.20 mmol). The reaction was stirred overnight at room temperature and then partitioned between dichloromethane (5 mL) and 1M HCl (5 mL). The aqueous layer was extracted with dichloromethane (2×5 mL); the combined organic layer was dried over $Na_2SO_4$ and concentrated under reduced pressure to provide 163. ES (+) MS m/e= 510 (M+1).

c) Title compound 164 was prepared according to the procedure of Example 16j except for using 163 as a reagent instead of 27. ES (+) MS m/e=451 (M+1).

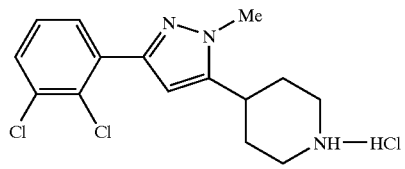 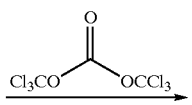

25

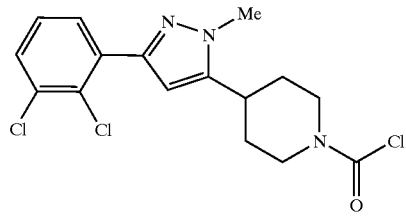

162

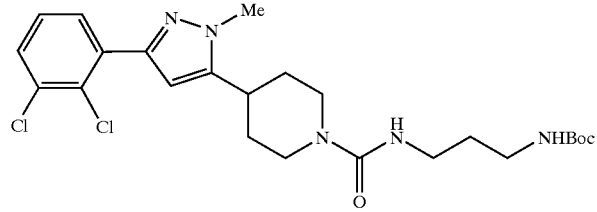

163

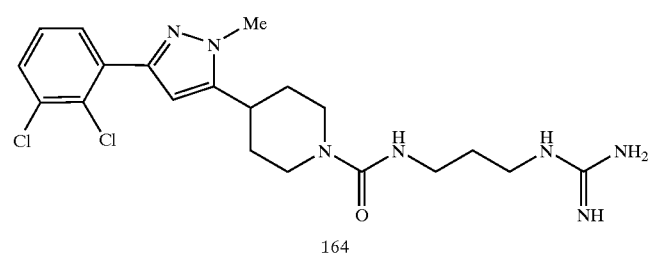

164

Example 71

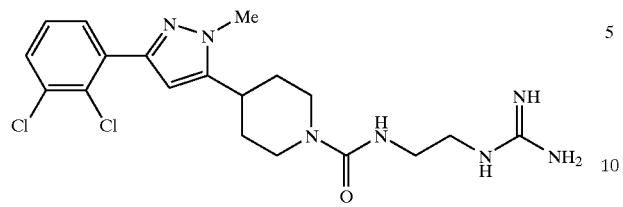

165

Title compound 165 was prepared from 162 according to the procedure of Example 70b,c except for using N-Boc-ethylenediamine as a reagent instead of N-Boc-propanediamine. ES (+) MS m/e=437 (M+1).

Example 72

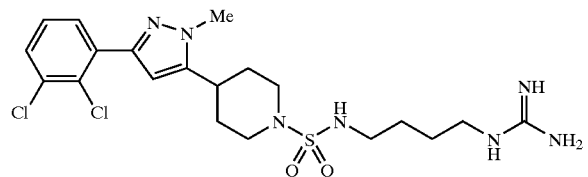

166

Title compound 166 was prepared from 162 according to the procedure of Example 70b,c except for using N-Boc-butanediamine as a reagent instead of N-Boc-propanediamine. ES (+) MS m/e=465 (M+1).

Example 73

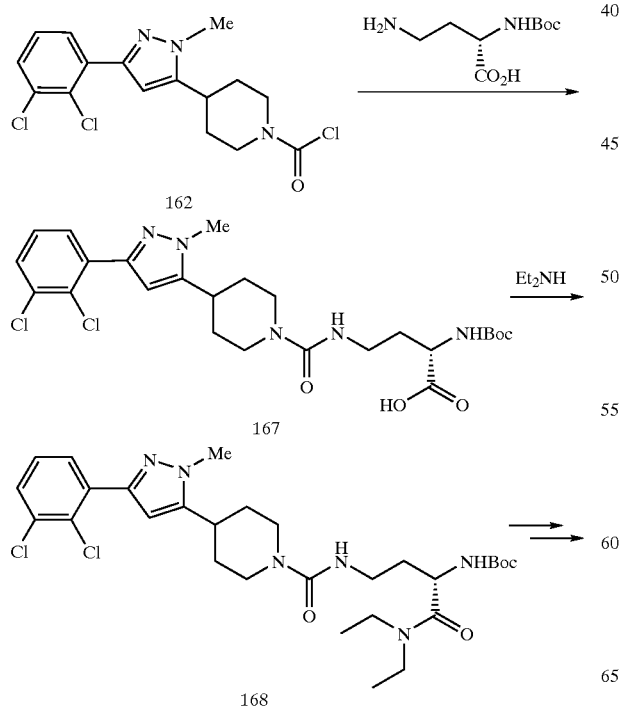

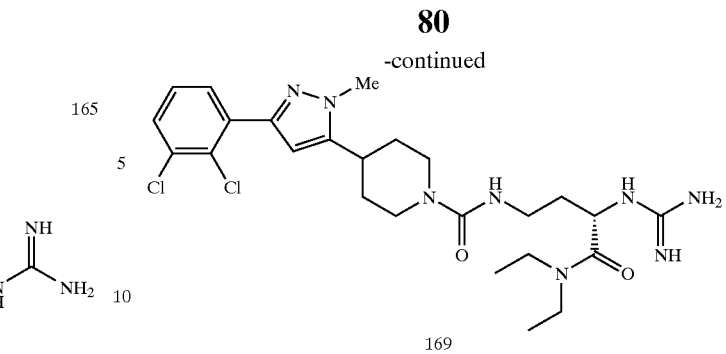

169 a) To a solution of 162 (4.8 g, 12.9 mmol) in THF (40 mL) was added a solution of N-Boc-diaminobutyric acid (3.4 g, 15.5 mmol) in water/triethylamine (1:1, 20 mL). The reaction was stirred at room temperature for 2 h and then the mixture was partitioned between ethyl acetate (100 mL) and 1M HCl (100 mL). The aqueous layer was extracted with ethyl acetate (3×70 mL); the combined organic layer was dried over $Na_2SO_4$ and concentrated under reduced pressure to afford 7.0 g (99%) of 167. ES (+) MS m/e=554 (M+1).

b) To a solution of 167 (63 mg, 0.11 mmol) and triethylamine (38 μL, 0.27 mmol) in dichloromethane (0.5 mL) was added 1,1'-carbonyldiimidazole (23 mg, 0.14 mmol). After 1 h, diethylamine (14 μL, 0.14 mmol) was added and the reaction was stirred overnight. The solvent was removed under reduced pressure to yield 168 which was used without further purification. ES (+) MS m/e=609 (M+1).

c) Title compound 169 was prepared according to the procedure of Example 16j except for using 168 as a reagent instead of 27. ES (+) MS m/e=551 (M+1).

Example 74

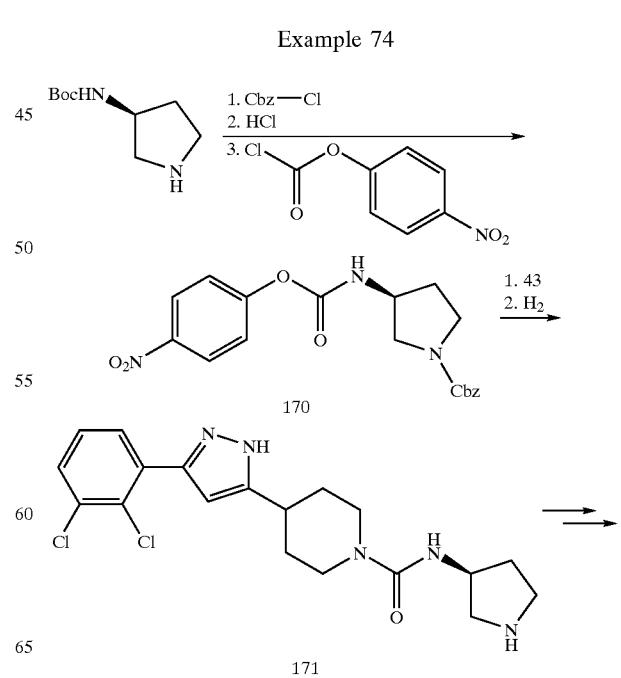

81

-continued

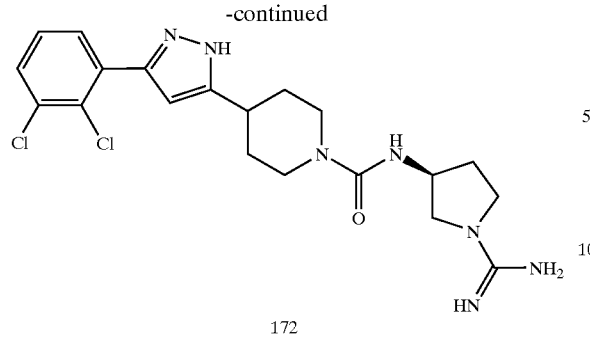

172 a) To a solution of (3S)-N-Boc-aminopyrrolidine (2.0 g, 10.7 mmol) and triethylamine (1.6 mL, 11.8 mmol) in dichloromethane (45 mL) was added benzyl chloroformate (1.5 mL, 10.2 mmol). The reaction was stirred at room temperature for 2 h, then partitioned between water (20 mL) and dichloromethane. The aqueous layer was extracted with dichloromethane (2'20 mL); the combined organic layer was washed with 1M HCl (20 mL), dried over $Na_2SO_4$, and concentrated under reduced pressure to yield the desired bis-carbamate (2.9 g, 88%).
A solution of the bis-carbamate (500 mg, 1.6 mmol) in HCl/dioxane (4N in dioxane, 6 mL) was stirred at room temperature for 30 minutes. The solvent was removed under reduced pressure to provide the amine (400 mg, 100%) as the hydrochloride salt.
To the amine (400 mg, 1.6 mmol) and pyridine (0.29 mL, 3.6 mmol) in dichloromethane (6 mL) at 0° C. was added p-nitrophenyl chloroformate (299 mg, 1.5 mmol). The reaction mixture was stirred at 0° C. for 2 h and then stirred at room temperature overnight. The solution was diluted and partitioned between dichloromethane (10 mL) and 1M HCl (15 mL). The aqueous layer was extracted with dichloromethane (3×15 mL); the combined organic layer was dried over $Na_2SO_4$ and concentrated under reduced pressure. Purification of the crude material by flash chromatography ($SiO_2$: 40% ethyl acetate in hexanes) provided 170 (190 mg, 33%). ES (+) MS m/e= 386 (M+1).

b) A solution of 170 (177 mg, 0.46 mmol) and 43 in pyridine (2.5 mL) was stirred at reflux for 3 h. The reaction mixture was cooled to room temperature and then partitioned between ethyl acetate (10 mL) and 1M HCl (10 mL). The aqueous layer was extracted with ethyl acetate (3×10 mL); the combined organic layer was dried over $Na_2SO_4$ and concentrated under reduced pressure to yield the urea (337 mg) which was used without purification.
To a solution of urea in methanol/ethyl acetate (1:1, 5 mL) was added 10% palladium on carbon (75 mg). The suspension was stirred under an atmosphere of hydrogen at room temperature for 2 h. The reaction mixture was filtered through Celite and washed with methanol (2×10 mL). The filtrate was concentrated under reduced pressure to provide 171 (190 mg) as an oil. ES (+) MS m/e=408 (M+1).

c) Title compound 172 was prepared according to the procedure of Example 16j except for using 171 as a reagent instead of 27. ES (+) MS m/e=450 (M+1).

82

Example 75

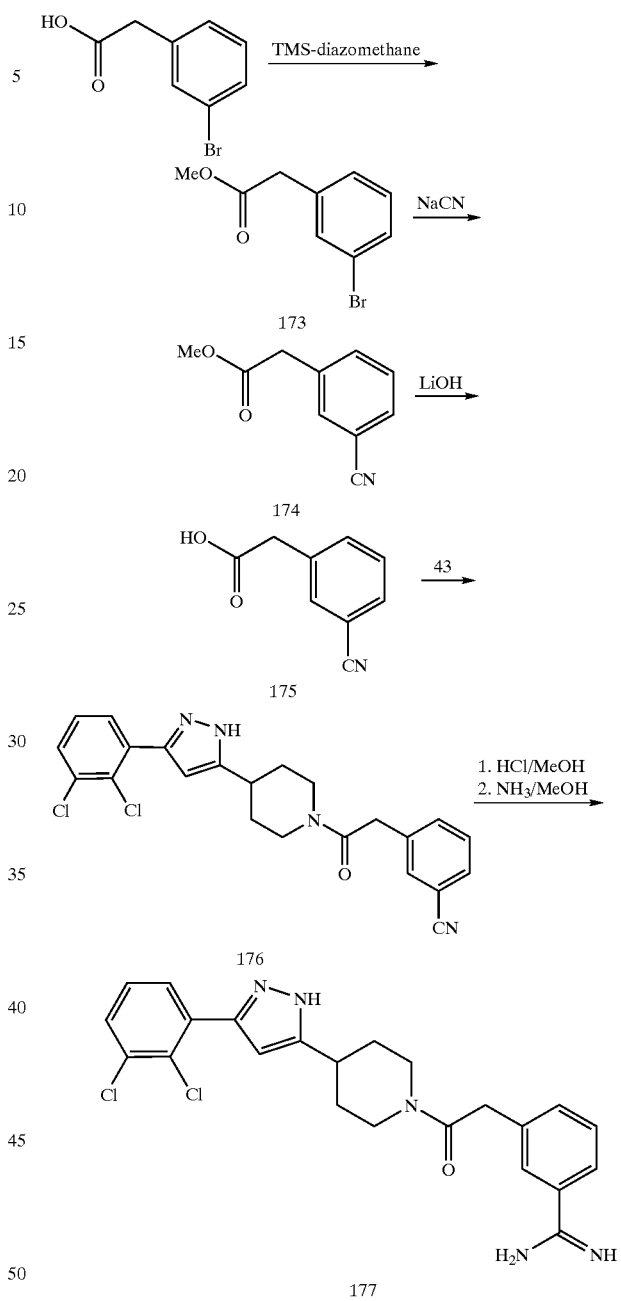

a) To 3-bromophenyl acetic acid (5.1 g, 23.7 mmol) in toluene (60 mL) and methanol (6 mL) was added dropwise TMS.diazomethane (2.0M in hexanes, 15 mL, 30 mmol). The solvent was removed under reduced pressure to provide 173 (5.45 g, 100%) as a yellow oil.

b) To a solution of 173 (3.43 g, 15 mmol) in propionitrile (22 mL) was added NaCN (1.47 g, 30 mmol), CuI (0.29 g, 1.5 mmol), and $Pd(PPh_3)_4$ (0.86 g, 0.75 mmol). The reaction mixture was heated to reflux and stirred overnight. The solution was cooled, filtered through Celite, and then partitioned between ethyl acetate and brine. The organic layer was dried over $Na_2SO_4$, filtered, and concentrated in vacuo to provide 174 (0.52 g, 20%). ES (+) MS m/e=176 (M+1).

c) To a solution of 174 (0.11 g, 0.61 mmol) in THF (1 mL) and water (0.25 mL) was added lithium hydroxide monohydrate (31 mg, 0.75 mmol). After 3 h the reaction mixture was partitioned between ethyl acetate and 1N HCl. The aqueous layer was extracted twice with ethyl acetate, dried over $Na_2SO_4$, filtered, and concentrated in vacuo to provide 175 (82 mg, 84%) as a white solid.

d) To a solution of 43 (200 mg, 0.6 mmol) in dichloromethane was added 175 (82 mg, 0.51 mmol), EDC (115 mg, 0.6 mmol), HOBt (92 mg, 0.6 mmol), and triethylamine (0.15 mL, 1.1 mmol). After stirring the reaction mixture overnight the solution was partitioned between dichloromethane and water. The aqueous layer was extracted with dichloromethane; the organic layer was extracted with 1N HCl, dried over $Na_2SO_4$, filtered, and concentrated in vacuo. Purification by flash chromatography ($SiO_2$: 100% ethyl acetate) provided 176 (166 mg, 77%). ES (+) MS m/e=440 (M+1).

e) To 176 (70 mg, 0.16 mmol) was added saturated HCl in MeOH (3 mL). The reaction was warmed to 60° C., stirred for 1.5 h, and then concentrated in vacuo. The crude residue was dissolved in ammonia/MeOH (2M, 3 mL), warmed to 60° C., and stirred for 1.5 h. The solvent was removed in vacuo and the material was purified by RP-HPLC to provide 177 as a white solid. ES (+) MS m/e=457 (M+1).

Example 76

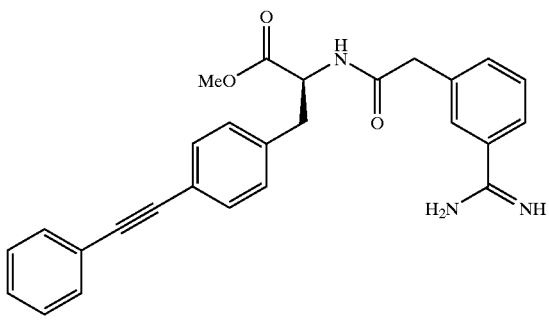

178

Title compound 178 was prepared according to the procedure of Example 75d,e except for using 1 as a reagent instead of 43. ES (+) MS m/e=440 (M+1).

Example 77

Scintillation Proximity Assay

Compounds are shown to inhibit binding of IL-2 to IL-2Rα by the following method:

1. IL-2 receptor alpha is expressed in SF9 insect cells and purified by his-tag affinity chromatography. The protein is then labeled with the NHS-ester of biotin by combining protein with four molar equivalents of biotin-LC-NHS (Pierce) in 50 mM $Na_2CO_3$ buffer at pH 9. The mixture is incubated for one hour at room temperature and purified by size-exclusion chromatography (Nap5, Pierce) into phosphate-buffered saline (PBS).
2. IL-2 is expressed in *E. Coli* cells and purified by standard procedures. Protein is then labeled with ($^3$H)-propionic acid NHS ester (Amersham) by combining 10 mmol IL-2 with 1 mCi propionic acid in 50 mM $Na_2CO_3$ buffer at pH 9. The mixture is incubated for one hour at room temperature and purified by size-exclusion chromatography (Nap 5, Pierce) into SuperBlock/PBS (Pierce).
3. Biotinylated-IL-2 receptor alpha is bound to streptavidin-coated scintillation beads (Amersham) by adding 100 nM protein to 10 mL of beads per 96-well plate. The mixture is incubated for 20 minutes at room temperature, centrifuged, and decanted. The beads are then resuspended in 1 mL of SuperBlock/PBS. 10 μL are aliquoted to each well in a clear-bottom 96-well plate (Wallac).
4. The compounds to be tested are suspended in DMSO to a final concentration of 100 mM. The compounds are then serially diluted by three-fold dilutions in DMSO and 1.2 μL of each dilution is then transferred to a clean, 96-well plate. The DMSO solutions are mixed with 120 μL of a solution containing 8 nM 3H-labeled IL-2. 90 μL of this mixture is then transferred to the 96-well plate containing IL-2 receptor alpha-coated beads from step (3). The mixture is incubated for 20 min.
5. Luminescence is read in a Wallac Microbeta Scintillation Counter. Luminescence arises from binding of 3H-labeled IL-2 to the scintillant-containing beads; reduction in the luminescence is due to inhibition of the protein-protein interaction by binding of the compounds.

Compounds of this invention are active in this assay.

Example 78

Inhibition of STAT5 Phosphorylation

Cell Culture

1. CTLL-2 cells are grown to approximately $1\times10^6$ cells/mL in a 37° C., 5% $CO_2$, incubator; using complete media [RPMI 1640 (liquid) with L-glutamine, 10 mM HEPES, 1 mM sodium pyruvate, 4.5 g/L glucose, 1.5 g/L sodium bicarbonate, 10% fetal bovine serum, 2-mercaptoethanol, and antibiotic/antimycotic (10,000 units/mL penicillin G sodium, 10,000 μg/mL streptomycin sulfate, 25 μg/mL amphotericin B)] plus 5 ng/mL IL-2.
2. When cells are close to $1\times10^6$ cells/mL, they are starved without IL-2 overnight. The cells are spun down (1100 rpm for 5 min), resuspended in IL-2-free complete media to wash, spun down again, resuspended in IL-2-free complete media to the same initial volume, and incubated overnight.

Sample Testing

1. The compounds are diluted in DMSO into Eppendorf tubes.
2. 2 μL of each compound dilution is aliquoted into a 15 ml conical tube. 1478 μL complete media (no IL-2) is added. 20 μL diluted IL-2 (0.01 ng/L) is added (the final concentration is 0.1 ng/ml).
3. The starved cells are counted, spun down, and resuspended (in pre-warmed complete media) to $8\times10^6$ cells/mL. 500 μL is aliquoted to each tube, to give $4\times10^6$ cells per tube, 2 mL final volume.
4. The tubes are incubated for 30 min in a 37° C. incubator.

Cell Extract Preparation

1. The cells are spun down (1100 rpm for 5 min), and excess media removed. The cell pellet is resuspended and lysed with 30 μL of M-PER buffer (from Pierce) containing protease inhibitors [using either (a) 10 μg/mL aprotinin, 10 μg/mL antipapain, 5 μg/mL leupeptin, and 1 mg/mL Pefablock SC, or (b) complete mini protease inhibitor cocktail tablets from Roche (catalog # 183615] and phosphatase inhibitors [50 mM NaF, 80 mM sodium glycerophosphate, 2 mM sodium vanadate (heat activated stock solution)], and is then placed on ice.
2. The suspensions are transferred to Eppendorf tubes, submitted to a freeze/thaw cycle (dry ice/room temperature), and spun in a microcentrifuge at full speed for 15 min in a cold room.
3. The supernatant is transferred to a new tube; and protein concentration quantified using Bio-Rad protein assay dye reagent (Bio-Rad Laboratories, catalog #500–0006)

Gel Electrophoresis and Western Blotting 1. 20 μg of protein extract is mixed with sample buffer and reducing agent (Invitrogen/Novex), then heated for 10 min at 70° C. Samples are spun in a microcentrifuge briefly to collect all sample at the bottom of the tube, then loaded onto a mini-protein gel (Invitrogen/Novex) (using either 4–12% Bis-Tris or 10% Bis-Tris gels). Full Range Rainbow Markers (Amersham) are loaded in one lane. 500 μL antioxidant (Invitrogen/Novex) is added into then inner buffer chamber, and the gel electrophoresed at 180 V for 1 h in 1×MOPS running buffer (Invitrogen/Novex).
2. The gel is transferred to a PVDF membrane (Invitrogen/Novex) according to the manufacturer's instructions. This entails pre-wetting the PVDF membrane in methanol, then equilibrating in transfer buffer with either 10% (one gel) or 15% (two gels) methanol added, and transferring at 35V for 1 h. The gel is cut horizontally at around the 50K marker to obtain a top and a bottom half.
3. The membrane is blocked with 5% non-fat dry milk (NFDM) in 1×TBS+0.05% Tween 20 (TBST) for 1 h at room temperature on an orbital shaker.
4. The primary antibodies are diluted in 5% NFDM in TBST. For the top half, Phospho-STAT5 (Upstate Biotech) at 1:1000 is used. For the bottom half, PCNA (Pharmingen) at 1:2000, or cdc2 (Transduction Labs) at 1:1000 is used.
5. The membranes are incubated overnight at 4° C. on a nutator; and the blot washed 3–4 times (for about 15 min each) with TBST.

Secondary Antibodies and Development Procedures

1. HRP-conjugated rabbit anti-mouse antibody (Zymed) is diluted 1:1000 in 5% NFDM in TBST, and incubated for several hours at room temperature on a nutator. The blot is washed 3–4 times (for about 15 min each) with TBST. The blot is developed using ECL Plus Western blotting detection reagents (Amersham): The reagents are mixed in a 1:40 dilution, the membrane dried briefly, and about 5 mL of reagent solution applied to the protein side of the membrane; which is then incubated on a flat surface with no agitation for 5 min, excess liquid dripped off, and the membrane wrapped in Saran wrap. The membrane is exposed to Kodak BioMax MR film for 10 sec to 5 min; and the film developed.
2. AP-conjugated donkey anti-mouse antibody (Jackson Immunoresearch) is diluted 1:2000 or 1:400 in 5% NFDM in TBST, then incubated for several hours at room temperature on a nutator. The blot is washed 3–4 times (for about 15 min each) with TBST. The blot is developed using ECF substrate for Western blotting (Amersham): The reagents are mixed, and about 2 mL applied to the protein side of the wet membrane; which is then incubated for 2–20 min on a flat surface with no agitation, dried thoroughly, and scanned scan on a phosphorimager (using the fluorescence/fluorescein setting: excitation 532, emission 526 SP.

Compounds of this invention are active in this assay.

While this invention has been described in conjunction with specific embodiments and examples, it will be apparent to a person of ordinary skill in the art, having regard to this disclosure, that equivalents of the specifically disclosed materials and techniques will also be applicable to this invention; and such equivalents are intended to be included within the following claims.

What is claimed is:

1. A compound of formula I

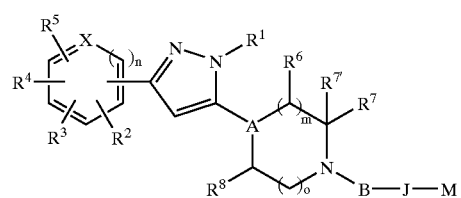

where:

m is an integer selected from 0, 1, and 2;

n and o are integers independently selected from 0 and 1;

A is selected from the group consisting of N and CH;

B is selected from the group consisting of —$CH_2$—$CH_2$—, —$CH_2$—$CH_2$—$CH_2$—, —$CH_2$—$CH_2$—NH—, —$CH_2$—O—$CH_2$—, —$CH_2$—S—$CH_2$—, —C(=O)—NH—, —C(=O)—$CH_2$—, —$CH_2$—C(=O)—NH—, —C(=O)—$CH_2$—C(=O)—, —C(=O)—NH—$CH_2$—, —C(=O)—, —S(=O)—, —S(=O)$_2$—, —S(=O)—NH—, —S(=O)$_2$—NH—, —S(=O)—$CH_2$—, —S(=O)$_2CH_2$—, —S(=O)—$CH_2$—NH—, —S(=O)$_2$—$CH_2$—NH—, —S(=O)$_2$—NH—$CH_2$—, —$CH_2$—S(=O)$_2$—NH—, —C(=O)—NH—S(=O)$_2$—, —S(=O)$_2$—NH—C(=O)—, —C(=O)—$CH_2$—S(=O)$_2$—, and —S(=O)$_2$—$CH_2$—C(=O)—;

J is absent or selected from the group consisting of —O—, —S—, —$CHR^{15}$—O—, —$CH_2$—$CHR^{15}$—O—, —NH—, —NH—$CHR^{15}$—, —NH—$CHR^{15}$—C(=O)—, —C(=O)—, —$CH_2$—, —$CHR^{15}$—$CH_2$—NH—, —C(=O)—$CHR^{15}$—, —NH—C(=O)—CH($C_1$-$C_6$alkyl)-, —NH—C(=O)—CH($C_3$-$C_{12}$cycloalkyl)-, —$CH_2CH_2$—, —$CH_2$NH—, —$CH_2$—NH—C(=O)—, —$CH_2$—NH—C(=O)—$C_1$-$C_6$alkyl-, —$CH_2$—NH—C(=O)—CH($C_3$-$C_{12}$cycloalkyl)- and —C(=O)—$CHR^{15}$—NH—; or B—J is selected from the group consisting of —C(=O)—$CH_2$—NH—C(=O)—CH($C_1$-$C_6$alkyl), —C(=O)—$CH_2$—NH—C(=O)—CH($C_3$-$C_{12}$cycloalkyl)-, —C(=O)—NH—($C_2$-$C_6$alkyl), —S(=O)$_2$—NH—($C_2$-$C_6$alkyl)-, —C(=O)—NH—, —S(=O)$_2$—NH—, —C(=O)—$CH_2$— and —S(=O)$_2$—$CH_2$—;

L is selected from the group consisting of —O—, —$CH_2$—O—, —O—$CH_2$—, —$CH_2$—$CH_2$—O—, —O—$CH_2$—$CH_2$—, —$CH_2$—O—$CH_2$—, —$CH_2$—S—$CH_2$—, —C(=O)—NH—, —O—C(=O)—NH—, —$CH_2$—C(=O)—NH—, —C(=O)—$CH_2$—NH—, —C(=O)—NH—$CH_2$—, —NH—C(=O)—, —NH—C(=O)—O—, —NH—$CH_2$—C(=O)—, —NH—NH—C(=O)—$CH_2$—, —$CH_2$—NH—C(=O)—, —NH—C(=O)—NH—, —NH—S(=O)$_2$—NH—, —NH—S(=O)$_2$—, —NH—S(=O)$_2$—$CH_2$—, —$CH_2$—NH—S(=O)$_2$—, —S(=O)$_2$—NH—, —S(=O)$_2$—NH—CH$_2$—, —CH$_2$—S(=O)$_2$—NH—, —C(=O)—NH—S(=O)$_2$—, —S(=O)$_2$—NH—C(=O)—, —CH$_2$—NH—, —CH$_2$—CH$_2$—NH—, —NH—CH$_2$—, —NH—CH$_2$—CH$_2$—, —CH$_2$—NH—CH$_2$—, —C≡C—, —CH$_2$—C≡C—, —CH$_2$—CH$_2$—, —CH$_2$—CH$_2$—CH$_2$—, —CH$_2$—CH=CH—, CH=CH—CH$_2$—, and —CH=CH—;

M is selected from the group consisting of R$^9$,

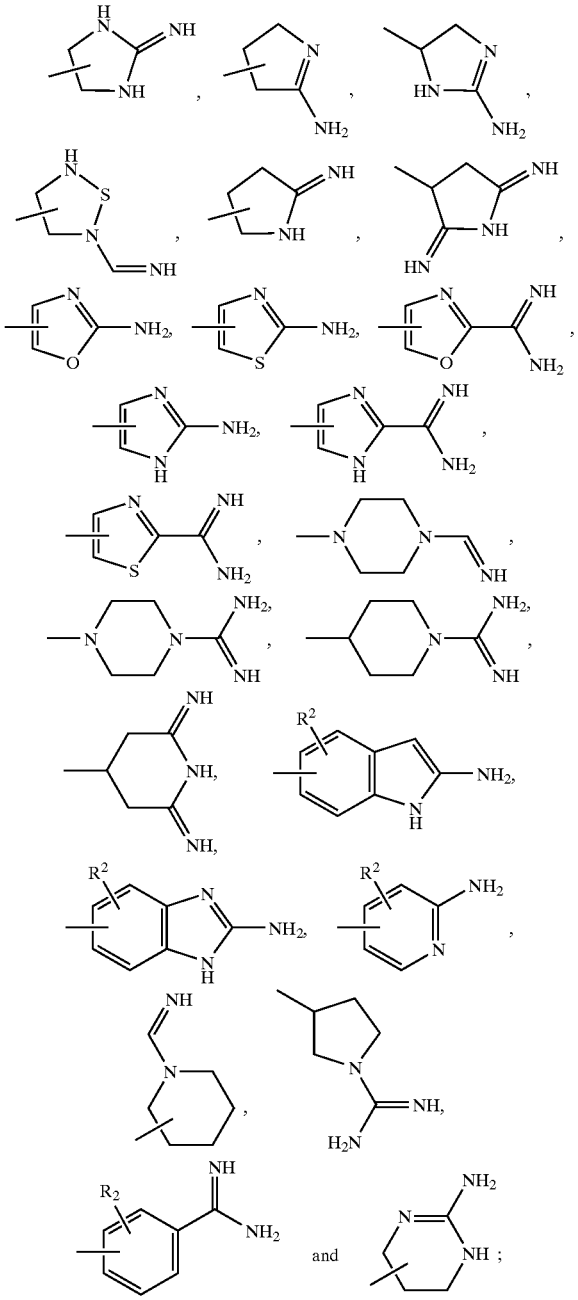

Q is selected from the group consisting of —C(=O)OR$^{16}$, —C(=O)—NH—C(=O)—CF$_3$, —C(=O)—NH—S(=O)$_2$—R$^2$, —C(=O)—NR$^1$—OH, 5-oxo-4,5-dihydro[1,2,4]oxadiazol-3-yl, and tetrazolyl;

X is A when n is 1, and is CH, N, O or S when n is 0;

R$^1$ is selected from the group consisting of hydrogen, (C$_1$–C$_6$)alkyl, halo-(C$_1$–C$_6$)alkyl, and (C$_3$–C$_6$)cycloalkyl;

R$^2$, R$^3$ and R$^5$ are individually selected from the group consisting of hydrogen, cyano, nitro, phenyl, phenoxy, benzyl, C$_1$–C$_6$alkyl, halo, halo-C$_1$–C$_6$alkyl, C$_3$–C$_6$cycloalkyl, C$_1$–C$_6$alkoxy, hydroxy, C$_1$–C$_2$alkoxy-methoxy, hydroxy-C$_1$–C$_6$alkyl, formyl, C$_1$–C$_6$alkylcarbonyl, amino, C$_1$–C$_6$alkylamino, aminocarbonyl, C$_1$–C$_6$alkylaminocarbonyl, formylamino, and C$_1$–C$_6$alkylcarbonylamino, where any alkyl or phenyl may optionally be substituted with halo or Q;

R$^4$ is selected from the group consisting of R$^2$ and

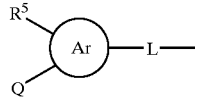

where Ar is a homo- or hetero-aryl group having 1 or 2 rings, each ring containing 5,6 or 7 ring atoms of which 1–3 may be heteroatoms selected from N, O and S;

R$^6$ is selected from the group consisting of hydrogen, C$_1$–C$_6$alkyl, halo, halo-C$_1$–C$_6$alkyl, C$_3$–C$_6$cycloalkyl, C$_1$–C$_6$alkoxy, C$_1$–C$_6$alkoxy-C$_1$–C$_6$alkyl, hydroxy, hydroxy-C$_1$–C$_6$alkyl, HC(=O)—C$_1$–C$_6$alkyl, carboxy, carboxy-C$_1$–C$_6$alkyl, carbonylamino-C$_1$–C$_6$alkyl, aminocarbonyl, (C$_1$–C$_6$alkyl)aminocarbonyl, di(C$_1$–C$_6$alkyl)aminocarbonyl, and aminocarbonyl-C$_1$–C$_6$alkyl;

R$^7$ is selected from the group consisting of hydrogen, C$_1$–C$_6$ alkyl, halo, halo-C$_1$–C$_6$alkyl, C$_3$–C$_6$cycloalkyl, C$_1$–C$_6$alkoxy, C$_1$–C$_6$alkoxy-C$_1$–C$_6$alkyl, hydroxy, hydroxy-C$_1$–C$_6$alkyl, HC(=O)—C$_1$–C$_6$alkyl, carboxy, carboxy-C$_1$–C$_6$alkyl, carbonylamino-C$_1$–C$_6$alkyl, aminocarbonyl, (C$_1$–C$_6$alkyl)aminocarbonyl, di(C$_1$–C$_6$alkyl)aminocarbonyl, and aminocarbonyl-C$_1$–C$_6$alkyl;

R$^{7'}$ is hydrogen; or

R$^7$ and R$^{7'}$ together with the carbon to which they are bonded form —C(=O)—;

R$^8$ selected from the group consisting of hydrogen, hydroxy, C$_1$–C$_6$alkoxy, C$_1$–C$_6$alkyl, halo, halo-C$_1$–C$_6$alkyl, and C$_3$–C$_6$cycloalkyl;

R$^9$ is selected from the group consisting of —NR$^{10}$R$^{11}$, —C(=NR$^{12}$)—NHR$^{13}$, —N=CR$^{14}$—NR$^{10}$R$^{11}$, —NR$^{13}$—CR$^{14}$=NR$^{12}$, and —NR$^{13}$—C(=NR$^{12}$)—NHR$^{13}$;

R$^{10}$, R$^{11}$, R$^{12}$, R$^{13}$ and R$^{14}$ are independently selected from the group consisting of hydrogen, hydroxy, hydroxy-C$_1$–C$_6$alkyl, C$_1$–C$_6$alkyl, halo-C$_1$–C$_6$alkyl, C$_1$–C$_6$alkoxy, C$_1$–C$_6$alkoxy-C$_1$–C$_6$alkyl, and C$_3$–C$_7$ cycloalkyl; or any member of the group R$^{10}$, R$^{11}$, R$^{12}$, R$^{13}$ together with the nitrogen to which it is attached forms a 5, 6 or 7 member heterocycle with any other member of the group, the heterocycle optionally containing one additional heteroatom selected from N, O and S;

R$^{15}$ is selected from the group consisting of hydrogen, C$_1$–C$_{12}$alkyl, C$_3$–C$_7$cycloalkyl, aminocarbonyl, C$_1$–C$_6$alkylaminocarbonyl, and di(C$_1$–C$_6$alkyl)aminocarbonyl; and R$^{16}$ is selected from the group consisting of hydrogen, C$_1$–C$_6$alkyl, C$_3$–C$_{13}$cycloalkyl, C$_6$–C$_{10}$aryl, acetylamino-C$_1$–C$_{12}$alkyl, C$_1$–C$_6$alkylcarbonyloxy-C$_1$–C$_6$alkyl, and C$_6$–C$_{10}$aryl-C$_0$–C$_6$alkylcarbonyloxy-C$_1$–C$_6$alkyl, or a pharmaceutically acceptable salt thereof.

2. The compound of claim 1 that is a compound of formula II

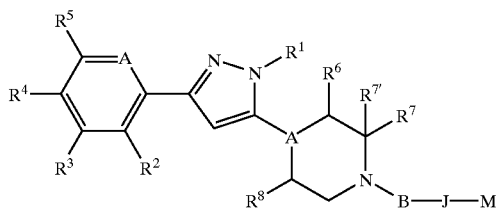

where the substituents are defined as in claim 1;

or a pharmaceutically acceptable salt thereof.

3. The compound of claim 2 that is a compound of formula III or formula III':

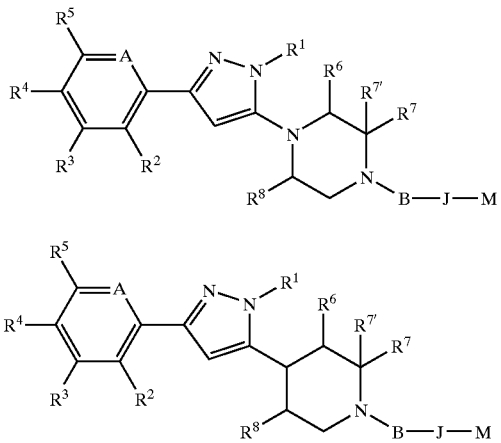

where the substituents are as defined in claim 1, or a pharmaceutically acceptable salt thereof.

4. The compound of claim 1 where $R^1$ is hydrogen or $(C_1-C_6)$ alkyl.

5. The compound of claim 1 where $R^2$ and $R^3$ are hydrogen, $C_1-C_6$alkyl, cyano, or halo.

6. The compound of claim 1 where B is —C(=O)— or —S(=O)$_2$—.

7. The compound of claim 1 where J is —CH$_2$—, —CH$_2$—CH$_2$—, —NH—, —NH—CH$_2$—, —CH$_2$—NH—, —CH$_2$—NH—C(=O)—, —CH$_2$—NH—C(=O)—C$_1$-C$_6$alkyl- or —CH$_2$—NH—C(=O)—CH(C$_3$-C$_{12}$cycloalkyl)-.

8. The compound of claim 1 where B—J is selected from the group consisting of —C(=O)—CH$_2$—NH—C(=O)—CH(C$_1$-C$_6$alkyl), —C(=O)—CH$_2$—NH—C(=O)—CH(C$_3$-C$_{12}$cycloalkyl)-, —C(=O)—NH—(C$_2$-C$_6$alkyl), —S(=O)$_2$—NH—(C$_2$-C$_6$alkyl)-, —C(=O)—NH—, —S(=O)$_2$—NH—, —C(=O)—CH$_2$— and —S(=O)$_2$—CH$_2$—.

9. A compound of formula II

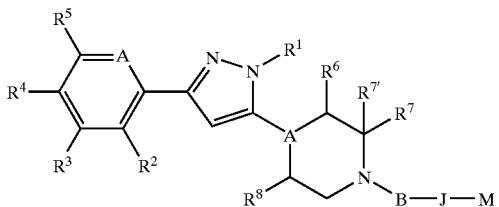

where:

A is selected from the group consisting of N and CH;

B is —C(=O)— or —S(=O)$_2$—;

J is —CH$_2$—, —CH$_2$—CH$_2$—, —NH—, —NH—CH$_2$—, —CH$_2$—NH—, —CH$_2$—NH—C(=O)—, —CH$_2$—NH—C(=O)—C$_1$-C$_6$alkyl-, or —CH$_2$—NH—C(=O)—CH(C$_3$-C$_{12}$cycloalkyl)-;

M is selected from the group consisting of

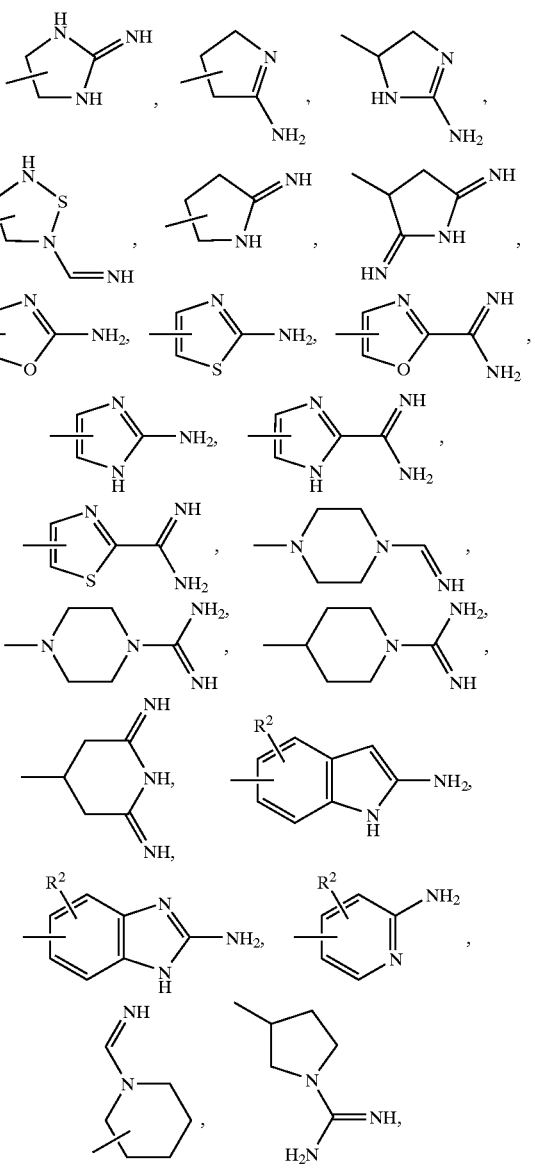

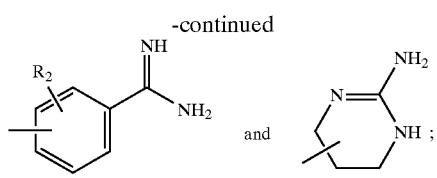
and
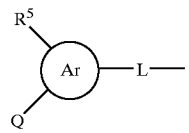

$R^1$ is hydrogen or $C_1$–$C_6$ alkyl;
$R^2$ and $R^3$ are hydrogen, $C_1$–$C_6$alkyl, cyano, or halo;
$R^4$ is hydrogen, $C_1$–$C_6$alkyl, cyano, halo or

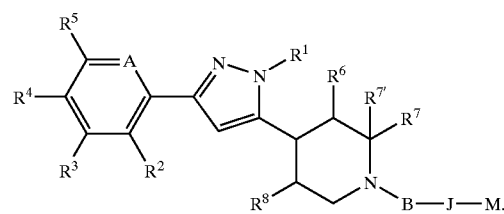

where Ar is phenyl, furyl, thienyl, oxazolyl, thiazolyl, or pyrrolyl;
$R^5$ is hydroxy or $C_1$–$C_3$alkoxy;
L is selected from the group consisting of —O—, —CH$_2$—O—, —O—CH$_2$— and —CH$_2$CH$_2$O—;
Q is selected from the group consisting of —C(=O)OR$^{16}$, —C(=O)—NH—C(=O)—CF$_3$, —C(=O)—NH—S(=O)$_2$—R$^2$, —C(=O)—NR$^1$—OH, 5-oxo-4,5-dihydro[1,2,4]oxadiazol-3-yl, and tetrazolyl;
$R^6$ is selected from the group consisting of hydrogen, $C_1$–$C_6$alkyl, halo, halo-$C_1$–$C_6$alkyl, $C_3$–$C_6$cycloalkyl, $C_1$–$C_6$alkoxy, $C_1$–$C_6$alkoxy-$C_1$–$C_6$alkyl, hydroxy, hydroxy-$C_1$–$C_6$alkyl, HC(=O)—$C_1$–$C_6$alkyl, carboxy, carboxy-$C_1$–$C_6$alkyl, carbonylamino-$C_1$–$C_6$alkyl, aminocarbonyl, ($C_1$–$C_6$alkyl)aminocarbonyl, di($C_1$–$C_6$alkyl)aminocarbonyl, and aminocarbonyl-$C_1$–$C_6$alkyl;
$R^7$ is selected from the group consisting of hydrogen, $C_1$–$C_6$ alkyl, halo, halo-$C_1$–$C_6$alkyl, $C_3$–$C_6$cycloalkyl, $C_1$–$C_6$alkoxy, $C_1$–$C_6$alkoxy-$C_1$–$C_6$alkyl, hydroxy, hydroxy-$C_1$–$C_6$alkyl, HC(=O)—$C_1$–$C_6$alkyl, carboxy, carboxy-$C_1$–$C_6$alkyl, carbonylamino-$C_1$–$C_6$alkyl, aminocarbonyl, ($C_1$–$C_6$alkyl)aminocarbonyl, di($C_1$–$C_6$alkyl)aminocarbonyl, and aminocarbonyl-$C_1$–$C_6$alkyl;
$R^{7'}$ is hydrogen; or
$R^7$ and $R^{7'}$ together with the carbon to which they are bonded form —C(=O)—;
$R^8$ is selected from the group consisting of hydrogen, hydroxy, $C_1$–$C_6$alkoxy, $C_1$–$C_6$alkyl, halo, halo-$C_1$–$C_6$alkyl, and $C_3$–$C_6$cycloalkyl;
$R^{16}$ is selected from the group consisting of hydrogen, $C_1$–$C_6$alkyl, $C_3$–$C_{13}$cycloalkyl, $C_6$–$C_{10}$aryl, acetylamino-$C_1$–$C_{12}$alkyl, $C_1$–$C_6$alkylcarbonyloxy-$C_1$–$C_6$alkyl, and $C_6$–$C_{10}$aryl-$C_0$–$C_6$alkylcarbonyloxy-$C_1$–$C_6$alkyl, or a pharmaceutically acceptable salt thereof.

10. The compound claim 9 that is a compound of formula III'

III'

11. A composition comprising a compound of claim 1 or 9 and a pharmaceutically acceptable excipient.

12. A method of treating a mammal having a disease for which the antagonism of IL-2/IL-2R binding is indicated, comprising administering to the mammal a therapeutically effective dose of a compound of claim 1 or 10.

13. The method of claim 12 where the disease is T-lymphocyte-induced rejection of an allograft.

14. The method of claim 13 where T-lymphocytes which express IL-2R in response to antigens of the allograft are contacted with the compound.

15. The method of claim 13 where the allograft is a skin allograft.

16. The method of claim 14 where the allograft is a transplanted organ.

17. The method of claim 16 where the transplanted organ is a heart.

18. The method of claim 12 where the disease is an autoimmune disease.

19. The method of claim 18 where the autoimmune disease is selected from the group consisting of rheumatoid arthritis, multiple sclerosis, uveitis, and psoriasis.

* * * * *